US012595289B2

(12) United States Patent
Katagiri et al.

(10) Patent No.: US 12,595,289 B2
(45) Date of Patent: Apr. 7, 2026

(54) THERAPEUTIC AGENT FOR BREAST CANCER COMPRISING BIG3-PHB2 INTERACTION-INHIBITING PEPTIDE DERIVED FROM PHB2

(71) Applicants: TOKUSHIMA UNIVERSITY, Tokushima (JP); ONCOTHERAPY SCIENCE, INC., Kawasaki (JP)

(72) Inventors: Toyomasa Katagiri, Tokushima (JP); Tetsuro Yoshimaru, Tokushima (JP); Akira Otaka, Tokushima (JP); Takashi Miyamoto, Kawasaki (JP); Yasuhide Okamoto, Kawasaki (JP)

(73) Assignees: TOKUSHIMA UNIVERSITY, Tokushima (JP); ONCOTHERAPY SCIENCE, INC., Kawasaki (JP)

( * ) Notice: Subject to any disclaimer, the term of this patent is extended or adjusted under 35 U.S.C. 154(b) by 947 days.

(21) Appl. No.: 17/297,986

(22) PCT Filed: Nov. 28, 2019

(86) PCT No.: PCT/JP2019/046505
§ 371 (c)(1),
(2) Date: May 27, 2021

(87) PCT Pub. No.: WO2020/111167
PCT Pub. Date: Jun. 4, 2020

(65) Prior Publication Data
US 2022/0098256 A1 Mar. 31, 2022

(30) Foreign Application Priority Data
Nov. 30, 2018 (JP) ................................ 2018-225660

(51) Int. Cl.
*C07K 14/47* (2006.01)
*A61P 35/00* (2006.01)
*A61K 38/00* (2006.01)

(52) U.S. Cl.
CPC .......... *C07K 14/4703* (2013.01); *A61P 35/00* (2018.01); *C07K 14/4748* (2013.01); *A61K 38/00* (2013.01)

(58) Field of Classification Search
CPC ............ C07K 14/4703; C07K 14/4748; C07K 19/00; A61P 35/00; A61P 43/00; A61K 38/00
See application file for complete search history.

(56) References Cited

U.S. PATENT DOCUMENTS

| | | |
|---|---|---|
| 2009/0175844 A1 | 7/2009 | Nakamura et al. |
| 2011/0135647 A1 | 6/2011 | Nakamura et al. |
| 2012/0014996 A1 | 1/2012 | Nakamura et al. |
| 2013/0011933 A1 | 1/2013 | Nakamura et al. |
| 2014/0162952 A1 | 6/2014 | Katagiri et al. |
| 2014/0228238 A1 | 8/2014 | Nakamura et al. |
| 2019/0023739 A1* | 1/2019 | Katagiri ................. A61K 38/10 |
| 2020/0255474 A1 | 8/2020 | Katagiri et al. |

FOREIGN PATENT DOCUMENTS

| | | |
|---|---|---|
| WO | 2006/085684 A2 | 8/2006 |
| WO | 2008/018642 A2 | 2/2008 |
| WO | 2013/018690 A1 | 2/2013 |
| WO | 2017/126461 A1 | 7/2017 |
| WO | 2019/017384 A1 | 1/2019 |

OTHER PUBLICATIONS

Qian (ACS Chem.Biol., 2013, 8, 423-431) (Year: 2013).*
Qian (Angew Chem Int Ed Engl, Feb. 1, 2017, 56(6), 1525-1529) (Year: 2017).*
Rhodes (Chem. Eur. J., 2017, 23, 12690-12703) (Year: 2017).*
Cirino (Biotechnology and Bioengineering, vol. 83, No. 6, Sep. 20, 2003) (Year: 2003).*
Gilles (The Journal of Biological Chemistry, vol. 263, No. 17, Issue of Jun. 15, 1988, 8204-8209). (Year: 1988).*
Postma (Eur.J.Org.Chem., 2014, 3519-3530] (Year: 2014).*
Bodanszky (Proc. Nat.Acad. Sci. USA, 1974, vol. 71, No. 7, 2791-2794). (Year: 1974).*
Chen, et al.; Brefeldin A-inhibited guanine nucleotide-exchange protein 3 (BIG3) is predicted to interact with its partner through an ARM-type α-helical structure; BMC Research Notes; 2014; 7:435; 8 pgs.
Chlebowski, et al.; Clinical perspectives on the utility of aromatase inhibitors for the adjuvant treatment of breast cancer; The Breast; 2009:18 (Suppl. 2): S1-S11.
Chumsri, et al.; Aromatase, Aromatase Inhibitors, and Breast Cancer; J. Steroid Biochem. Mol. Biol.; May 2011; 125(1-2):13-22.
Clarke, et al.; Cellular and Molecular Pharmacology of Antiestrogen Action and Resistance; Pharmacol. Rev.; Mar. 2001; 53(1):25-71.
Fisher, et al.; Tamoxifen for the Prevention of Breast Cancer: Current Status of the National Surgical Adjuvant Breast and Bowel Project P-1 Study; J. Natl. Cancer Inst.; Nov. 16, 2005; 97(22):1652-62.

(Continued)

*Primary Examiner* — Sudhakar Katakam
(74) *Attorney, Agent, or Firm* — Kilpatrick Townsend & Stockton LLP

(57) ABSTRACT

The present invention provides peptides containing the BIG3 polypeptide-binding site in a PHB2 polypeptide, which inhibit the binding between a PHB2 polypeptide and a BIG3 polypeptide, and pharmaceutical compositions containing the peptide. The peptides of the present invention have the ability to bind not to PHB2, whose expression is found in organs throughout the human body, but to BIG3, which is a protein highly expressed specifically in particularly estrogen receptor-positive cancer, and have excellent growth suppressive effects on BIG3-positive cancer cells. Accordingly, the peptides of the present invention are useful as therapeutic agents for breast cancer which can avoid expression of side effects.

6 Claims, 17 Drawing Sheets

Specification includes a Sequence Listing.

(56)     References Cited

OTHER PUBLICATIONS

Fisher, et al.; Five Versus More Than Five Years of Tamoxifen for Lymph Node-Negative Breast Cancer: Updated Findings From the National Surgical Adjuvant Breast and Bowel Project B-14 Randomized Trial; J. Natl. Cancer Inst.; May 2, 2001; 93(9):684-90.

Johnston; New Strategies in Estrogen Receptor-Positive Breast Cancer; Clin. Cancer Res.; Apr. 1, 2010; 16(7):1979-87.

Jordan; Tamoxifen: A Most Unlikely Pioneering Medicine; Nat. Rev. Drug Discov.; Mar. 2003; 2(3):205-13.

Kim, et al.; Activation of an estrogen/estrogen receptor signaling by BIG3 through its inhibitory effect on nuclear transport of PHB2/REA in breast cancer; Cancer Sci.; Aug. 2009; 100(8):1468-78.

Yoshimaru, et al.; Regulation of suppressive factor PHB2 by novel A-kinase anchoring protein BIG3 critical for proliferation of HER2 breast cancer cells; The $41^{st}$ Annual Meeting of the Molecular Biology Society of Japan Yoshishu; Nov. 9, 2018; 2P-0632; 6 pgs.

Yoshimaru, et al.; Targeting BIG3-PHB2 interaction to overcome tamoxifen resistance in breast cancer cells; Nature Communications; 2013; 4:2443; 13 pgs.

Yoshimaru, et al.; Stapled BIG3 helical peptide ERAP potentiates anti-tumour activity for breast cancer therapeutics; Scientific Reports; May 2017; 12:7(1):1821; 11 pgs.

Japan Patent Office; International Search Report of PCT/JP2019/046505; mailed Dec. 24, 2019.

Yoshimaru, et al.; Therapeutic advances in BIG3-PHB2 inhibition targeting the crosstalk between estrogen and growth factors in breast cancer; Cancer Sci.; May 2015; 106(5):550-8.

* cited by examiner

FIG. 2B
FIG. 2A
FIG. 2C
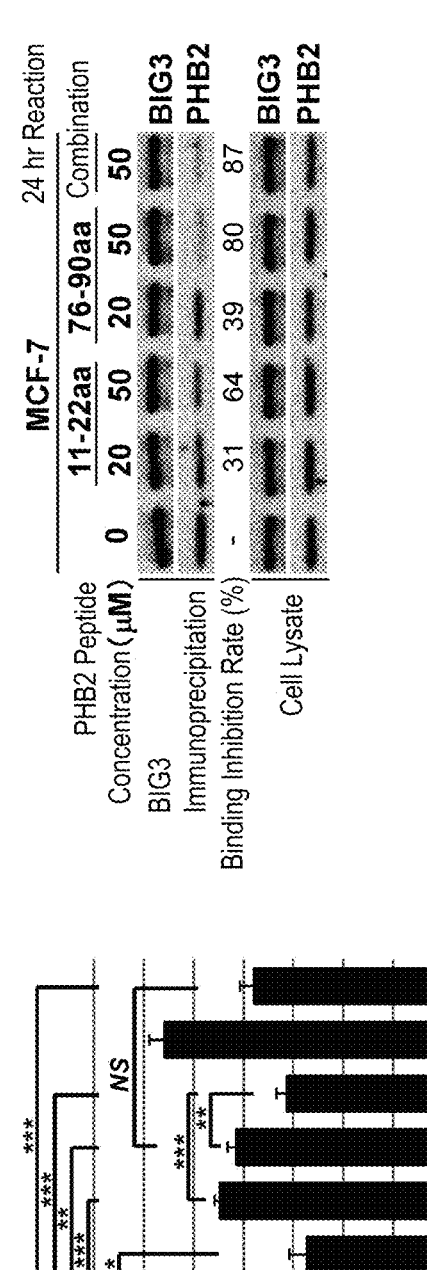
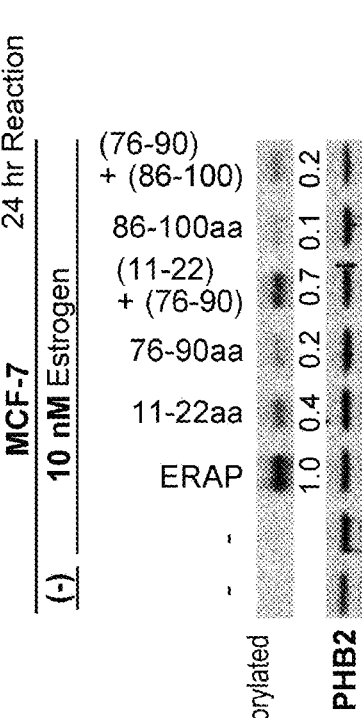

Ac-RLPAGPRGMGTA-(miniPEG)x-QYPIIYDIRARPRKI-RRRRRRRR-NH₂

(SEQ ID NO: 22)

(SEQ ID NO: 23)

Ac-RLPAGPRGMGTA-(miniPEG)x-NH (SEQ ID NO: 22)

Ac-QYPIIYDIRARPRK-RRRRRRRR-NH₂

(SEQ ID NO: 24)

(SEQ ID NO: 25)

(SEQ ID NO: 26)

miniPEG

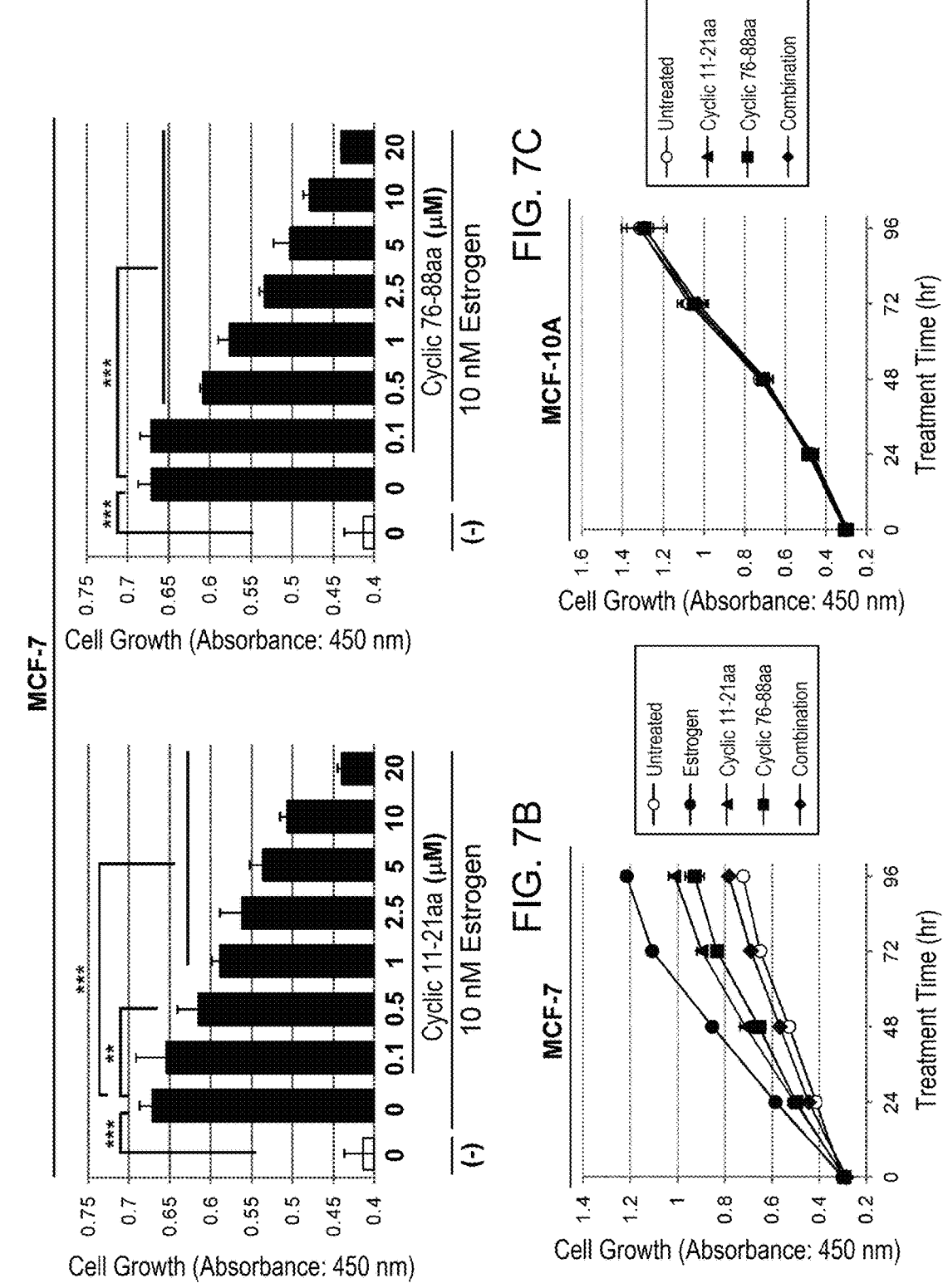

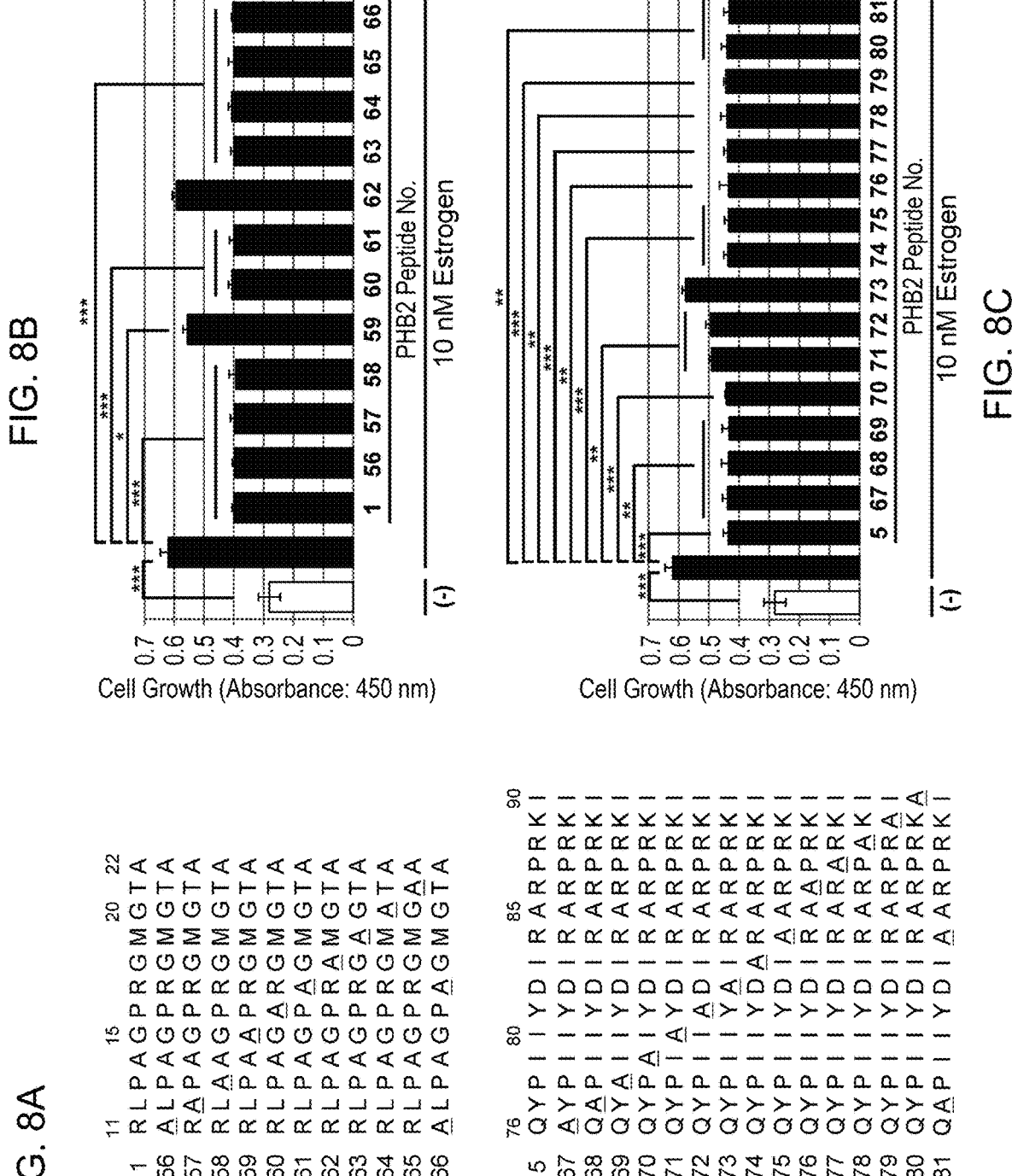

Cell Growth (Absorbance: 450 nm)

PHB2 Peptide No.

10 nM Estrogen

| | 38 | 40 | | 45 | | 50 | | 55 | 57 |
|---|---|---|---|---|---|---|---|---|---|
| SEQ ID NO: 2 | | | T V E G G H R A I | | | | | |
| SEQ ID NO: 82 | E S V F T V E G G H R A I | | | | | | F F N R I G G | |
| SEQ ID NO: 3 | | | T V E G G H R A I | | | | F F N R I G G | |
| SEQ ID NO: 83 | E S V F T V E G G H R A I | | | | | | F F N R I G G | |

FIG. 9B
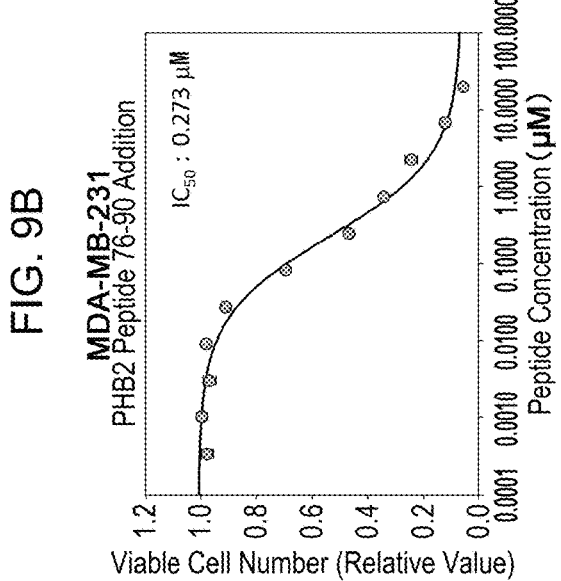
FIG. 9A
FIG. 9C
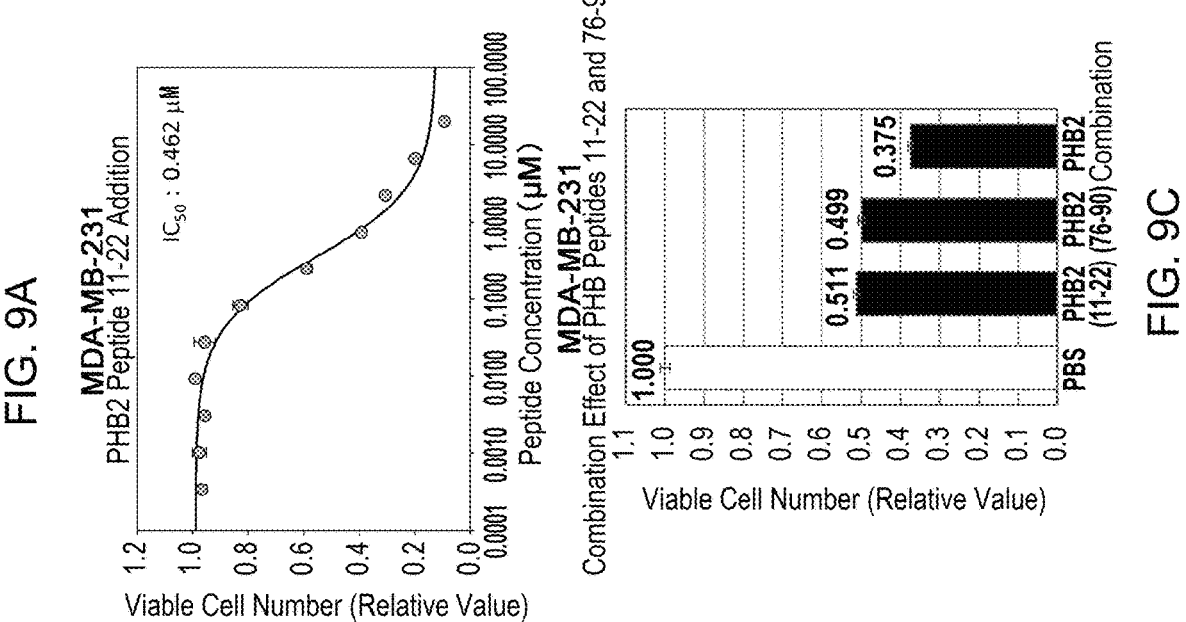

FIG. 10A

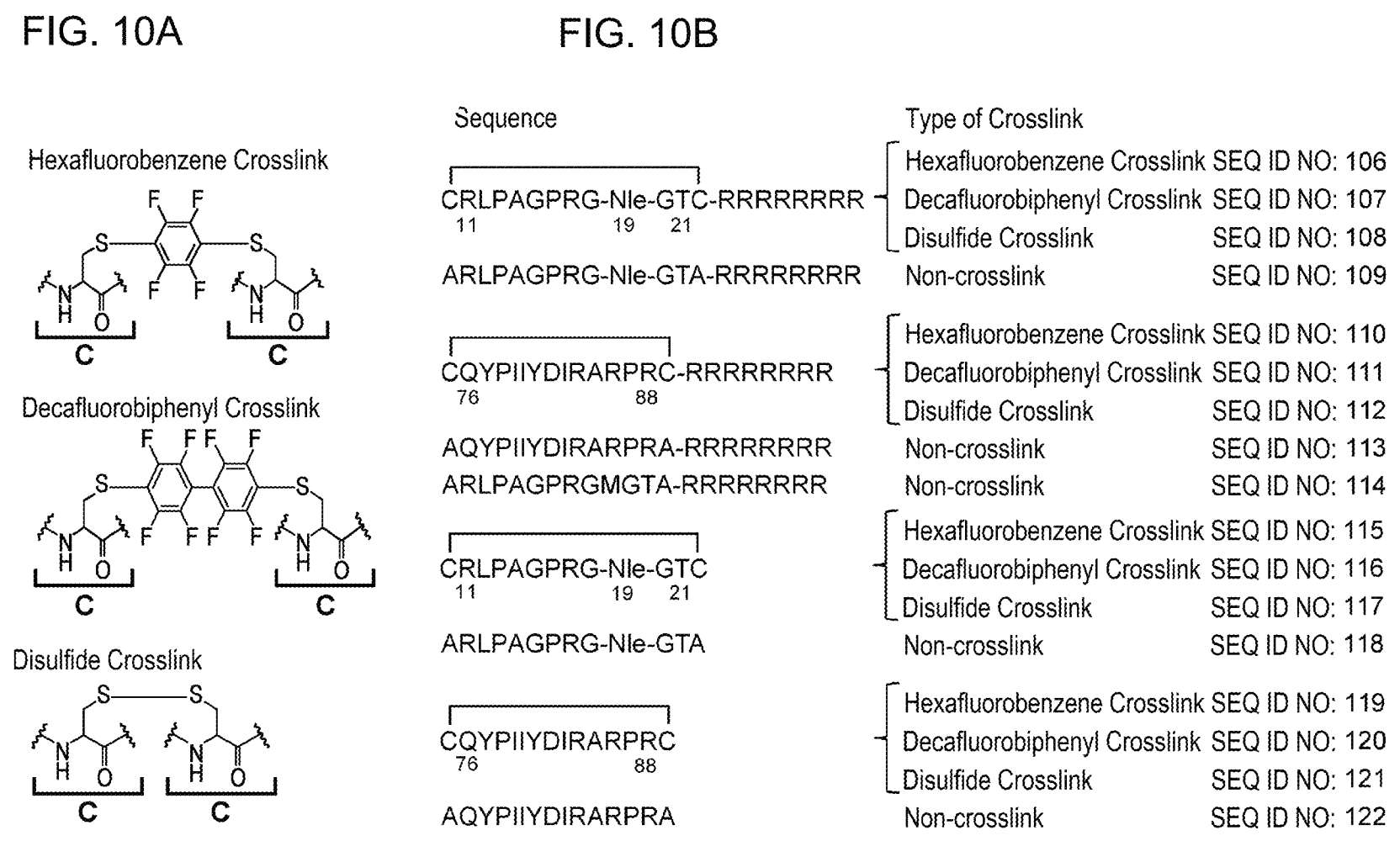

Hexafluorobenzene Crosslink

Decafluorobiphenyl Crosslink

Disulfide Crosslink

FIG. 10B

| Sequence | Type of Crosslink | |
|---|---|---|
| CRLPAGPRG-Nle-GTC-RRRRRRRR (11, 19, 21) | Hexafluorobenzene Crosslink | SEQ ID NO: 106 |
| | Decafluorobiphenyl Crosslink | SEQ ID NO: 107 |
| | Disulfide Crosslink | SEQ ID NO: 108 |
| ARLPAGPRG-Nle-GTA-RRRRRRRR | Non-crosslink | SEQ ID NO: 109 |
| CQYPIIYDIRARPRC-RRRRRRRR (76, 88) | Hexafluorobenzene Crosslink | SEQ ID NO: 110 |
| | Decafluorobiphenyl Crosslink | SEQ ID NO: 111 |
| | Disulfide Crosslink | SEQ ID NO: 112 |
| AQYPIIYDIRARPRA-RRRRRRRR | Non-crosslink | SEQ ID NO: 113 |
| ARLPAGPRGMGTA-RRRRRRRR | Non-crosslink | SEQ ID NO: 114 |
| CRLPAGPRG-Nle-GTC (11, 19, 21) | Hexafluorobenzene Crosslink | SEQ ID NO: 115 |
| | Decafluorobiphenyl Crosslink | SEQ ID NO: 116 |
| | Disulfide Crosslink | SEQ ID NO: 117 |
| ARLPAGPRG-Nle-GTA | Non-crosslink | SEQ ID NO: 118 |
| CQYPIIYDIRARPRC (76, 88) | Hexafluorobenzene Crosslink | SEQ ID NO: 119 |
| | Decafluorobiphenyl Crosslink | SEQ ID NO: 120 |
| | Disulfide Crosslink | SEQ ID NO: 121 |
| AQYPIIYDIRARPRA | Non-crosslink | SEQ ID NO: 122 |

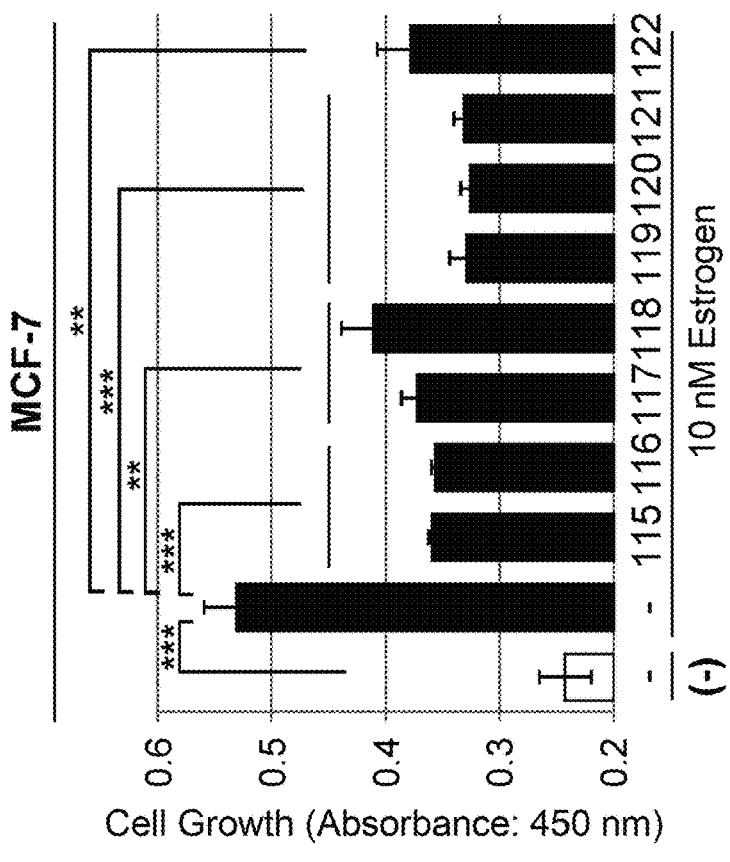
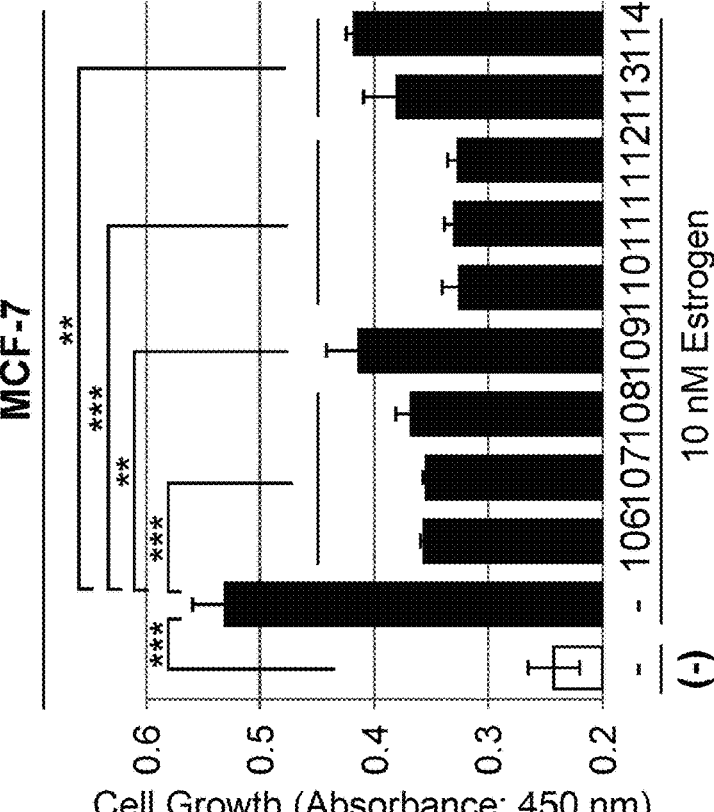
FIG. 10C

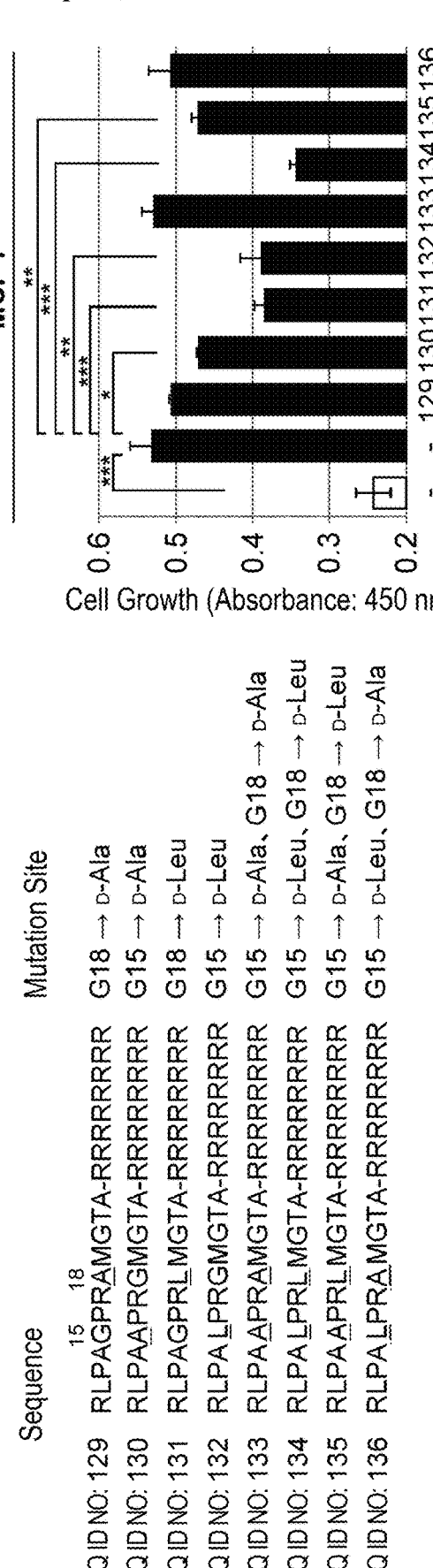

FIG. 12B

| | Sequence | Mutation Site |
|---|---|---|
| | 15   18 | |
| SEQ ID NO: 129 | RLPAGPRAMGTA-RRRRRRRR | G18 → D-Ala |
| SEQ ID NO: 130 | RLPAAPRGMGTA-RRRRRRRR | G15 → D-Ala |
| SEQ ID NO: 131 | RLPAGPRLMGTA-RRRRRRRR | G18 → D-Leu |
| SEQ ID NO: 132 | RLPALPRGMGTA-RRRRRRRR | G15 → D-Leu |
| SEQ ID NO: 133 | RLPAAPRAMGTA-RRRRRRRR | G15 → D-Ala, G18 → D-Ala |
| SEQ ID NO: 134 | RLPALPRLMGTA-RRRRRRRR | G15 → D-Leu, G18 → D-Leu |
| SEQ ID NO: 135 | RLPAAPRLMGTA-RRRRRRRR | G15 → D-Ala, G18 → D-Leu |
| SEQ ID NO: 136 | RLPALPRAMGTA-RRRRRRRR | G15 → D-Leu, G18 → D-Ala |

FIG. 12A

THERAPEUTIC AGENT FOR BREAST CANCER COMPRISING BIG3-PHB2 INTERACTION-INHIBITING PEPTIDE DERIVED FROM PHB2

CROSS-REFERENCE TO RELATED APPLICATIONS

The present application is a § 371 National Phase Application of PCT/JP2019/046505, filed Nov. 28, 2019, which application claims the benefit of Japanese Patent Application No. JP 2018-225660, filed Nov. 30, 2018, the entire contents of which are incorporated by reference in their entireties for all purposes herein.

SEQUENCE LISTING

The instant application contains a Sequence Listing which has been submitted electronically in ASCII format and is hereby incorporated by reference in its entirety. Said ASCII copy, created on Oct. 8, 2019, is named ONC-A1802Psq.txt and is 146 kp in size.

TECHNICAL FIELD

The present invention relates to PHB2-derived peptides that inhibit BIG3-PHB2 interaction and therapeutic agents for breast cancer comprising the peptide.

BACKGROUND ART

Estrogen-receptor α (ERα) plays a key role in the development and progression of breast cancer. The current endocrine therapies for breast cancer mainly target ERα signaling, and use selective ERα modulators (for example, tamoxifen and raloxifene), ERα down-regulators (for example, fulvestrant), and aromatase inhibitors (AI) (NPLs 1 to 3). Among these therapies, a method that uses tamoxifen, which inhibits breast cancer cell proliferation through competitive binding to ERα, is a standard therapy for patients with ERα-positive breast cancer. However, tamoxifen therapy is often ineffective, and the patient may die from recurrent endocrine therapy-resistant tumors (NPLs 4 and 5). Furthermore, compared with tamoxifen, AI, which blocks estrogen synthesis, provides substantial clinical effects such as good efficacy, significant increase in relapse-free survival period, and a prolonged time to disease recurrence in postmenopausal women; however, some patients who have undergone AI treatment still relapse (NPLs 6 and 7). The precise molecular events having effects on the efficacy of these endocrine therapies remain unknown.

A complex formed between brefeldin A-inhibited guanine nucleotide-exchange protein 3 (BIG3), which is a cancer specific protein, and prohibition 2 (PHB2), which is a tumor suppressor, plays a key role in estrogen signaling regulation in ERα-positive breast cancer (NPLs 8 and 9). BIG3 binds to PHB2 to inhibit the ability of PHB2, which suppresses the estrogen-dependent transcriptional activation, and thereby causes constitutive ERα activation.

Based on these findings, strategies of making PHB2 exhibit its tumor suppressive activity by dissociating PHB2 from its complex with BIG3 through inhibition of the BIG3-PHB2 interaction, may become a novel therapy for breast cancer. Based on this strategy, the present inventors have previously developed a dominant negative peptide of BIG3, which specifically inhibits the BIG3-PHB2 interaction (PTL 1). This peptide has been confirmed to suppress breast cancer growth by reactivating the tumor suppressive activity of PHB2 to inhibit ERα-signaling pathways that bring about the growth of breast cancer (PTL 1).

CITATION LIST

Patent Literature

[PTL 1] WO 2013/018690

Non-Patent Literature

[NPL 1] Johnston, S. R., Clin. Cancer Res. 16(7), 1979-87 (2010).
[NPL 2] Fisher, B. et al., J. Natl. Cancer Inst. 97(22), 1652-62 (2005).
[NPL 3] Jordan, V. C., Nature Rev. Drug Discov. 2(3), 205-13 (2003).
[NPL 4] Clarke, R. et al., Pharmacol. Rev. 53(1), 25-71 (2001).
[NPL 5] Fisher, B. et al., J. Natl. Cancer Inst. 93(9), 684-90 (2001).
[NPL 6] Chlebowski, R. et al., Breast 2, S1-11 (2009).
[NPL 7] Chumsri, S. et al., J. Steroid Biochem. Mol. Biol. 125(1-2), 13-22 (2011).
[NPL 8] Kim, J. W. et al., Cancer Sci. 100(8), 1468-78 (2009).
[NPL 9] Yoshimaru, T. et al., Nat. Commun. 4, 2443 (2013).
[NPL 10] Yoshimaru, T. et al., Sci Rep. 7(1), 1821 (2017).

SUMMARY OF INVENTION

Technical Problem

As noted above, it has been elucidated that an estrogen receptor (ER) activation regulator, BIG3, interacts with a suppressor, PHB2, to cause constitutive activation of ER and that a BIG3-PHB2 interaction-targeting inhibitory peptide (ERAP; the amino acid sequence at positions 165 to 177 (QMLSDLTLQLRQR; SEQ ID NO: 33) of the BIG3 protein) has the effect of suppressing estrogen (E2)-dependent breast cancer cell growth (PTL 1; WO2017/126461). However, although ERAP, derived from the BIG3 sequence, achieves the interaction inhibition by binding to PHB2, it cannot be denied that ERAP exerts non-selective effects in organs other than cancer tissue because PHB2 expression is found in organs throughout the human body.

Accordingly, an objective of the present invention is to provide a therapeutic strategy which targets the BIG3-PHB2 interaction and can be expected to be highly selective for breast cancer.

Solution to Problem

The present inventors designed multiple PHB2-derived peptides (PHB2 peptides) based on the data of candidate protein interaction regions on the PHB2 amino acid sequence predicted through in silico analysis, and used these PHB2 peptides for screening to identify interaction regions using the effect of suppressing cell growth as an indicator. As a result, the present inventors succeeded in finding that PHB2 peptide No. 1 (11-RLPAGPRGMGTA-22 (SEQ ID NO: 1)) and PHB2 peptide No. 5 (76-QYPIIYDIRARPRKI-90 (SEQ ID NO: 5)) each have the effect of suppressing growth by about 50%, and in particular that the combination of PHB2 peptides Nos. 1 and 5 exhibits the effects of suppressing growth by more than 90% and inhibiting the BIG3-PHB2 interaction, as with ERAP. Furthermore, these effects were also observed for peptides consisting of sequences around PHB2 peptides Nos. 1 and 5 and for peptides in which amino acid residues at various positions in PHB2 peptides Nos. 1 and 5 have been substituted.

On the other hand, the cell growth suppressive effect of PHB2 peptides Nos. 1 and 5 was also observed on triple-negative breast cancer cells which do not express estrogen receptors and such but express BIG3. Moreover, the use of these peptides in combination showed enhancement of the effect. It is considered that in triple-negative breast cancer, which proliferates in a manner independent of proliferative signals such as hormones, its growth is activated by the binding between PHB2 and BIG3 without receipt of these signals in cells. It was suggested that the PHB2-derived peptides may suppress cell growth by inhibiting the binding between BIG3 and PHB2 in breast cancer expressing at least BIG3.

The present inventors thus found the PHB2-derived peptides which inhibit the BIG3-PHB2 interaction and exert an antitumor effect on E2-dependent breast cancer and triple-negative breast cancer, and completed the present invention. That is, the present invention provides the following peptides and uses thereof.

[1] A peptide, comprising a site binding to a BIG3 polypeptide in a PHB2 polypeptide, wherein the peptide inhibits the binding between the PHB2 polypeptide and the BIG3 polypeptide.

[2] The peptide of [1], wherein the peptide comprises any one or a combination of all or part of the amino acid sequence consisting of the amino acids at positions 11 to 21; all or part of the amino acid sequence consisting of the amino acids at positions 76 to 88; and all or part of the amino acid sequence consisting of the amino acids at positions 44 to 57, in the amino acid sequence of SEQ ID NO: 28 (full-length PHB2 polypeptide).

[3] A peptide, comprising an amino acid sequence selected from the group consisting of (a) to (f) below, wherein the peptide inhibits the binding between a PHB2 polypeptide and a BIG3 polypeptide:

(a) an amino acid sequence selected from the group consisting of SEQ ID NOs: 1 and 36 to 41 (PHB2 sequence-derived peptides Nos. 1 and 36 to 41);
  (b) an amino acid sequence in which one, two, or several amino acids are substituted, deleted, inserted and/or added in the amino acid sequence selected from the group consisting of SEQ ID NOs: 1 and 36 to 41 (PHB2 sequence-derived peptides Nos. 1 and 36 to 41);
  (c) an amino acid sequence selected from the group consisting of SEQ ID NOs: 5 and 47 to 53 (PHB2 sequence-derived peptides Nos. 5 and 47 to 53);
  (d) an amino acid sequence in which one, two, or several amino acids are substituted, deleted, inserted and/or added in the amino acid sequence selected from the group consisting of SEQ ID NOs: 5 and 47 to 53 (PHB2 sequence-derived peptides Nos. 5 and 47 to 53);
  (e) an amino acid sequence selected from the group consisting of SEQ ID NOs: 82 and 83 (PHB2 sequence-derived peptides Nos. 82 and 83); and
  (f) an amino acid sequence in which one, two, or several amino acids are substituted, deleted, inserted and/or added in the amino acid sequence selected from the group consisting of SEQ ID NOs: 82 and 83 (PHB2 sequence-derived peptides Nos. 82 and 83).

[4] The peptide of [3], wherein the peptide comprises an amino acid sequence selected from the group consisting of (a') and (b') below:

(a') an amino acid sequence in which one, two, or several amino acid residues located at positions other than those corresponding to glycine (Gly/G) at positions 15 and 18 in the amino acid sequence of SEQ ID NO: 28 (full-length PHB2 polypeptide) are substituted with other amino acid residues in an amino acid sequence selected from the group consisting of SEQ ID NOs: 1 and 36 to 41 (PHB2 sequence-derived peptides Nos. 1 and 36 to 41); and
  (b') an amino acid sequence in which one, two, or several amino acid residues located at positions other than that corresponding to aspartic acid (Asp/D) at position 82 in the amino acid sequence of SEQ ID NO: 28 (full-length PHB2 polypeptide) are substituted with other amino acid residues in an amino acid sequence selected from the group consisting of SEQ ID NOs: 5 and 47 to 53 (PHB2 sequence-derived peptides Nos. 5 and 47 to 53).

[5] The peptide of any one of [1] to [4], wherein the peptide consists of 80 amino acid residues or less.

[6] The peptide of any one of [1] to [5], wherein the peptide consists of 25 amino acid residues or less.

[7] The peptide of any one of [1] to [6], wherein the peptide consists of an amino acid sequence selected from the group consisting of SEQ ID NOs: 1, 5, 36 to 41, 47 to 53, 82, and 83 (PHB2 sequence-derived peptides Nos. 1, 5, 36 to 41, 47 to 53, 82, and 83).

[8] The peptide of any one of [1] to [7], wherein the peptide has been modified with a cell membrane-permeable substance.

[9] The peptide of any one of [1] to [8], wherein the peptide is cyclic.

[10] The peptide of any one of [1] to [9], wherein the peptide is cross-linked.

[11] The peptide of any one of [1] to [10], wherein the peptide has either or both of the following properties (i) and (ii):
  (i) suppressing growth of BIG3-positive cells; and
  (ii) promoting phosphorylation of a serine residue in the PHB2 polypeptide in BIG3-positive cells.

[12] A polynucleotide encoding the peptide of any one of [1] to [11].

[13] A pharmaceutical composition comprising: at least one ingredient selected from the group consisting of one or more of the peptides of any one of [1] to [11], a polynucleotide(s) encoding the peptide(s), and a pharmaceutically acceptable salt(s) of the peptide(s); and a pharmaceutically acceptable carrier.

[14] The pharmaceutical composition of [13], wherein the composition comprises any one or a combination of: a peptide comprising all or part of the amino acid sequence consisting of the amino acids at positions 11 to 21 in the amino acid sequence of SEQ ID NO: 28 (full-length PHB2 polypeptide); a peptide comprising all or part of the amino acid sequence consisting of the amino acids at positions 44 to 57 in the amino acid sequence of SEQ ID NO: 28 (full-length PHB2 polypeptide); and a peptide comprising all or part of the amino acid sequence consisting of the amino acids at positions 76 to 88 in the amino acid sequence of SEQ ID NO: 28 (full-length PHB2 polypeptide).

[15] The pharmaceutical composition of [13] or [14], which is for suppressing growth of cancer cells or for treatment and/or prophylaxis (prevention) of cancer.

[16] The pharmaceutical composition of [15], wherein the cancer is BIG3-positive cancer.

[17] The pharmaceutical composition of [15] or [16], wherein the cancer is breast cancer.

[18] The pharmaceutical composition of any one of [15] to [17], wherein the cancer is estrogen receptor-positive cancer.

[19] A method for either or both of treatment and prophylaxis (prevention) of cancer, wherein the method comprises administering to a subject at least one selected from the group consisting of one or more of the peptides of any one of [1] to [11]; a polynucleotide(s) encoding the peptide(s); and a pharmaceutically acceptable salt(s) of the peptide(s).

[20] The method of [19], wherein the method comprises administering any one or a combination of: a peptide comprising all or part of the amino acid sequence consisting of the amino acids at positions 11 to 21 in the amino acid sequence of SEQ ID NO: 28 (full-length PHB2 polypeptide); a peptide comprising all or part of the amino acid sequence consisting of the amino acids at positions 44 to 57 in the amino acid sequence of SEQ ID NO: 28 (full-length PHB2 polypeptide); and a peptide comprising all or part of the amino acid sequence consisting of the amino acids at positions 76 to 88 in the amino acid sequence of SEQ ID NO: 28 (full-length PHB2 polypeptide).

[21] A method for either or both of treatment and prophylaxis (prevention) of pharmacotherapy-resistant breast cancer (for example, triple-negative breast cancer), wherein the method comprises: selecting a patient with pharmacotherapy-resistant breast cancer (for example, a patient with triple-negative breast cancer); and administering to a subject at least one selected from the group consisting of one or more of the peptides of any one of [1] to [11], a polynucleotide(s) encoding the peptide(s), and a pharmaceutically acceptable salt(s) of the peptide(s).

Alternatively, the present invention provides use of at least one selected from the group consisting of one or more of the peptides of any one of [1] to [11] mentioned above, a polynucleotide(s) encoding the peptide(s), and a pharmaceutically acceptable salt(s) of the peptide(s), in the manufacture of a pharmaceutical composition for either or both of treatment and prophylaxis (prevention) of cancer. Furthermore, the present invention relates to at least one selected from the group consisting of one or more of the peptides of any one of [1] to [11] mentioned above, a polynucleotide(s) encoding the peptide(s), and a pharmaceutically acceptable salt(s) of the peptide(s), for use in either or both of treatment and prophylaxis (prevention) of cancer. Moreover, the present invention relates to methods of manufacturing a pharmaceutical composition for either or both of treatment and prophylaxis (prevention) of cancer, the method comprising mixing or compounding with a carrier at least one selected from the group consisting of one or more of the peptides of any one of [1] to [11] mentioned above, a polynucleotide(s) encoding the peptide(s), and a pharmaceutically acceptable salt(s) of the peptide(s).

Advantageous Effects of Invention

The peptides of the present invention have the ability to bind to BIG3, a protein highly expressed specifically in, among others, estrogen receptor-positive cancer, and not to PHB2, of which expression is observed in organs throughout the human body, and can inhibit the BIG3-PHB2 interaction. Thus, the peptides of the present invention can be expected to have high selectivity for estrogen receptor-positive cancer.

Furthermore, the peptides of the present invention exhibit a growth suppressive effect not only on estrogen-dependent breast cancer cells but also on triple-negative breast cancer cells. For triple-negative breast cancer, there has so far been no effective molecular target drug, and treatment with existing anticancer agents having strong side effects has been the only option. On the other hand, the cell growth suppressive effect of the peptides of the present invention was not observed in normal mammary gland epithelial cells which did not express BIG3. These suggest that the peptides of the present invention are useful as therapeutic drugs for BIG3-positive cancer, regardless of whether the cancer is hormone-dependent or not.

BRIEF DESCRIPTION OF DRAWINGS

FIGS. 2A-2C show the effect by combination of PHB2 peptides 11-22aa and 76-90aa on the suppression of estrogen-dependent growth. FIG. 2A: Human breast cancer cell line MCF-7 was treated with 10 μM each of ERAP (positive control), PHB2 peptides 11-22aa, 76-90aa, and 86-100aa (negative control), a combination of 11-22aa and 76-90aa, and a combination of 76-90aa and 86-100aa, and then the cells were immediately stimulated with 10 nM estrogen to evaluate the cell number after 24 hours by MTT assay. The data represents mean±standard deviation of three independent experiments. FIG. 2B: The suppressive effects of PHB2 peptides 11-22aa and 76-90aa and their combination on the interaction between BIG3 and PHB2 in MCF-7 were evaluated by Western blotting. MCF-7 was treated with 20 μM and 50 μM each of PHB2 peptides for 24 hours, and the cells were then lysed and immunoprecipitated with an anti-BIG3 antibody to perform immunoblot analysis using the antibodies shown in the figure. The percent binding inhibition is represented as the ratio when taking the PHB2 band area in untreated cells as 100. FIG. 2C: Human breast cancer cell line MCF-7 was treated with 10 μM each of ERAP, PHB2 peptides 11-22aa, 76-90aa, and 86-100aa, a combination of 11-22aa and 76-90aa, and a combination of 76-90aa and 86-100aa , and then the cells were immediately stimulated with 10 nM estrogen to evaluate the phosphorylation of PHB2 (Ser39) after 24 hours by Western blotting. The strength of phosphorylation is represented as the ratio when taking the phosphorylated band area of ERAP treatment in the presence of estrogen as 1.0.

FIG. 3A: Human breast cancer cell line MCF-7 was treated with PHB2 peptides 11-90aa (10, 20 and 50 μM), 11-22aa (50 μM), and 76-90aa (50 μM), and a combination of 11-22aa and 76-90aa, and then the cells were immediately stimulated with 10 nM estrogen to evaluate the cell number after 24 hours by MTT assay. The data represents mean±standard deviation of three independent experiments. FIG. 3B: The inhibition effects of PHB2 peptides 11-90aa and 10 μM ERAP (positive control) on the interaction between BIG3 and PHB2 in MCF-7 were evaluated by Western blotting. FIG. 3C: Human breast cancer cell line MCF-7 was treated with PHB2 peptide 11-90aa (20, 50, and 100 μM) and 10 μM ERAP, and then the cells were immediately stimulated with 10 nM estrogen to evaluate the phosphorylation of PHB2 (Ser39) after 24 hours by Western blotting. The strength of phosphorylation is represented as the ratio when taking the phosphorylated band area of the untreated cells as 1.0.

FIG. 4A: Linear bound PHB2 peptide. FIG. 4B: Branched PHB2 peptide. FIG. 4C: Cyclic PHB2 peptides.

FIG. 5A: Human breast cancer cell line MCF-7 was treated with 10 μM each of linear peptides 11-22aa and 76-90aa, a combination of linear 11-22aa and 76-90aa, the linear bound peptide, the branched bound peptide, cyclic 11-21aa and cyclic 76-88aa, and a combination of the cyclic peptides, and then the cells were immediately stimulated with 10 nM estrogen to evaluate the cell number after 24 hours by MTT assay. The data represents mean±standard deviation of three independent experiments. FIG. 5B shows the results of MTT assay showing that linear 11-22aa and linear 76-90aa, the linear bound peptide, the branched bound peptide, and cyclic 11-21aa and cyclic 76-88aa peptides have no effect on growth of normal mammary gland epithelial cells, MCF-10A. FIG. 5C: Human breast cancer cell line MCF-7 was treated with 10 μM each of linear peptides 11-22aa and 76-90aa, a combination of linear 11-22aa and 76-90aa, the linear bound peptide, the branched bound peptide, cyclic 11-21aa and cyclic 76-88aa, and a combination of the cyclic peptides, and their suppressive effects on the interaction between BIG3 and PHB2 were evaluated by Western blotting.

FIG. 6A: Human breast cancer cell line MCF-7 was treated with linear 11-22aa and cyclic 11-21aa (left) or with linear 76-90aa and cyclic 76-88aa (right), and then the cells were immediately stimulated with 10 nM estrogen to evaluate the suppressive effect by MTT assay every 24 hours up to 96 hours. FIG. 6B represents the results of MTT assay showing that cyclic 11-21aa and cyclic 76-88aa peptides have no effect on the growth of normal mammary gland epithelial cells, MCF-10A. The data represents mean±standard deviation of three independent experiments.

FIGS. 7A-7C show the concentration-dependent suppressive effects of cyclic PHB2 peptides on estrogen-dependent growth. FIG. 7A: Human breast cancer cell line MCF-7 was treated with 0.1, 0.5, 1, 2.5, 5, 10, and 20 μM each of cyclic 11-21aa and 76-88aa, and then the cells were immediately stimulated with 10 nM estrogen to evaluate the cell number after 24 hours by MTT assay. The data represents mean±standard deviation of three independent experiments. FIG. 7B: Human breast cancer cell line MCF-7 was treated with cyclic 11-21aa (4 μM), cyclic 76-88aa (2 μM), and their combination, and then the cells were immediately stimulated with 10 nM estrogen to evaluate the suppressive effect by MTT assay every 24 hours up to 96 hours. The data represents mean±standard deviation of three independent experiments. FIG. 7C represents the results of MTT assay showing that cyclic 11-21aa (4 μM), cyclic 76-88aa (2 μM), and their combination have no effect on growth of normal mammary gland epithelial cells, MCF-10A.

FIGS. 8A-C: PHB2 amino acids important for suppressing estrogen-dependent growth are shown. FIG. 8A depicts alanine-mutated PHB2 peptides of No. 1 (11-22aa) and No. 5 (76-90aa). FIGS. 8B, 8C: Human breast cancer cell line MCF-7 was treated with 10 μM each of the alanine-mutated peptides derived from PHB2 sequence, and then the cells were immediately stimulated with 10 nM estrogen to evaluate the cell number for 24 hours by MTT assay. The data represents mean±standard deviation of three independent experiments.

FIGA. 0A-9C show the cell growth suppressive effects of PHB2 peptides 11-22aa (FIG. 9A) and 76-90aa (FIG. 9B) on triple-negative breast cancer cells. Each peptide was diluted in a 3-fold dilution series starting from 20 μM with total 11 concentrations and added to breast cancer cell line MDA-MB-231. The numbers of viable cells were measured 96 hours after the peptide addition, the relative values were calculated based on negative control cells to which no peptide was added, and the values were plotted on the graph. The data represents mean±standard deviation of three independent experiments. FIG. 9C shows the results of examining the combined effect of PHB2 peptides 11-22aa and 76-90aa on cell growth of MDA-MB-231. The peptides were added to the cells alone or in combination at $IC_{50}$ value, the numbers of viable cells were measured after 96 hours, the relative values were calculated based on negative control cells to which phosphate buffered saline (PBS) was added, and the values were plotted on the graph. The data represents mean±standard deviation of three independent experiments.

FIGS. 10A-10B: the suppressive effects of cross-linked PHB2 peptides on estrogen-dependent growth are shown. FIG. 10A shows schemes of cross-linking forms. FIG. 10B shows PHB2 peptides prepared by adding cysteine to both ends of PHB2 peptides 11-21aa and 76-88aa and cross-linking them (SEQ ID NOs: 106 to 108, 110 to 112, 115 to 117, and 119 to 121). The PHB2 peptides of SEQ ID NOs: 109, 113, 114, 118, and 122 were prepared as non-cross-linked peptides by adding alanine to both ends. The PHB2 peptides of SEQ ID NOs: 106 to 114 were prepared by adding polyarginine to the C terminus. Furthermore, in the PHB2 peptides of 11-21aa, methionine at position 19 in the amino acid sequence of SEQ ID NO: 28 (full-length PHB2 polypeptide) was substituted with norleucine (Nle) to avoid oxidation during synthesis.

FIG. 10C: Human breast cancer cell line MCF-7 was treated with cross-linked PHB2 peptides of 11-21aa (left panel) or with cross-linked PHB2 peptides of 76-88aa (right panel), and then the cells were immediately stimulated with 10 nM estrogen to evaluate the cell number after 24 hours by MTT assay. The data represents mean±standard deviation of three independent experiments.

Figure 11A:
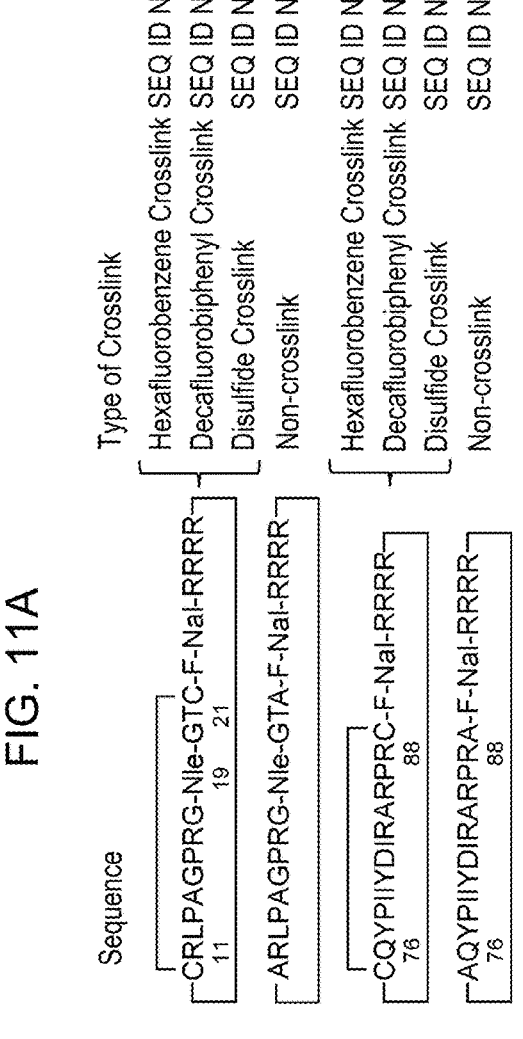
Figure 11B:
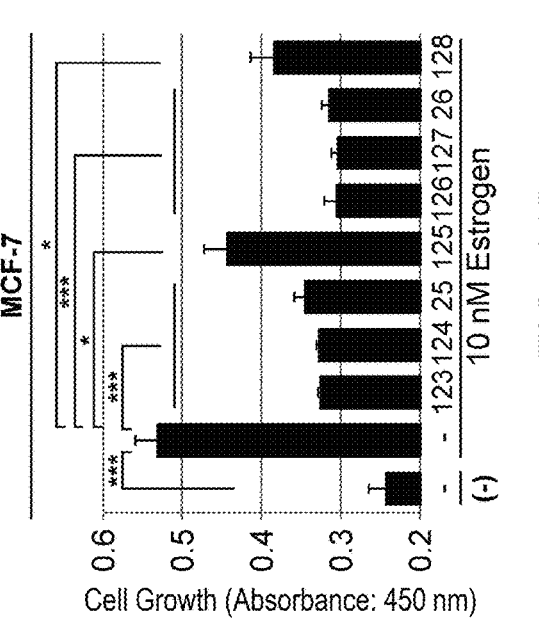

FIGS. 11A-11B show the suppressive effects of cyclic PHB2 peptides on estrogen-dependent growth. FIG. 11A depicts cross-linking types of PHB2 peptides of cyclic 11-21aa (SEQ ID NO: 25) and cyclic 76-88aa (SEQ ID NO: 26). The cyclic PHB2 peptides of SEQ ID NOs: 125 and 128 were prepared as non-cross-linked cyclic peptides by adding alanine to both ends of PHB peptides 11-21aa and 76-88aa. All cyclic PHB2 peptides were prepared by adding an unnatural amino acid and consecutive multiple arginine residues to the C terminus. Furthermore, in the cyclic PHB2 peptides of 11-21aa, methionine at position 19 in the amino acid sequence of SEQ ID NO: 28 (full-length PHB2 polypeptide) was substituted with norleucine (Nle) to avoid oxidation during synthesis. FIG. 11B: Human breast cancer cell line MCF-7 was treated with cyclic PHB2 peptides, and then the cells were immediately stimulated with 10 nM estrogen to evaluate the cell number after 24 hours by MTT assay. The data represents mean±standard deviation of three independent experiments.

FIGS. 12A-12B show the effects of modifications of PHB2 peptide 11-22aa on estrogen-dependent growth. FIG. 12A depicts PHB2 peptides prepared from the PHB2 peptide of SEQ ID NO: 1 (11-22aa) by substituting glycine at positions 15 and 18 in the amino acid sequence of SEQ ID NO: 28 (full-length PHB2 polypeptide) with D-alanine and D-leucine. FIG. 12B: Human breast cancer cell line MCF-7 was treated with the modified PHB2 peptides of 11-22aa, and then the cells were immediately stimulated with 10 nM estrogen to evaluate the cell number after 24 hours by MTT assay. The data represents mean±standard deviation of three independent experiments.

Figure 13:
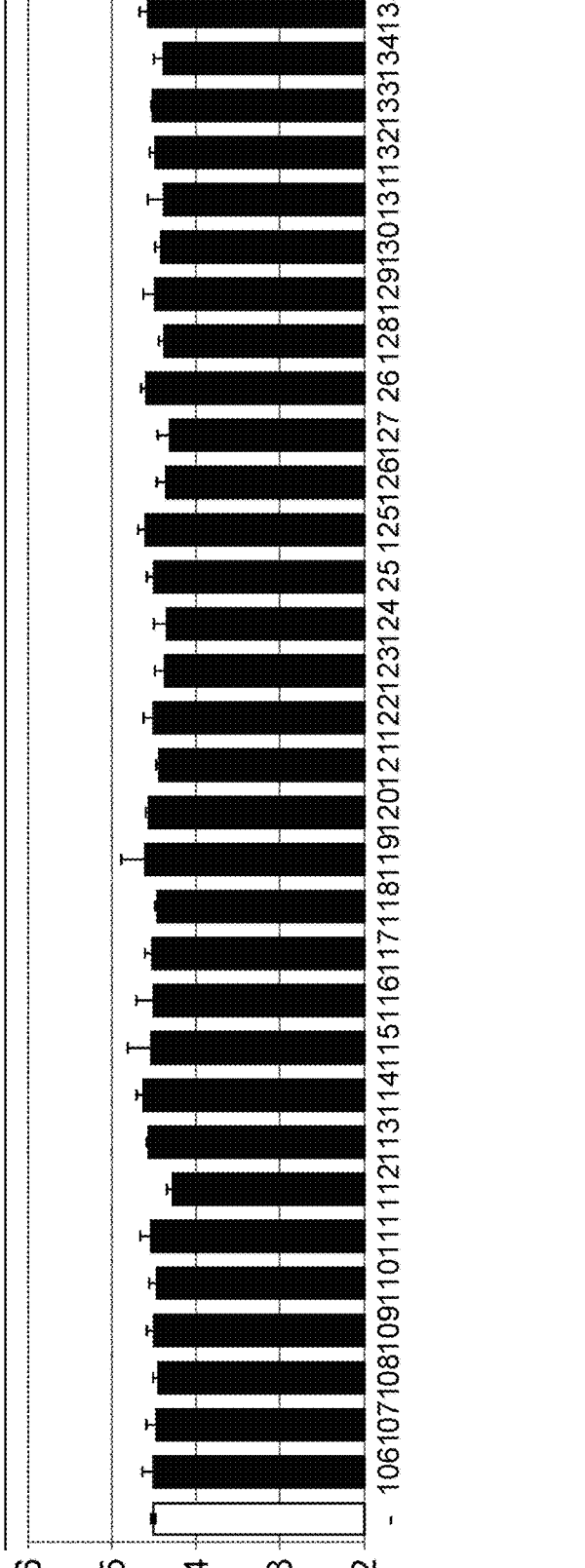

FIG. 13 shows the effects of cross-linked PHB2 peptides on normal mammary gland epithelial cells, MCF-10A. The figure represents the results of MTT assay showing that cross-linked PHB2 peptides and cyclic PHB2 peptides have no effect on growth of normal mammary gland epithelial cells, MCF-10A. The data represents mean±standard deviation of three independent experiments.

DESCRIPTION OF EMBODIMENTS

Although any methods and materials similar or equivalent to those described herein can be used in the practice or testing of embodiments of the present invention, the preferred methods, devices, and materials are now described. However, before the present materials and methods are described, it is to be understood that the present invention is not limited to the particular sizes, shapes, dimensions, materials, methodologies, protocols, etc. described herein, as these may vary in accordance with routine experimentation and optimization. It is also to be understood that the terminology used in the description is for the purpose of describing the particular versions or embodiments only, and is not intended to limit the scope of the present invention which will be limited only by the appended claims.

Definitions

The words "a", "an", and "the" used herein mean "at least one" unless otherwise specifically indicated.

Herein, unless otherwise specifically indicated, amino acids represented by capital letters indicate L-amino acids. Amino acids represented by lower-case letters indicate D-amino acids. Furthermore, L-amino acids and D-amino acids represented herein may include amino acids in which any of amino group, carboxyl group, and side chains has been modified. Examples of preferred modifications include acetylation of the amino group, amidation of the carboxyl group, tag peptide addition such as FLAG-tagging and HA-tagging, and such.

Herein, numbers indicating the positions of amino acid residues in amino acid sequences have been given with the N-terminal amino acid residue as number 1 and in order toward the C terminus, unless otherwise specifically indicated.

The term "BIG3" used herein refers to brefeldin A-inhibited guanine nucleotide-exchange protein 3. BIG3 forms a complex with PHB2 to inhibit the estrogen-dependent transcriptional activation-suppressing function of PHB2. BIG3 is also referred to as "ARFGEF family member 3 (ARFGEF3)" or "A7322". An example of a representative nucleotide sequence of the human BIG3 gene is shown in SEQ ID NO: 31 (GenBank Accession No. NM_020340.4), and the amino acid sequence encoded by the gene is shown in SEQ ID NO: 32. In the present invention, BIG3 is not limited to that encoded by the aforementioned nucleotide sequence and also encompasses their isoforms and mutants.

The term "PHB2" used herein refers to prohibitin 2. PHB2 binds to estrogen receptors to inhibit estrogen receptor signaling pathways and suppresses estrogen-dependent cell growth. PHB2 is also referred to as "Repressor of Estrogen Activity (REA)". Examples of representative nucleotide sequences of the human PHB2 gene are shown in SEQ ID NO: 27 (GenBank Accession No. NM_001144831.1) and SEQ ID NO: 29 (GenBank Accession No. NM_001267700.1), and the amino acid sequences encoded by the genes are shown in SEQ ID NO: 28 and SEQ ID NO: 30, respectively. In the present invention, PHB2s are not limited to those encoded by the aforementioned nucleotide sequences and also encompass their isoforms and mutants.

The term "estrogen receptor" used herein encompasses both estrogen receptor α (ERα) and estrogen receptor β (ERβ). ERα and ERβ are encoded by the ESR1 gene and ESR2 gene, respectively. The nucleotide sequence of a representative human ESR1 gene and the amino acid sequence of a representative human ERα are shown in SEQ ID NO: 86 (GenBank Accession No. NM_000125.3) and SEQ ID NO: 87 (GenBank Accession No. NP_000116.2), respectively. Furthermore, the nucleotide sequence of a representative human ESR2 gene and the amino acid sequence of a representative human ERβ are shown in SEQ ID NO: 88 (GenBank Accession No. NM_001437.2) and SEQ ID NO: 89 (GenBank Accession No. NP_001428.1), respectively. In the present invention, however, the nucleotide sequences and amino acid sequences of estrogen receptor are not limited thereto and also encompass their isoforms and mutants. In a preferred embodiment, the estrogen receptor is ERα. It has been reported that transcriptional activation of ERα and ERβ is both regulated by a PHB2 poly-peptide (Montano M M, et al., Proc Natl Acad Sci USA. 96(12): 6947-52 (1999)).

Herein, the term "estrogen receptor-positive" used in the context of a cell or a cancer means that a cell or a cancer cell constituting cancer expresses an estrogen receptor. Whether a cell or cancer is estrogen receptor-positive or not can be confirmed by a known method such as ELISA and immu-nohistochemical staining. Furthermore, herein, the term "estrogen receptor-negative" used in the context of a cell or cancer means that a cell or a cancer cell constituting cancer does not express an estrogen receptor.

The term "ERAP" used herein refers to a peptide con-sisting of the amino acid sequence of SEQ ID NO: 33. The amino acid sequence of SEQ ID NO: 33 is a sequence consisting of the 165th to 177th amino acid residues in the amino acid sequence of BIG3 (SEQ ID NO: 32), and contains amino acid residues important for binding with PHB2 (glutamine (Q) at position 165, aspartic acid (D) at position 169, and glutamine (Q) at position 173 in the amino acid sequence of SEQ ID NO: 32). ERAP has an ability to bind to PHB2 and inhibits BIG3 from forming the complex with PHB2 by binding competitively to PHB2.

The term "treatment" used herein encompasses allevia-tion/improvement of at least one symptom caused by a target disease, suppression of progression of the disease, suppres-sion of enlargement of the disease site, and such. For example, "cancer treatment (treatment of cancer)" includes cancer cell growth suppression, suppression of cancer pro-gression, induction of regression/remission of cancer, alle-viation/improvement of symptoms accompanying cancer, suppression of cancer metastasis, suppression of postopera-tive recurrence, and induction of prolonged survival time.

1. PHB2 Peptides

The present invention provides peptides comprising a site binding to a BIG3 polypeptide (a BIG3 polypeptide-binding site) in a PHB2 polypeptide, which inhibit the binding between the PHB2 polypeptide and the BIG3 polypeptide. The peptides of the present invention are also herein referred to as "PHB2 peptides", "PHB2-derived peptides", or "PHB2 sequence-derived peptides".

The peptides of the present invention have the ability to bind to a BIG3 polypeptide by comprising the BIG3 poly-peptide-binding site in a PHB2 polypeptide. Consequently, the peptides competitively inhibit the binding of the PHB2 polypeptide to the BIG3 polypeptide. The PHB2 peptides of the present invention can be salts as long as they have the effect of inhibiting the binding between a PHB2 polypeptide and a BIG3 polypeptide. For example, the PHB2 peptides can be salts with acids (such as inorganic acids and organic acids) or with bases (such as alkaline metals, alkaline earth metals, and amines). The salts with acids include, for example, salts with inorganic acids (for example, hydro-chloric acid, phosphoric acid, hydrobromic acid, sulfuric acid, and acetic acid) and those with organic acids (for example, acetic acid, formic acid, propionic acid, fumaric acid, maleic acid, succinic acid, tartaric acid, citric acid, malic acid, oxalic acid, benzoic acid, methanesulfonic acid, benzenesulfonic acid, and meglumine acid). The salts with bases include, for example, salts with sodium, potassium, calcium, and ammonium. Preferred examples of salts of the peptides of the present invention include acetates, hydro-chlorides, meglumine salts, and ammonium salts.

The "site binding to a BIG3 polypeptide in a PHB2 polypeptide (BIG3 polypeptide-binding site in a PHB2 polypeptide)" means an amino acid residue(s) involved in binding to a BIG3 polypeptide in the amino acid sequence constituting a PHB2 polypeptide. Such an amino acid resi-due(s) includes, for example, glycine at positions 15 and 18 and aspartic acid at position 82 in the amino acid sequence of SEQ ID NO: 28 (full-length PHB2 polypeptide). Thus, in a preferred embodiment, the peptides of the present inven-tion are peptides which comprise glycine at positions 15 and 18 and aspartic acid at position 82 in the amino acid sequence of SEQ ID NO: 28 (full-length PHB2 polypeptide) and inhibit the binding between a PHB2 polypeptide and a BIG3 polypeptide. Herein, the number of a particular amino acid residue in an amino acid sequence indicates the number of the amino acid residue counted from the N terminus.

Examples of amino acid sequences comprising the BIG3 polypeptide-binding site in a PHB2 polypeptide include (a) all or part of the amino acid sequence consisting of the amino acids at positions 11 to 21 (SEQ ID NO: 84), (b) all or part of the amino acid sequence consisting of the amino acids at positions 76 to 88 (SEQ ID NO: 85), and (c) all or part of the amino acid sequence (SEQ ID NO: 82) consisting of the amino acids at positions 44 to 57, in the amino acid sequence of SEQ ID NO: 28 (full-length PHB2 polypep-tide). Accordingly, preferred examples of the peptides of the present invention include a peptide comprising an amino acid sequence selected from the group consisting of:

(a) an amino acid sequence selected from the group consisting of SEQ ID NOs: 1 and 36 to 41 (PHB2 sequence-derived peptides Nos. 1 and 36 to 41);

(b) an amino acid sequence selected from the group consisting of SEQ ID NOs: 5 and 47 to 53 (PHB2 sequence-derived peptides Nos. 5 and 47 to 53); and (c) an amino acid sequence selected from the group consisting of SEQ ID NOs: 82 and 83 (PHB2 sequence-derived peptides Nos. 82 and 83).

However, the peptides of the present invention are not limited thereto, and the amino acid sequences constituting the peptides are not particularly limited as long as the peptides comprise the BIG3 polypeptide-binding site in a PHB2 polypeptide and have the activity to inhibit the binding between the PHB2 polypeptide and a BIG3 poly-peptide.

In general, it is known that one or more amino acid modifications in a peptide have no effect on the function of the peptide. Indeed, it is known that a peptide having an amino acid sequence in which one or more amino acid residues are modified by substitution, deletion, insertion, and/or addition retains the biological activity of the original peptide (Mark et al., Proc Natl Acad Sci USA 81(18): 5662-6 (1984); Zoller and Smith, Nucleic Acids Res 10(20): 6487-500 (1982); and Dalbadie-McFarland et al., Proc Natl Acad Sci USA 79(21): 6409-13 (1982)). The peptides of the present invention may comprise a substitution or deletion of amino acid residues, for example, at positions other than the BIG3 polypeptide-binding site, in a PHB2-derived amino acid sequence and may have an insertion or addition of amino acid residues at positions which have no effect on the binding to a BIG3 polypeptide, as long as they comprise the BIG3 polypeptide-binding site in a PHB2 polypeptide and have the activity to inhibit the binding between the PHB2 polypeptide and the BIG3 polypeptide. Actually, it is shown in Examples of the present specification that peptides having an amino acid sequence in which an amino acid residue(s) other than the BIG3 polypeptide-binding site in a PHB2 polypeptide has/have been substituted with other amino acid residue(s) also retain the biological activity equal to that of peptides which do not have such substitutions. Accordingly, the peptides of the present invention encompass peptides which comprise an amino acid sequence selected from the group consisting of (a') and (b') below and have an activity to inhibit the binding between a PHB2 polypeptide and a BIG3 polypeptide:

(a') an amino acid sequence in which one, two, or several amino acid residues located at positions other than those corresponding to glycine at positions 15 and 18 in the amino acid sequence of SEQ ID NO: 28 (full-length PHB2 polypeptide) are substituted with other amino acid residues, in an amino acid sequence selected from the group consisting of SEQ ID NOs: 1 and 36 to 41 (PHB2 sequence-derived peptides Nos. 1 and 36 to 41); and (b') an amino acid sequence in which one, two, or several amino acid residues located at positions other than that corresponding to aspartic acid at position 82 in the amino acid sequence of SEQ ID NO: 28 (full-length PHB2 polypeptide) are substituted with other amino acid residues, in an amino acid sequence selected from the group consisting of SEQ ID NOs: 5 and 47 to 53 (PHB2 sequence-derived peptides Nos. 5 and 47 to 53).

In the above (a') and (b'), amino acid residues substituted can be any amino acid residues as long as the resulting peptide maintains the ability to inhibit the binding between a PHB2 polypeptide and a BIG3 polypeptide. Furthermore, which amino acid residue is substituted can be determined by predicting amino acid residues not involved in the binding to a BIG3 polypeptide by using, for example, a calculation method such as PSIVER. The number of amino acid residues substituted are also not particularly limited as long as the resulting peptide maintains the ability to inhibit the binding between a PHB2 polypeptide and a BIG3 polypeptide, and one, two, or several amino acid residues can be substituted. "Several" preferably refers to six, five, four, or three.

In general, it is recognized that a substitution with another amino acid residue which conserves the amino acid side chain characteristics of the original amino acid residue tends to have no effect on the function of the original peptide. Such a substitution is often called a "conservative substitution" or "conservative modification". Accordingly, the substitutions in the above (a') and (b') are preferably performed by conservative substitutions.

Tables of conservative substitutions presenting functionally similar amino acids are well known in the art. Examples of amino acid side chain characteristics that are desirable to conserve include, for example, hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). In addition, the following eight groups each contain amino acids that are accepted in the art as conservative substitutions for one another:

1) Alanine (A), Glycine (G);
  2) Aspartic acid (D), Glutamic acid (E);
  3) Asparagine (N), Glutamine (Q);
  4) Arginine (R), Lysine (K);
  5) Isoleucine (I), Leucine (L), Methionine (M), Valine (V);
  6) Phenylalanine (F), Tyrosine (Y), Tryptophan (W);
  7) Serine (S), Threonine (T); and
  8) Cysteine (C), Methionine (M) (see, e.g., Creighton, Proteins 1984).

However, the substitutions in the above-mentioned (a') and (b') are not limited thereto, and they may be non-conservative substitutions as long as the peptides maintain the activity to inhibit the binding between a PHB2 polypeptide and a BIG3 polypeptide.

The peptides of the present invention can comprise amino acid residues other than the BIG3 polypeptide-binding site in a PHB2 polypeptide as long as they maintain the activity to inhibit the binding between a PHB2 polypeptide and a BIG3 polypeptide. For example, a fragment of PHB2 polypeptide comprising the BIG3 polypeptide-binding site in a PHB2 polypeptide is preferred as a peptide of the present invention. Accordingly, preferred examples of the peptides of the present invention include PHB2 polypeptides (SEQ ID NOs: 1 and 36 to 41 (PHB2 sequence-derived peptides Nos. 1 and 36 to 41)) comprising glycine at positions 15 and 18 and their surrounding sequence in the amino acid sequence of SEQ ID NO: 28 (full-length PHB2 polypeptide) and PHB2 polypeptides (SEQ ID NOs: 5 and 47 to 53 (PHB2 sequence-derived peptides Nos. 5 and 47 to 53)) comprising aspartic acid at position 82 and its surrounding sequence in the amino acid sequence of SEQ ID NO: 28 (full-length PHB2 polypeptide). Other preferred examples of the peptides of the present invention include PHB2 polypeptides (SEQ ID NOs: 82 and 83 (PHB2 sequence-derived peptides Nos. 82 and 83)) comprising amino acids at positions 44 to 57 and their surrounding sequence in the amino acid sequence of SEQ ID NO: 28 (full-length PHB2 polypeptide).

The following peptides can be exemplified as the PHB2 peptides of the present invention: peptides comprising amino acid sequences of SEQ ID NOs: 1, 5, 36 to 41, 47 to 53, 82, and 83 (PHB2 sequence-derived peptides Nos. 1, 5, 36 to 41, 47 to 53, 82, and 83), which peptides are composed of, for example, 30 amino acid residues or 20 amino acid residues, typically 19 amino acid residues, preferably 18 amino acid residues, and more preferably 17 amino acid residues or less. The following peptides can be shown as such peptides: peptides comprising an amino acid sequence selected from the amino acid sequences (9 residues) of SEQ ID NOs: 1, 5, 36 to 41, 47 to 53, 82, and 83 (PHB2 sequence-derived peptides Nos. 1, 5, 36 to 41, 47 to 53, 82, and 83) and an amino acid sequence selected from the full-length amino acid sequence constituting a PHB2 polypeptide, which peptides are composed of 30 amino acid residues or 20 amino acid residues, typically 19 amino acid residues, preferably 18 amino acid residues, and more preferably 17 amino acid residues or less.

In a preferred embodiment of the present invention, an amino acid to be added to the amino acid sequences of SEQ ID NOs: 1, 5, 36 to 41, 47 to 53, 82, and 83 (PHB2 sequence-derived peptides Nos. 1, 5, 36 to 41, 47 to 53, 82, and 83) can be zero (that is, the amino acid sequences consisting of SEQ ID NOs: 1, 5, 36 to 41, 47 to 53, 82, and 83 (PHB2 sequence-derived peptides Nos. 1, 5, 36 to 41, 47 to 53, 82, and 83)) or can be one, two or more consecutive amino acid sequences selected from the full-length amino acid sequence constituting a PHB2 polypeptide (SEQ ID NO: 28 (full-length PHB2 polypeptide)). The amino acid sequences of SEQ ID NOs: 1, 5, 36 to 41, 47 to 53, 82, and 83 (PHB2 sequence-derived peptides Nos. 1, 5, 36 to 41, 47 to 53, 82, and 83) are those comprising glycine at position 15, glycine at position 18, aspartic acid at position 82, or the amino acid sequence consisting of the amino acids at positions 44 to 57 in the full-length amino acid sequence constituting a PHB2 polypeptide (SEQ ID NO: 28 (full-length PHB2 polypeptide)). Accordingly, in a preferred embodiment of the present invention, an amino acid residue or amino acid sequence to be added to SEQ ID NOs: 1, 5, 36 to 41, 47 to 53, 82, and 83 (PHB2 sequence-derived peptides Nos. 1, 5, 36 to 41, 47 to 53, 82, and 83) can be selected from amino acid sequences neighboring glycine at position 15, glycine at position 18, aspartic acid at position 82, or the amino acid sequence consisting of the amino acids at positions 44 to 57 in the amino acid sequence of SEQ ID NO: 28 (full-length PHB2 polypeptide)).

It is desirable that the peptides of the present invention have either or both of the following properties (i) and (ii), in addition to the activity to inhibit the binding between a PHB2 polypeptide and a BIG3 polypeptide:

(i) promoting the nuclear import of a PHB2 polypeptide in an estrogen receptor-positive cell which expresses a BIG3 polypeptide; and (ii) promoting the binding between an estrogen receptor present in the nucleus and/or on cell membrane to a PHB2 polypeptide in an estrogen receptor-positive cell which expresses a BIG3 polypeptide.

By having either or both of the above properties (i) and (ii), the peptides of the present invention suppress activation of estrogen receptors in BIG3-expressing cells, thereby leading to suppression of growth of estrogen receptor-positive cells. Both the above properties (i) and (ii) of PHB2 peptides can be evaluated according to methods known to one skilled in the art.

A PHB2 polypeptide is known as an estrogen receptor-selective coregulator and suppresses transcriptional activation of estrogen receptors by interaction with them (Kasashima K, J Biol Chem 281(47): 36401-10 (2006)). On the other hand, a BIG3 polypeptide binds to a PHB2 polypeptide to block the nuclear import of a PHB2 polypeptide, thereby inhibiting the interaction between the PHB2 polypeptide and an estrogen receptor in the nucleus. Furthermore, a BIG3 polypeptide blocks the binding between an estrogen receptor present on the cell membrane and a PHB2 polypeptide. As a result of these functions, in cells overexpressing a BIG3 polypeptide, suppression of estrogen receptor activation by the PHB2 polypeptide does not sufficiently work, and enhanced cell growth is induced.

The peptides of the present invention have the feature of restoring the PHB2 polypeptide's function of suppressing activation of estrogen receptors, the function having been inhibited by the binding to a BIG3 polypeptide, by competitively inhibiting the binding between the BIG3 polypeptide and the PHB2 polypeptide. On the other hand, a PHB2 polypeptide suppresses activation of estrogen receptors through the binding to them. Accordingly, it is desirable that the peptides of the present invention suppress the binding between a BIG3 polypeptide and a PHB2 polypeptide but do not block the binding between an estrogen receptor and the PHB2 polypeptide, and thus do not block the suppression of estrogen receptor activation by the PHB2 polypeptide. As described above, a fragment of PHB2 polypeptide comprising the BIG3 polypeptide-binding site is suitable as a peptide of the present invention; however, a peptide close to the full-length of a PHB2 polypeptide is likely to block the binding between an endogenous PHB2 polypeptide and an estrogen receptor, thereby blocking the suppression of estrogen receptor activation by the endogenous PHB2 polypeptide. Thus, a partial amino acid sequence of PHB2 polypeptide comprised in the peptides of the present invention is preferably 100 residues or less, more preferably 80 residues or less, and even more preferably 70 residues or less. In a more preferred embodiment, a partial amino acid sequence of PHB2 polypeptide comprised in the peptides of the present invention is 50 residues or less, 40 residues or less, 30 residues or less, 25 residues or less, or 20 residues or less. Since the estrogen receptor-binding site in PHB2 is a site consisting of the amino acids at positions 175 to 198 in the amino acid sequence of SEQ ID NO: 28 (full-length PHB2 polypeptide), the peptides of the present invention preferably do not comprise this site and in this case, a partial amino acid sequence of PHB2 polypeptide comprised in the peptides of the present invention is desirably 100 residues or less, more preferably 80 residues or less, and even more preferably 70 residues or less, excluding the sequence of amino acids at positions 175 to 198. In a more preferred embodiment, a partial amino acid sequence of PHB2 polypeptide comprised in the peptides of the present invention is 50 residues or less, 40 residues or less, 30 residues or less, 25 residues or less, or 20 residues or less, excluding the sequence of amino acids at positions 175 to 198.

Furthermore, the peptides of the present invention may comprise additional amino acid sequences other than the amino acid sequence derived from a PHB2 polypeptide as long as they maintain the activity to inhibit the binding between a BIG3 polypeptide and a PHB2 polypeptide and do not block the suppression of estrogen receptor activation by the PHB2 polypeptide. Also in this case, it is desirable that the additional amino acid sequences do not block the binding between an endogenous PHB2 polypeptide and an estrogen receptor. Thus, the peptides of the present invention are preferably a peptide of 100 residues or less, 80 residues or less, or 70 residues or less. In a more preferred embodiment, the peptides of the present invention are peptides of 50 residues or less, 40 residues or less, or 30 residues or less. Preferred examples of amino acid sequences comprised in the peptides of the present invention include, but are not limited to, amino acid sequences constituting cell-permeable peptides described later and linker sequences for coupling other substances.

Moreover, the peptides of the present invention may be modified with other substances. Herein, the term "modified" used in the context of a peptide means that another substance (s) is/are directly or indirectly coupled to a peptide. Other substances that modify the peptides of the present invention include, but are not limited to, for example, peptides, lipids, saccharides, and natural or synthetic polymers. The peptides of the present invention can have any modifications as long as they maintain the activity to inhibit the binding between a BIG3 polypeptide and a PHB2 polypeptide. Furthermore, the peptides of the present invention may be conferred additional functions by modifications. Examples of the additional functions include, but are not limited to, targeting property, stability, and cell membrane permeability.

Preferred examples of modifications in the present invention include introduction of a cell membrane permeable substance. Intracellular structure is usually cut off from the outside world by the cell membrane. Thus, it is difficult to efficiently introduce an extracellular substance into a cell. However, a certain type of substance has cell membrane permeability and can be introduced into a cell without being cut off by the cell membrane. It is possible to confer cell membrane permeability to a substance with no cell membrane permeability by modifying the substance with such a substance having cell membrane permeability (cell membrane permeable substance). Accordingly, the peptides of the present invention can be efficiently introduced into cells by modifying the peptide of the present invention with a cell membrane permeable substance(s). Furthermore, as used herein, "cell membrane permeability" refers to the property of being able to permeate the cell membrane of mammals and enter the cytoplasm. Moreover, a "cell membrane permeable substance" refers to a substance having "cell membrane permeability".

Examples of the cell membrane permeable substance include, but are not limited to, membrane fusogenic liposomes and cell membrane permeable peptides. For example, membrane fusogenic liposomes are fused to cell membrane to release their contents into a cell. Membrane fusogenic liposomes can be prepared, for example, by modifying the surface of liposomes with a substance having membrane fusogenicity. Examples of membrane fusogenic liposomes include pH-sensitive liposomes (Yuba E, et al., J. Control. Release, 149, 72-80 (2011)), Sendai virus membrane fusogenic liposomes (WO 97/016171), and liposomes modified with cell membrane permeable peptides. The peptides of the present invention may be encapsulated into a membrane fusogenic liposome to efficiently introduce the peptides into a cell. In the present invention, encapsulation of a peptide into a membrane fusogenic liposome is also encompassed in "modification" of a peptide.

Various natural or artificially synthesized peptides have so far been reported as cell membrane permeable peptides (Joliot A. & Prochiantz A., Nat Cell Biol. 2004; 6: 189-96). Examples of cell membrane permeable peptides include the following peptides, but are not limited thereto.

Polyarginine (Matsushita et al., J. Neurosci.; 21(16), 6000-7 (2003)); Tat/RKKRRQRRR (SEQ ID NO: 90) (Frankel et al., Cell 55(6), 1189-93 (1988)., Green & Loewenstein Cell 55, 1179-88 (1988));

Penetratin/RQIKIWFQNRRMKWKK (SEQ ID NO: 103) (Derossi et al., J. Biol. Chem. 269(14), 10444-50 (1994));

Buforin II/TRSSRAGLQFPVGRVHRLLRK (SEQ ID NO: 91) (Park et al., Proc. Natl Acad. Sci. USA 97(15), 8245-50 (2000));

Transportan/GWTLNSAGYLLGKINLKALAALAKKIL (SEQ ID NO: 92) (Pooga et al., FASEB J. 12(1), 67-77 (1998));

MAP (Model Amphipathic Peptide)/KLALKLALKAL-KAALKLA (SEQ ID NO: 93) (Oehlke et al., Biochim. Biophys. Acta. 1414(1-2), 127-39 (1998));

K-FGF/AAVALLPAVLLALLAP (SEQ ID NO: 94) (Lin et al., J. Biol. Chem. 270(24), 14255-8 (1995));

Ku70NPMLK (SEQ ID NO: 95) (Sawada et al., Nature Cell Biol. 5(4), 352-7 (2003));

Ku70/PMLKE (SEQ ID NO: 96) (Sawada et al., Nature Cell Biol. 5(4), 352-7 (2003));

Prion/MANLGYWLLALFVTMWTDVGLCKKRPKP (SEQ ID NO: 97) (Lundberg et al., Biochem. Biophys. Res. Commun. 299(1), 85-90 (2002));

pVEC/LLIILRRRIRKQAHAHSK (SEQ ID NO: 98) (Elmquist et al., Exp. Cell Res. 269(2), 237-44 (2001));

Pep-1/KETWWETWWTEWSQPKKKRKV (SEQ ID NO: 99) (Morris et al., Nature Biotechnol. 19(2), 1173-6 (2001));

SynB1/RGGRLSYSRRRFSTSTGR (SEQ ID NO: 100) (Rousselle et al., Mol. Pharmacol. 57(4), 679-86 (2000));

Pep-7/SDLWEMMMVSLACQY (SEQ ID NO: 101) (Gao et al., Bioorg. Med. Chem. 10(12), 4057-65 (2002)); and HN-1/TSPLNIHNGQKL (SEQ ID NO: 102); (Hong & Clayman Cancer Res. 60(23), 6551-6 (2000)).

The above-mentioned polyarginine may be composed of any number of arginine residues. For example, polyarginine may be composed of 5 to 20 arginine residues. The number of arginine residues constituting polyarginine is not particularly limited as long as it does not block the activity of the peptide to inhibit the binding between a BIG3 polypeptide and a PHB2 polypeptide.

Furthermore, it is known in the art to introduce various particularly useful amino acid mimetics or unnatural amino acids (for example, by substitution, addition, or insertion) in order to increase in vivo stability of peptides. Examples of amino acid mimetics or unnatural amino acids to be introduced include, but are not limited to, β-amino acids, D-amino acids, and N-methyl amino acids. Accordingly, such amino acid mimetics or unnatural amino acids can be introduced into the peptides of the present invention to increase in vivo stability. Moreover, azapeptides in which α-carbons of amino acids have been substituted with an amino group and techniques for substituting amide bonds in peptides with their equivalents (such as esters, sulfonamides, and alkene isosteres) are also known in the art. Stability of peptides can be confirmed using, for example, peptidases and various biological media such as human plasma and serum (see, for example, Coos Verhoef et al. Eur. J. Drug Metab. Pharmacokin. 11(4): 291-302 (1986)).

Accordingly, the present invention provides peptides comprising the BIG3 polypeptide-binding site in a PHB2 polypeptide, which inhibit the binding between the PHB2 polypeptide and a BIG3 polypeptide and comprise at least one amino acid mimetic or unnatural amino acid (for example, β-amino acid, D-amino acid, and N-methyl amino acid). In a particular embodiment, the peptides of the present invention comprise an amino acid sequence in which one, two, or several amino acids are substituted with corresponding amino acid mimetics or unnatural amino acids (for example, β-amino acids, D-amino acids, and N-methyl amino acids) in an amino acid sequence selected from the group consisting of SEQ ID NOs: 1, 5, 36 to 41, 47 to 53, 82, and 83 (PHB2 sequence-derived peptides Nos. 1, 5, 36 to 41, 47 to 53, 82, and 83).

Moreover, the present invention also provides peptides comprising the BIG3 polypeptide-binding site in a PHB2 polypeptide, which inhibit the binding between the PHB2 polypeptide and a BIG3 polypeptide and in which at least one amide bond has been replaced with its equivalent (for example, an ester, sulfonamide, and alkene isostere).

Cyclic and Cross-Linked Peptides

In a particular embodiment, the peptides of the present invention may be cyclized and their stability can be improved by cyclization. Methods of introducing a cyclic structure into a peptide of the present invention are well known, and for example, a peptide can be cyclized by adding cysteine to the N- and C-termini of a linear peptide and allowing to form a disulfide bond between these cysteines. Herein, such a structure in which side chains of two (a pair of) amino acid residues in an amino acid sequence constituting a peptide are cross-linked (stapled) can be called a "stapling structure", and a cross-linked peptide into which one or more stapling structures have been introduced is also referred to as a "stapled peptide". Positions of amino acid residues forming such an intramolecular crosslink are not limited to the N- and C-termini of the original linear peptide, and amino acid residues present in the original linear peptide may form an intramolecular crosslink, or amino acid residues introduced into the original linear peptide (by, for example, substitution, addition, or insertion) may form an intramolecular crosslink. Amino acid residues forming an intramolecular crosslink are not limited to natural amino acids and may be amino acid mimetics or unnatural amino acids as described above. Moreover, methods of cross-linking a peptide are not limited to disulfide bond formation, and also include cross-linking of cysteine residues through fluorobenzene (for example, by using hexafluorobenzene or decafluorobiphenyl), thioether bond formation, ester bond formation, and a technique for stapling hydrocarbons such as ring-closing olefin metathesis (described in, for example, WO 2017/126461).

Furthermore, methods of cyclizing a peptide are not limited to methods of forming an intramolecular crosslink as mentioned above, and also include formation of an amide bond between the C-terminal and N-terminal amino acid residues of a peptide. The peptides thus cyclized by various methods are herein referred to as cyclic peptides, and include both cyclic peptides comprising an intramolecular crosslink (i.e., cross-linked peptides; for example, SEQ ID NOs: 25, 26, 123, 124, 126, and 127 depicted in FIGS. 4 and 11) and those not comprising an intramolecular crosslink (for example, SEQ ID NOs: 125 and 128 depicted in FIG. 11).

Accordingly, the present invention provides cyclic peptides comprising the BIG3 polypeptide-binding site in a PHB2 polypeptide, which inhibit the binding between the PHB2 polypeptide and a BIG3 polypeptide and have been cyclized by at least one intramolecular bond. Examples of the intramolecular bond include, but are not limited to, a disulfide bond, crosslink between cysteine residues through fluorobenzene (for example, by using hexafluorobenzene or decafluorobiphenyl), thioether bond, ester bond, thioester bond, bond by a hydrocarbon chain (for example, olefin and aryl), bond by a heterocycle (for example, triazole, oxazole, and thiazole) and amido bond, and combinations thereof.

Figures 4A, 4B, 4C:
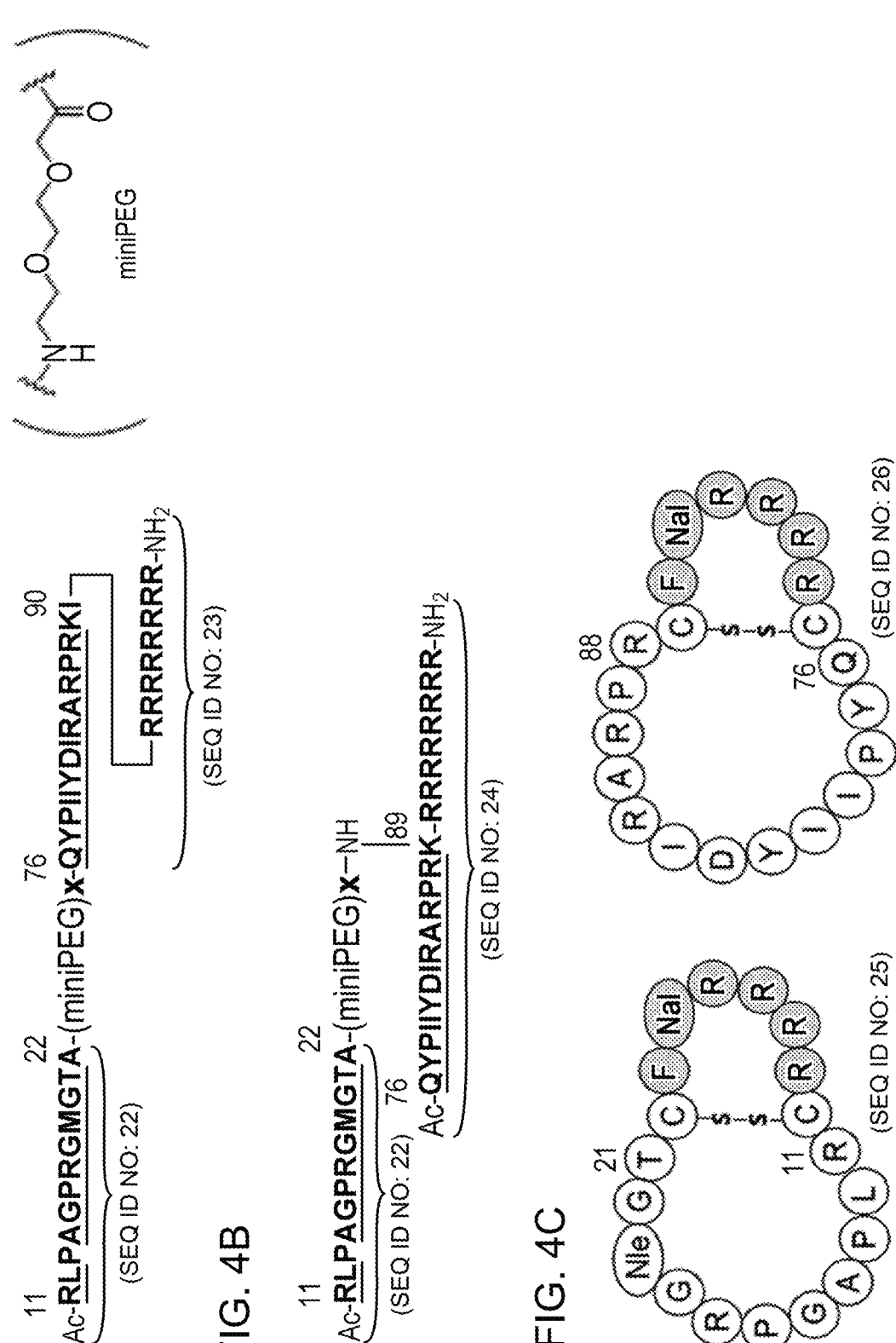
FIGS. 4A-4C show schemes of branched and cyclic PHB2 peptides.
Figures 5A, 5B, 5C:
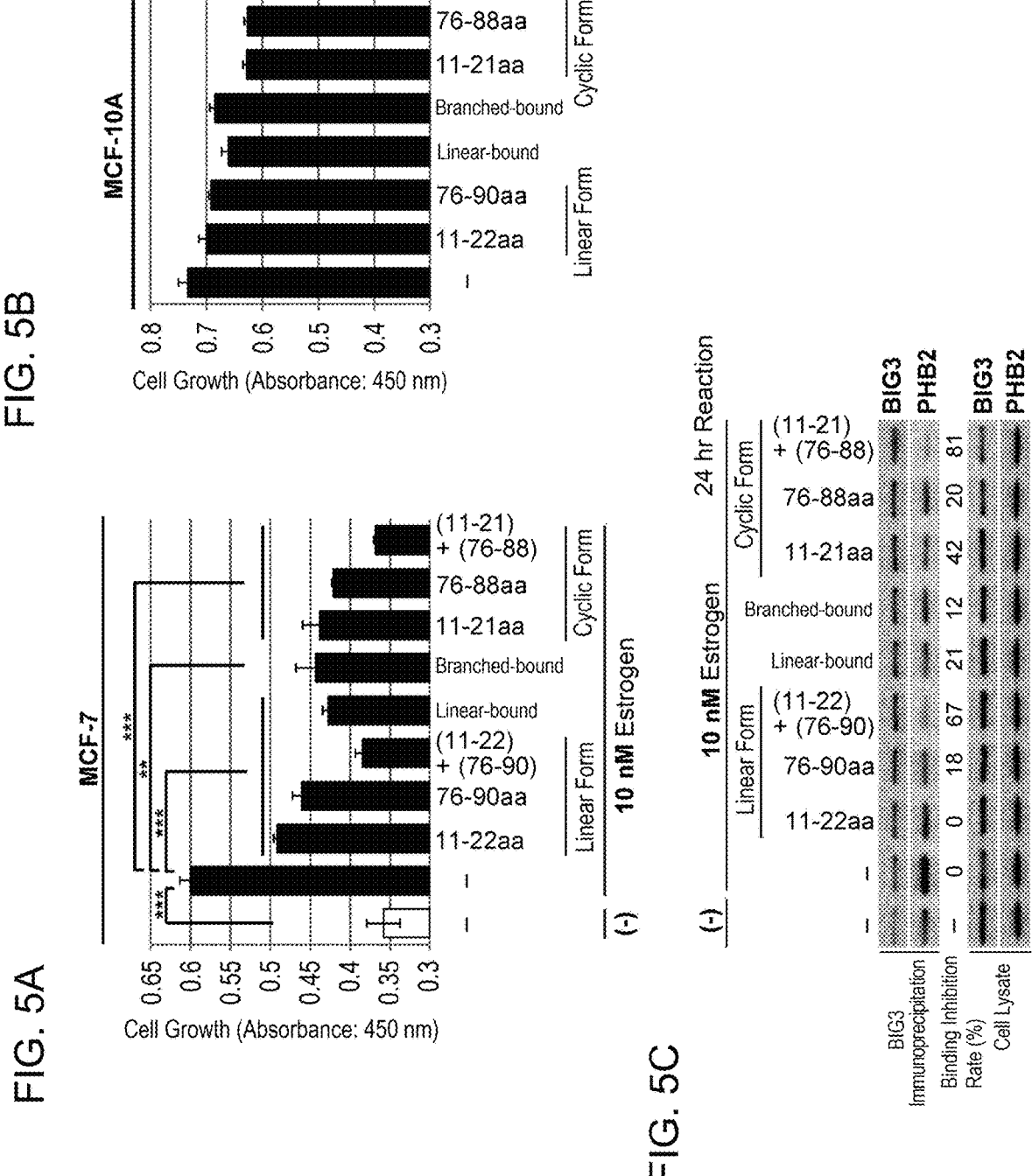
FIGS. 5A-5C show the suppressive effects of branched and cyclic PHB2 peptides on estrogen-dependent growth.
Figures 6A, 6B:
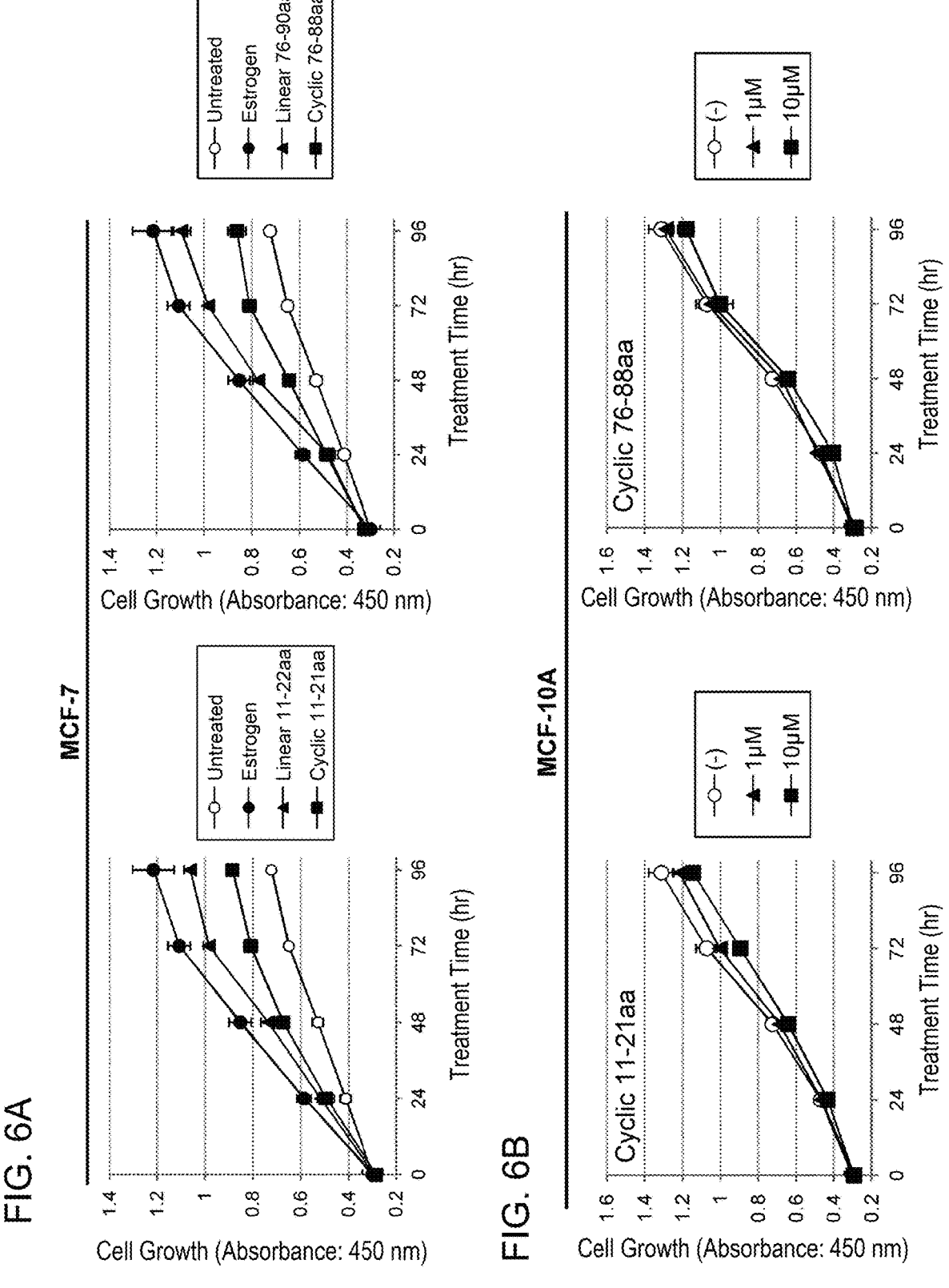
FIGS. 6A-6B show the effects of suppressing estrogen-dependent growth by a combination of cyclic PHB2 peptides.

Such an intramolecular bond may be formed by amino acid residues at both ends of the original linear peptide of a cyclic peptide, or may be formed by amino acid residues in the linear peptide. Moreover, the intramolecular bond may be formed by amino acid residues in an amino acid sequence derived from a PHB2 polypeptide, or may be formed by amino acid residues introduced into the amino acid sequence (by, for example, substitution, addition, or insertion). Preferred examples of such cyclic peptides of the present invention include cyclic PHB2 peptides of 11-21aa and 76-88aa (cyclic peptides respectively consisting of SEQ ID NO: 25, 106 to 108, 115 to 117, 123, or 124; and SEQ ID NO: 26, 110 to 112, 119 to 121, 126, or 127). These exemplary cyclic peptides are prepared by adding two cysteine residues that form an intramolecular bond (intramolecular crosslink) (SEQ ID NOs: 25, 26, 106 to 108, 110 to 112, 115 to 117, 119 to 121, 123, 124, 126, and 127); adding or substituting unnatural amino acids (SEQ ID NOs: 25, 26, 106 to 108, 115 to 117, 123, 124, 126, and 127); and adding consecutive multiple arginine residues (SEQ ID NOs: 25, 26, 106 to 108, 110 to 112, 123, 124, 126, and 127), in the linear peptides of PHB2 sequence-derived 11-21aa and 76-88aa with the objective of stabilization of the structure (and increase in the activity and improvement of protease resistance accompanied thereby) and improvement of membrane permeability. Such peptides have been cyclized by formation of an intramolecular crosslink between the two cysteine residues introduced (SEQ ID NOs: 25, 26, 106 to 108, 110 to 112, 115 to 117, 119 to 121, 123, 124, 126, and 127) and by formation of an amido bond between the C-terminal and N-terminal amino acid residues added (SEQ ID NOs: 25, 26, 123, 124, 126, and 127) (FIGS. 4C, 10A, and 11A). These exemplary cyclic peptides (in particular, cyclic and cross-linked peptides) showed an enhanced growth suppressive effect as compared to the original linear peptides (FIGS. 5A, 10C, and 11B) and the suppressive effect was shown to last for a long time (FIG. 6A).

The present invention also relates to methods of producing a cyclic peptide, the method comprising:

(a) providing a linear peptide comprising the BIG3 polypeptide-binding site in a PHB2 polypeptide, which inhibits the binding between the PHB2 polypeptide and a BIG3 polypeptide; and (b) allowing to form at least one intramolecular bond in the linear peptide, thereby cyclizing the linear peptide.

The intramolecular bond is optionally selected from the group consisting of a disulfide bond, crosslink between cysteine residues through fluorobenzene (for example, by using hexafluorobenzene or decafluorobiphenyl), thioether bond, ester bond, thioester bond, bond by a hydrocarbon chain (for example, olefin and aryl), bond by a heterocycle (for example, triazole, oxazole, and thiazole) and amido bond, and combinations thereof.

The above methods optionally comprise introducing at least one selected from the group consisting of cysteine residues, an amino acid mimetic(s) or unnatural amino acid(s), and consecutive multiple arginine residues into the linear peptide (by, for example, substitution, addition, or insertion).

The peptides of the present invention have the feature of having the activity to inhibit the binding between a PHB2 polypeptide and a BIG3 polypeptide. Whether a peptide produced has the activity to inhibit the binding between a PHB2 polypeptide and a BIG3 polypeptide or not can be confirmed by comparing the binding level between the PHB2 polypeptide and the BIG3 polypeptide in the presence and absence of the peptide. That is, when the binding level in the presence of a peptide is lower than that in the absence of the peptide, the peptide can be judged to have "the activity to inhibit the binding between a PHB2 polypeptide and a BIG3 polypeptide".

The binding level between a PHB2 polypeptide and a BIG3 polypeptide can be measured using various known methods. For example, immunoprecipitation using an anti-PHB2 antibody or an anti-BIG3 antibody, affinity chromatography, a biosensor using surface plasmon resonance phenomenon, and such can be used.

As a specific method, for example, a PHB2 polypeptide and a BIG3 polypeptide are incubated in the presence and absence of a test peptide. The reaction solution is then immunoprecipitated with an anti-PHB2 antibody or an anti-BIG3 antibody, and the immunoprecipitate is subjected to Western blot analysis. The binding level between the PHB2 polypeptide and the BIG3 polypeptide can be confirmed by detecting at least either one of the BIG3 polypeptide level immunoprecipitated with the anti-PHB2 antibody or the PHB2 polypeptide level immunoprecipitated with the anti-BIG3 antibody. The PHB2 polypeptide and BIG3 polypeptide used here can be prepared by a known genetic engineering technique. Furthermore, lysates of cells producing these polypeptides can be used. The cell lines as described in Examples of the present specification can be utilized as cells producing these polypeptides.

Alternatively, the methods as described in Examples of the present specification can also be used. Specifically, estrogen receptor-positive cells are cultured in the presence and absence of a test peptide. The cells are then lysed with an appropriate lysis buffer, and the cell lysate may be used to perform immunoprecipitation and Western blot analysis in the same manner as above.

A peptide for which "the activity to inhibit the binding between a PHB2 polypeptide and a BIG3 polypeptide" has been confirmed by any of the above methods is judged to be a peptide having "the activity to inhibit the binding between a PHB2 polypeptide and a BIG3 polypeptide".

Moreover, the peptides of the present invention may have either or both of the following (i) and (ii) as preferred properties:

(i) promoting the nuclear import of a PHB2 polypeptide in an estrogen receptor-positive cell which expresses a BIG3 polypeptide; and (ii) promoting the binding between an estrogen receptor present in the nucleus and/or on cell membrane and a PHB2 polypeptide in an estrogen receptor-positive cell which expresses a BIG3 polypeptide.

Whether a peptide of the present invention has the above properties or not can be confirmed by comparing (i) the nuclear import level of a PHB2 polypeptide; and/or (ii) the binding level between an estrogen receptor and a PHB2 polypeptide, in the presence and absence of the peptide of the present invention. That is, when the level in the presence of the peptide of the present invention is higher as compared to that in the absence of the peptide, the peptide can be judged to have the above-mentioned properties (i) and/or (ii).

Methods well known to one skilled in the art can be used as examples of specific methods for judging the presence or absence of the above-mentioned properties (i) and/or (ii). Specifically, when examining the above property (i), estrogen receptor-positive cells are stimulated with estradiol for 24 hours with or without the addition of a peptide of the present invention. The cells are then fractionated by specific gravity centrifugation, and PHB2 polypeptides present in the nuclear fraction are detected by Western blot analysis and such. When the level of PHB2 polypeptide detected in the nuclear fraction increases in the case where the peptide of the present invention is added as compared to the case where the peptide is not added, the peptide of the present invention is judged to have the above-mentioned property (i).

Moreover, the level of PHB2 polypeptide present in the nucleus can be detected by immunocytochemical staining.

When examining the above-mentioned property (ii), estrogen receptor-positive cells are stimulated with estradiol for 24 hours with or without the addition of a peptide of the present invention. The cells are then fractionated by specific gravity centrifugation, the cytosolic fraction and the nuclear fraction are immunoprecipitated with an anti-estrogen receptor antibody or an anti-PHB2 antibody, and the immunoprecipitate is subjected to Western blot analysis. As a result, when the binding level between an estrogen receptor and a PHB2 polypeptide in the cytosolic fraction and/or the nuclear fraction increases in the case where the peptide of the present invention is added as compared to the case where the peptide is not added, the peptide of the present invention is judged to have the above-mentioned property (ii).

The peptides of the present invention can be produced using methods well known to one skilled in the art. For example, the peptides of the present invention can be obtained by chemical synthesis based on their amino acid sequences. Methods for chemical synthesis of a peptide are known and one skilled in the art can chemically synthesize the peptide of the present invention based on amino acid sequence selected as the peptide of the present invention. Chemical synthesis methods of peptide are described, for example, in the documents below:

(i) Peptide Synthesis, Interscience, New York, 1966;

(ii) The Proteins, Vol. 2, Academic Press, New York, 1976;

(iii) "Peptide Synthesis" (in Japanese), Maruzen Co., 1975;

(iv) "Basics and Experiment of Peptide Synthesis" (in Japanese), Maruzen Co., 1985;

(v) "Development of Pharmaceuticals" (in Japanese), Continued Vol. 14 (peptide synthesis), Hirokawa, 1991;

(vi) WO99/67288; and (vii) Barany G. & Merrifield R. B., Peptides Vol. 2, Solid Phase Peptide Synthesis, Academic Press, New York, 1980, 100-118.

Alternatively, the peptides of the present invention can be obtained by genetic engineering methods (e.g., Morrison J, J Bacteriology, 132(1): 349-51 (1977); Clark-Curtiss & Curtiss, Methods in Enzymology (eds. Wu et al.), 101: 347-62 (1983)). For example, a polynucleotide encoding a peptide of the present invention is inserted into an appropriate expression vector, and the vector is introduced into appropriate host cells to prepare transformed cells. The transformed cells are then cultured to produce the peptide of the present invention, and the cell extract is prepared. Standard techniques for purifying proteins can be used to purify the peptide of the present invention from the cell extract. The peptide of the present invention can be purified by, for example, appropriately selecting and combining column chromatography, filter filtration, ultrafiltration, salting-out, solvent precipitation, solvent extraction, distillation, immunoprecipitation, SDS-polyacrylamide gel electrophoresis, isoelectric focusing, dialysis, and recrystallization. Furthermore, the peptides of the present invention can be synthesized by in vitro translation system in which elements necessary to synthesize protein have been reconstructed in vitro.

When using genetic engineering techniques, the peptides of the present invention can also be expressed as a fusion protein with other peptide. A polynucleotide encoding a peptide of the present invention is ligated in frame with a polynucleotide encoding other peptide and inserted into an appropriate expression vector, and the vector is introduced into appropriate host cells to prepare transformed cells. The host cells are then cultured to allow production of a fusion protein of the peptide of the present invention and the other peptide, and its cell extract is prepared. The purification of fusion protein from the cell extract can be performed by, for example, capturing the fusion protein by affinity chromatography using a column to which a substance having affinity to the fusion protein has been coupled. Moreover, if the peptide of the present invention has been coupled to another peptide through a linker sequence which can be cleaved by an enzyme such as peptidase, protease, and proteasome, the peptide of the present invention can be separated from the column by treating the fusion protein captured by the column with such an enzyme. Examples of other peptides which can be used to form fusion proteins include the following peptides, but are not limited thereto:

FLAG (Hopp et al., Bio/Technology 6, 1204-10 (1988));

6×His or 10×His consisting of histidine (His) residues;

Influenza Hemagglutinin (HA);

Human c-myc fragment, VSV-GP fragment; p18 HIV fragment;

T7 tag; HSV tag;

E tag; SV40T antigen fragment;

lck tag;

α-Tubulin fragment;

B tag;

Protein C fragment;

GST (Glutathione-S-transferase);

HA (Influenza Hemagglutinin);

Immunoglobulin constant region;

β-Galactosidase; and

MBP (Maltose-binding protein).

2. Polynucleotides Encoding the Peptides of the Present Invention, Vectors, and Host Cells The present invention also provides polynucleotides encoding the peptide of the present invention. Furthermore, the present invention provides vectors comprising the polynucleotide and host cells comprising the vector. Such polynucleotides, vectors, and host cells can be used to produce the peptides of the present invention.

The polynucleotides of the present invention can be produced by methods known to one skilled in the art. For example, the polynucleotides of the present invention can be synthesized using solid-phase techniques as described in Beaucage S L & Iyer R P, Tetrahedron, 48: 2223-311 (1992); Matthes et al., EMBO J, 3(4): 801-5 (1984). Moreover, the polynucleotides of the present invention can be prepared using genetic engineering techniques. For example, primers are produced based on a partial nucleotide sequence of a PHB2 gene (SEQ ID NO: 27) encoding an amino acid sequence selected as a peptide of the present invention, and reverse transcription-PCR is performed by using mRNAs extracted from cells expressing a PHB2 polypeptide as a template. Thus, the polynucleotides of the present invention can be amplified.

The polynucleotides of the present invention can be inserted into an appropriate expression vector and the vector is introduced into appropriate host cells to produce the peptide of the present invention in the host cells.

For example, when E. coli is selected as a host cell and a vector is amplified in a large amount in E. coli (for example, JM109, DH5-alpha, HB101 or XL1 Blue), the vector needs to have an "ori" for amplification in E. coli and a marker gene for selection of transformed E. coli (for example, a drug resistance gene selected by a drug such as ampicillin, tetracycline, kanamycin, chloramphenicol). For example, the M13-series vectors, pUC-series vectors, pBR322, pBluescript, pCR-Script and such can be used. When a vector is used for producing a peptide of the present invention, an expression vector is particularly useful. For example, an expression vector for expression in E. coli needs to have the above features for amplification in E. coli. When E. coli such as JM109, DH5-alpha, HB101 or XL1 Blue are used as a host cell, the vector needs to have a promoter, for example, lacZ promoter (Ward et al., Nature, 341(6242): 544-6 (1989); FASEB J, 6(7): 2422-7 (1992)), araB promoter (Better et al., Science, 240(4855): 1041-3 (1988)), T7 promoter or the like, that can efficiently express the desired gene in E. coli. Additionally, the vector may contain a signal sequence for polypeptide secretion. An exemplary signal sequence that directs the polypeptide to be secreted to the periplasm of the E. coli is the pelB signal sequence (Lei et al., J Bacteriol, 169(9): 4379-83 (1987)). Means for introducing the vectors into the target host cells include, for example, the calcium chloride method and the electroporation method.

In addition to E. coli, for example, expression vectors derived from mammalian cells (for example, pcDNA3 (Invitrogen) and pEGF-BOS (Mizushima S., Nucleic Acids Res, 18(17): 5322 (1990)), pEF, pCDM8), expression vectors derived from insect cells (for example, "Bac-to-BAC baculovirus expression system" (GIBCO BRL), pBacPAK8), expression vectors derived from plants (e.g., pMH1, pMH2), expression vectors derived from animal viruses (e.g., pHSV, pMV, pAdexLcw), expression vectors derived from retroviruses (e.g., pZIpneo), expression vectors derived from yeast (e.g., "Pichia Expression Kit" (Invitrogen), pNV11, SP-Q01) and expression vectors derived from Bacillus subtilis (e.g., pPL608, pKTH50) can be used.

In order to express the vector in animal cells such as CHO cells, COS cells or NIH3T3 cells, the vector needs to carry a promoter necessary for expression in such cells, for example, the SV40 promoter (Mulligan et al., Nature, 277 (5692): 108-14 (1979)), the MMLV-LTR promoter, the EF1-alpha promoter (Mizushima et al., Nucleic Acids Res, 18(17): 5322 (1990)), the CMV promoter and the like, and preferably a marker gene for selecting transformants (for example, a drug resistance gene selected by a drug (e.g., neomycin, G418)). Examples of known vectors with these characteristics include, for example, pMAM, pDR2, pBK-RSV, pBK-CMV, pOPRSV and pOP13.

Furthermore, the polynucleotide of the present invention may be inserted into an appropriate vector and the vector is introduced into target cells to produce the peptide of the present invention within the target cells. A peptide of the present invention produced in a target cell inhibits the binding between a PHB2 polypeptide and a BIG3 polypeptide and induces suppression of growth of the target cell. In this case, the vector into which a polynucleotide of the present invention is inserted may be a vector for stably inserting the polynucleotide of the present invention into the genome of the target cell (for example, see Thomas K R & Capecchi M R, Cell, 51(3): 503-12 (1987) for description of cassette vectors for homologous recombination). For example, see Wolff et al., Science, 247: 1465-8 (1990); U.S. Pat. Nos. 5,580,895; 5,589,466; 5,804,566; 5,739,118; 5,736,524; 5,679,647; and WO 98/04720.

Moreover, the polynucleotide of the present invention can be inserted into, for example, an expression vector such as a viral vector and a bacterial vector. Examples of the expression vector include a host for an attenuated virus of cowpox, fowlpox, and the like (see, for example, U.S. Pat. No. 4,722,858). Other examples of vectors that can be used include Bacille Calmette Guerin (BCG) (Stover et al., Nature, 351(6326): 456-60 (1991)). Other examples include adenovirus vectors, adeno-associated virus vectors, retrovirus vectors, Salmonella typhi vectors, and attenuated anthrax toxin vectors (Shata et al., Mol Med Today, 6(2): 66-71 (2000); Shedlock et al., J Leukoc Biol, 68(6): 793-806 (2000); and Hipp et al., In Vivo, 14(5): 571-85 (2000)).

Peptides of the present invention encompass peptides in which either or both of the N-terminal and C-terminal amino acid residues have been modified. The types of modifications are not particularly limited, but those that do not affect the affinity for BIG3 are preferred. Examples of preferred modifications include acetylation of the N-terminal amino acid residue, amidation of the C-terminal amino acid residue, addition of tag peptides such as HA-tag and FLAG-tag, and such.

The peptides of the present invention are not limited to those composed of L-amino acids and may be peptides including one or more D-amino acids. The composition ratio of L-amino acids to D-amino acids in the peptides is not particularly limited, and there may be any of the following cases: all amino acid residues may be in L-form (hereinafter referred to as "L-form peptide"); all amino acid residues may be in D-form (hereinafter referred to as "D-form peptide"); or only amino acid residues at a particular position(s) may be in D-form. One preferred embodiment of the peptides of the present invention includes a peptide in which all the amino acid residues have been substituted with D-form amino acid residues in any of the above-mentioned peptides of the present invention. Another preferred embodiment of the peptides of the present invention includes a peptide in which an amino acid residue(s) at a particular position(s) important for the binding to BIG3 has/have been substituted with the corresponding D-form amino acid residue(s). Examples of such a position include positions corresponding to glycine at position 15, glycine at position 18, and aspartic acid at position 82 in the amino acid sequence of SEQ ID NO: 28.

Furthermore, the peptides of the present invention may be retro-inverso forms of any of the above-mentioned peptides of the present invention. A retro-inverso form has an amino acid sequence that is reversed from that of the original peptide, and all amino acid residues are substituted with D-form amino acid residues. More specifically, a retro-inverso form is a D-form peptide having an amino acid sequence that is reversed from that of the original peptide. Therefore, peptides which are retro-inverso forms of any one of the above-mentioned peptides of the present invention are included as preferred embodiments of the peptides of the present invention.

Peptides of the present invention may also be in the form of salts. The form of salts is not particularly limited, but pharmaceutically acceptable salts are preferred. Herein, the "pharmaceutically acceptable salt" refers to a salt that retains the pharmacological and pharmaceutical efficacy and characteristics of a peptide. Preferred examples of salts include salts with alkali metals (lithium, potassium, sodium and such), salts with alkaline-earth metals (calcium, magnesium and such), salts with other metals (copper, iron, zinc, manganese and such), salts with organic bases, salts with amines, salts with organic acids (acetic acid, formic acid, propionic acid, fumaric acid, maleic acid, succinic acid, tartaric acid, citric acid, malic acid, oxalic acid, benzoic acid, methanesulfonic acid, and such), salts with inorganic acids (hydrochloric acid, phosphoric acid, hydrobromic acid, sulfuric acid, nitric acid and such), and such. These salts can be prepared according to known methods.

3. Pharmaceutical Compositions Comprising the Peptide or Polynucleotide of the Present Invention and Uses Thereof The present invention also provides pharmaceutical compositions comprising a peptide or a salt thereof of the present invention or a polynucleotide encoding a peptide of the present invention, along with a pharmaceutically acceptable carrier.

The peptides of the present invention inhibit the binding between a PHB2 polypeptide and a BIG3 polypeptide to induce the suppression of estrogen receptor activation by the PHB2 polypeptide, thereby leading to suppression of growth of estrogen receptor-positive cells. Accordingly, the pharmaceutical compositions of the present invention are useful in either or both of treatment and prophylaxis (prevention) of cell proliferative diseases caused by activation of estrogen receptors. Such cell proliferative diseases include, for example, cancer.

It is known that among cancers, particularly breast cancer is deeply related to activation of estrogen receptors. A BIG3 polypeptide is a novel estrogen receptor activation regulator and is frequently expressed in many breast cancer specimens and breast cancer cells; meanwhile, it has been confirmed that expression of a BIG3 polypeptide is hardly found in normal tissues (Kim J W, Akiyama M, Park J H, et al. Cancer Sci.; 100(8): 1468-78 (2009)). Thus, it is considered that in breast cancer, expression of a BIG3 polypeptide inhibits the function of a PHB2 polypeptide of suppressing activation of estrogen receptors, thereby growth of breast cancer cells is promoted. Accordingly, the pharmaceutical compositions of the present invention are particularly suitable for either or both of treatment and prophylaxis (prevention) of breast cancer. Furthermore, among breast cancers, the pharmaceutical compositions of the present invention are particularly useful in breast cancers that are estrogen receptor-positive and express BIG3 polypeptides. However, the pharmaceutical compositions of the present invention are not limited to use for breast cancer, and they can be used for any cancer as long as it is estrogen receptor-positive and expresses a BIG3 polypeptide. Examples of estrogen receptor-positive cancer besides breast cancer include endometrial cancer, ovarian cancer, prostate cancer (Nelles J L, et al., Expert Rev Endocrinol Metab., 6(3): 437-51 (2011)), and lung cancer (particularly non-small-cell lung cancer) (Stabile L P, et al., Cancer Res., 65(4): 1459-70 (2005); Marquez-Garban D C, et al., Steroids. 72(2): 135-43 (2007)), but are not limited thereto. Cancers to which pharmaceutical compositions of the present invention are applied preferably express BIG3 and PHB2, and estrogen receptor-positive cancers generally express BIG3 and PHB2. Whether a cancer is estrogen receptor-positive can be confirmed by known methods such as ELISA or immunohistochemical staining.

Furthermore, the peptides of the present invention showed excellent cell growth inhibitory effects in triple-negative breast cancer cells, which are estrogen receptor-negative breast cancer cells (FIG. 9). Generally, triple-negative refers to breast cancer cells lacking expression of HER2, estrogen receptors, and progesterone receptors, which are targeted factors in major drug treatments. Therefore, triple-negative breast cancers are normally resistant to drug treatment. Therefore, the pharmaceutical compositions of the present invention can be applied to either or both of treatment and prophylaxis (prevention) of estrogen receptor-negative breast cancer, and are also useful as pharmaceutical compositions for administration to patients with such treatment-resistant breast cancers.

More specifically, the present invention provides pharmaceutical compositions comprising a peptide of the present invention, which are for administration to drug therapy-resistant breast cancer patients. The present invention also relates to peptides of the present invention for use in either or both of treatment and prophylaxis (prevention) of drug therapy-resistant breast cancer patients. Furthermore, the present invention relates to use of the peptides of the present invention in the production of pharmaceutical compositions for either or both of treatment and prophylaxis (prevention) of drug therapy-resistant breast cancer patients. The present invention also provides methods for either or both of treatment and prophylaxis (prevention) of breast cancer which comprise the steps of selecting patients having drug therapy-resistant breast cancer, and administering a peptide of the present invention to the selected patients.

Patients with drug therapy-resistant breast cancer can be identified by observing the therapeutic outcome after common drug therapy. Specifically, when degeneration of the disease focus is not clearly observed by the treatment, one can know that this cancer is treatment-resistant. A condition where enlargement of the disease focus is prevented is included in the degeneration of the disease focus. The above-mentioned triple-negative breast cancer patients are said to have resistance to drug therapies. Triple-negative refers to breast cancers having the features of lacking expression of estrogen receptors and progesterone receptors in addition to HER2. These markers for drug therapy resistance can be evaluated quantitatively by immunostaining and gene expression profiling. For example, the marker status is determined to be negative when the expression level is approximately the same as that of a negative control. For the negative control, treatment-resistant cancer cell lines lacking expression of these markers can be used.

Pharmaceutical compositions of the present invention can be produced using known drug formulation techniques by mixing a peptide or a salt thereof of the present invention with a pharmaceutically acceptable carrier. Herein, "pharmaceutically acceptable carrier" refers to an inactive substance to be used as diluents or solvents for drugs. For the pharmaceutically acceptable carriers to be used in pharmaceutical compositions of the present invention, carriers generally used for pharmaceutical products can be appropriately selected according to the dosage form of the pharmaceutical compositions to be prepared.

The dosage forms of the pharmaceutical compositions of the present invention are not particularly limited, and dosage forms generally used for pharmaceutical products such as liquids, tablets, elixirs, capsules, granules, and powders can be selected appropriately. Furthermore, depending on the selected dosage form, additives such as excipients, stabilizers, suspensions, preservatives, surfactants, solubilizing agents, pH adjusters, and aggregation inhibitors can be added appropriately.

The pharmaceutical compositions of the present invention comprise as an active ingredient a pharmaceutically effective amount of a peptide or a salt thereof of the present invention or a polynucleotide encoding the peptide. A "pharmaceutically effective amount" is an amount sufficient for a pharmaceutical composition of the present invention to accomplish its objective. For example, when a pharmaceutical composition of the present invention is for a pharmaceutical composition for either or both of the treatment and prophylaxis (prevention) of cancer, an example of a pharmaceutically effective amount can be an amount that induces suppression of cancer growth rate, suppression of metastatic potential, prolonged survival time, suppression or delay of cancer development, or alleviation of various clinical symptoms associated with cancer, when administered to a patient. Suppression of cancer growth rate can be, for example, suppression of about 5% or more compared to when the pharmaceutical composition of the present invention is not administered. Preferably, suppression of cancer growth rate can be about 10% or more, 20% or more, 30% or more, 40% or more, 50% or more, 75% or more, 80% or more, 90% or more, or 100% or more.

The pharmaceutically effective amount can be selected appropriately according to the dosage form of the pharmaceutical compositions, dosage interval, age, gender, body weight, and body surface area of subjects for administration, type of disease, and such. Examples of the content of peptides or salts thereof of the present invention in pharmaceutical compositions of the present invention include 0.001 mg to 1000 mg, 0.01 mg to 100 mg, 0.1 mg to 30 mg, or 0.1 mg to 10 mg, but are not limited thereto.

Pharmaceutical compositions of the present invention may optionally include other pharmaceutical agents. Examples of other pharmaceutical agents include anti-inflammatory agents, analgesic agents, antipyretics, other therapeutic agents for cancer, and such. Other therapeutic agents for cancer that may be used for pharmaceutical compositions of the present invention are not particularly limited, but when the pharmaceutical compositions are used for estrogen-positive cancers, examples may include hormone therapy agents such as selective ERα modulators (e.g., tamoxifen and raloxifene), ERα down-regulators (e.g., fulvestrant), aromatase inhibitors, LH-RH agonist formulations, and progesterone formulations. These pharmaceutical agents may also be mixed in the form of prodrugs and pharmaceutically acceptable salts.

Pharmaceutical compositions of the present invention can be administered to a subject by appropriately selecting a suitable administration route depending on the dosage form. The administration route is not particularly limited, but examples include oral administration, intradermal, subcutaneous, intramuscular, intraosseous, peritoneal and intravenous injection, and such. Furthermore, while either systemic administration or local administration near the diseased site is possible, local administration is preferred. More specifically, pharmaceutical compositions of the present invention can be administered by means of injection and such to the cancer tissue or to its vicinity. Alternatively, pharmaceutical compositions of the present invention can be administered surgically into the cancer tissue or to its vicinity. Pharmaceutical compositions of the present invention can also be prepared as a controlled-release preparation by combining them with appropriate carriers.

Dosage interval of pharmaceutical compositions of the present invention may also be appropriately selected according to the age, gender, body weight, and body surface area of subjects for administration, the disease type and such, as well as the dosage form, administration route, and such of the pharmaceutical compositions of the present invention. Examples of the dosage interval include every day, every four days, and every seven days, but are not limited thereto.

Dosage of pharmaceutical compositions of the present invention may also be appropriately selected according to the age, gender, body weight, and body surface area of subjects for administration, the disease type and such, as well as the dosage form, administration route, and such of the pharmaceutical compositions of the present invention.

Examples of the dosage of peptides or salts thereof of the present invention include, for example, 0.001 mg/kg/day to 1000 mg/kg/day, 0.005 mg/kg/day to 500 mg/kg/day, 0.01 mg/kg/day to 250 mg/kg/day, but are not limited thereto.

Pharmaceutical compositions of the present invention may be used in combination with other pharmaceuticals depending on the condition of the administration subjects. The pharmaceuticals used in combination are not particularly limited, but when the pharmaceutical compositions are used for estrogen receptor-positive cancers, examples may include hormone therapy agents such as selective ERα modulators (e.g., tamoxifen and raloxifene), ERα down-regulators (e.g., fulvestrant), aromatase inhibitors, LH-RH agonist formulations, and progesterone formulations. Among these hormone therapy agents, particularly preferred examples include tamoxifen and fulvestrant.

When pharmaceutical compositions of the present invention are used for cancer treatment, one may examine whether the cancer to be treated is accompanied by expression of BIG3 and PHB2 before administering the pharmaceutical compositions. Whether BIG3 and PHB2 are expressed in the cancer to be treated can be confirmed by detecting transcription products or translation products of these genes in the samples collected from the subjects. Known methods can be used for detection methods, and for example, methods of detecting transcription products using probes or PCR methods (for example, cDNA microarray method, Northern blotting, and RT-PCR) and methods of detecting translation products using antibodies and such (for example, Western blotting and immunostaining) may be used.

The present invention also provides articles of manufacture or kits that comprise a pharmaceutical composition of the present invention. The articles of manufacture or kits of the present invention can include a container that houses the pharmaceutical composition of the present invention. An example of an appropriate container includes a bottle, a vial or a test tube, but is not limited thereto. The container may be formed of various materials such as glass or plastic. A label may be attached to the container, and the disease or disease state to which the pharmaceutical composition of the present invention should be used may be described in the label. The label may also indicate directions for administration and such.

The articles of manufacture or kits of the present invention may further comprise a second container that houses pharmaceutically acceptable diluents optionally, in addition to the container that houses the pharmaceutical composition of the present invention. The articles of manufacture or kits of the present invention may further comprise the other materials desirable from a commercial standpoint and the user's perspective, such as the other buffers, diluents, filters, injection needles, syringes, and package inserts with instructions for use.

As needed, the pharmaceutical composition of the present invention can be provided in a pack or dispenser device that can contain one or more units of dosage forms containing active ingredients. The pack can include, for example, a metallic foil or a plastic foil such as a blister pack. Instructions for administration can be attached to the pack or dispenser device.

In another embodiment, the present invention provides the following uses, methods, and such:

(a) uses of the peptide or salt thereof, or polynucleotide encoding the peptide of the present invention in the manufacture of a pharmaceutical composition for either or both of treatment and prophylaxis (prevention) of cancer;

(b) the peptides or salts thereof, or polynucleotides encoding the peptides of the present invention for use in either or both of treatment and prophylaxis (prevention) of cancer;

(c) methods or processes for manufacturing a pharmaceutical composition for either or both of treatment and prophylaxis (prevention) of cancer, the method or process comprising formulating the peptide or salt thereof, or polynucleotide encoding the peptide of the present invention and a pharmaceutically acceptable carrier(s);

(d) methods or processes for manufacturing a pharmaceutical composition for either or both of treatment and prophylaxis (prevention) of cancer, the method or process comprising mixing the peptide or salt thereof, or polynucleotide encoding the peptide of the present invention with a pharmaceutically acceptable carrier (s); and (e) methods for either or both of treatment and prophylaxis (prevention) of cancer, the method comprising administering the peptide or salt thereof, or polynucleotide encoding the peptide of the present invention to a subject.

In the above uses, methods and such, cancer is preferably BIG3-positive cancer and may be estrogen receptor-positive cancer or estrogen receptor-negative cancer (for example, triple-negative breast cancer). A preferred example of such cancer includes breast cancer.

Hereinbelow, the present invention is described in more detail with reference to the Examples. Nevertheless, while the following materials, method and Examples may serve to assist one of ordinary skill in making and using certain embodiments of the present invention, there are only intended to illustrate aspects of the present invention and thus in no way to limit the scope of the present invention. One of ordinary skill in the art can use methods and materials similar or equivalent to those described herein in the practice or testing of the present invention.

All prior art documents cited herein are incorporated by reference in the present specification.

EXAMPLE

[Example 1] Effects on Estrogen-Dependent Breast Cancer

1. Materials and Methods

Cell Lines and Culturing Conditions

Human breast cancer cell line MCF-7 was purchased from JCRB Cell Bank (Osaka, Japan) and maintained in MEM (Thermo Fisher Scientific) supplemented with 10% FBS (Nichirei Biosciences Inc., Tokyo, Japan), 1% Antibiotic/Antimycotic solution (Thermo Fisher Scientific, Waltham, Mass., USA), 0.1 mM NEAA (Thermo Fisher Scientific), 1 mM sodium pyruvate (Thermo Fisher Scientific), and 10 µg/mL insulin (Sigma, St. Louis, Mo., USA) under 5% $CO_2$ at 37° C.

Normal mammary gland epithelial cell line MCF-10A was purchased from American Type Culture Collection (ATCC, Manassas, Va., USA), and maintained in MEBM (Lonza) supplemented with a Single Quots kit (BPE, hydrocortisone, hEGF, insulin, gentamycin/amphoterin-B) (Lonza, Walkersville, Md., USA) and 100 ng/mL cholera toxin under 5% $CO_2$ at 37° C.

Cell Growth Assay

Growth assay on MCF-7 was carried out by seeding cells into 48-well plates ($2 \times 10^4$ cells/200 µL). First, on the next day after seeding, the medium was changed to phenol red-free DMEM/F12 (Thermo Fisher Scientific) supplemented with 10% FBS, 1% Antibiotic/Antimycotic solution, 0.1 mM NEAA, 1 mM sodium pyruvate, and 10 µg/mL insulin. 24 hours later, the cells were treated with 10 nM 17β-estradiol (estrogen, Sigma) alone or with 10 nM estrogen and a PHB2 sequence-derived peptide. Growth assay on MCF-10A was carried out by seeding cells into 48-well plates ($2 \times 10^4$ cells/200 µL). 24 hours after seeding, PHB2 sequence-derived peptide was added. Growth assays were carried out using the Cell Counting Kit-8 (CCK-8) (Dojindo, Kumamoto, Japan). The data are shown by mean±standard deviation of three independent experiments.

Antibodies and Immunoblot Analyses

For immunoblot analyses, after performing SDS-PAGE, the membranes blotted with proteins were blocked with 4% BlockAce solution (Dainippon Pharmaceutical, Osaka, Japan) for 3 hours and then incubated to react for 12 hours with antibodies against BIG3 (1:1,000), PHB2 (1:1,000) (Abcam, Cambridge, UK) and phosphorylated PHB2 (Ser39, Scrum, Tokyo, Japan). After allowing interaction with HRP-labeled secondary antibodies (anti-rat IgG-HRP for BIG3, 1:5,000; and anti-rabbit IgG-HRP for PHB2 and phosphorylated PHB2, 1:1,000) (Santa Cruz Biotechnology, Dallas, TX, USA) for 1 hour, the blots were developed with the Enhanced Chemiluminescence (ECL) system (GE Healthcare, Buckinghamshire, UK) and scanned using the Image Reader LAS-3000 mini (Fujifilm, Tokyo, Japan).

Immunoprecipitation

For immunoprecipitation, MCF-7 was seeded into 10 cm dishes ($2 \times 10^6$ cells/10 mL), and like cell growth assay, MCF-7 was treated with 10 nM estrogen alone or with 10 nM estrogen and PHB2 sequence-derived peptide. For immunoprecipitation analysis, cell lysates lysed in a cell lysis buffer (50 mM Tris-HCl; pH 8.0, 150 mM NaCl, 0.1% NP-40, and 0.5% CHAPS; 0.1% protease inhibitor cocktail III) were pre-cleared with a rat IgG antibody and rec-Protein G Sepharose 4B (Thermo Fisher Scientific) at 4° C. for 3 hours. Then, the supernatants were incubated for reaction with 5 µg of an antibody against BIG3 at 4° C. for 12 hours. Next, the antigen-antibody complexes were precipitated using rec-Protein G Sepharose 4B at 4° C. for 1 hour. The immunoprecipitated protein complexes were washed four times with the cell lysis buffer. Then, SDS-PAGE and immunoblot analyses were carried out.

Peptide Synthesis

All peptides were synthesized by the Fmoc solid-phase synthesis method. NovaSyn TGR resin (0.25 mmol amine/g) or Rink Amide AM resin (0.62 mmol amine/g) was used as resin and a manual Fmoc solid-phase synthesis method was utilized. The Fmoc group was removed by the following procedures: reacting with 20% (v/v) piperidine/DMF solution at room temperature for 10 minutes, the resin was washed five to ten times with DMF, and then three equivalents of an Fmoc amino acid was subjected to coupling in a DMF solvent at room temperature for 90 minutes using N,N-diisopropylcarbodiimide (DIPCDI; 3.0 equivalents) and 1-hydroxy benzotriazole hydrate (HOBt.H$_2$O; 3.3 equivalents) or using N,N-diisopropylethylamine (DIPEA; 3.0 equivalents) and N,N,N,N-tetramethyl-O-(benzotriazole-1-yl)uronium hexafluorophosphate (HBTU; 2.9 equivalents). After washing with DMF, methanol, and ethanol and drying, the protected peptide resin was reacted with a cocktail of TFA:thioanisole:m-cresol:1,2-ethanedithiol:water (80:5:5:5:5) in the proportion of 100 mg of the protected peptide resin to 5 mL of the cocktail at room temperature for 90 minutes. After TFA was concentrated by nitrogen stream, the residual was precipitated by adding ether, and the precipitate was washed with ether and then dissolved in an appropriate aqueous solvent to perform preparative purification by HPLC.

2. Results

Screening of PHB2 Sequence-Derived Peptides

Figure 1A:
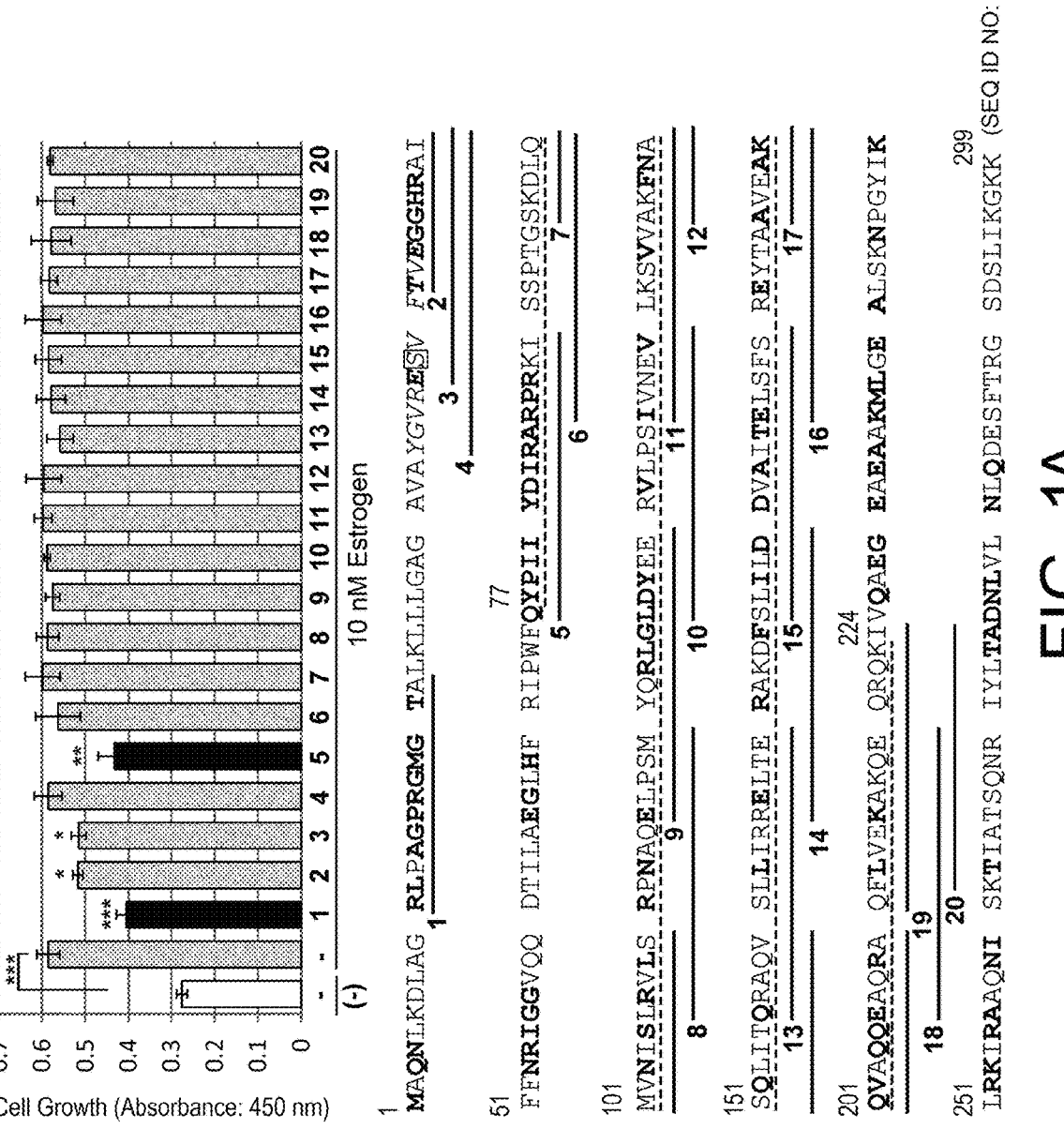
FIG. 1A: screening for PHB2 sequence-derived peptides which suppress estrogen-dependent cell growth is shown. Human breast cancer cell line MCF-7 was treated with 10 μM each of PHB2 sequence-derived peptides, and then immediately stimulated with 10 nM estrogen to evaluate the cell number for 24 hours by MTT assay. The data represents mean±standard deviation of three independent experiments. The full-length sequence of human PHB2 protein is shown below the graph, and synthetic peptides in which eight arginine residues were added to the C terminus of the underlined sequences were used in the assay. Moreover, the bold letters represent amino acids which are suggested to be involved in the interaction with BIG3 by in silico analysis, boxed "S" represents the phosphorylation site of PHB2, and the broken line represents a region whose binding to BIG3 has been demonstrated.

The 20 types of PHB2 protein sequence-derived peptides depicted in FIG. 1A were used to examine the suppressive effects on estrogen (E2)-dependent growth of MCF-7 (treated with 10 µM each peptide for 24 hours). As a result, growth of MCF-7 was significantly promoted by E2 stimulation, while treatments with PHB2-derived peptides No. 1 (11-22aa; SEQ ID NO: 1) and No. 5 (76-90aa; SEQ ID NO: 5) respectively showed the effect of significantly suppressing the E2-dependent growth by about 50% (No: 1: suppression ratio of 58%; No. 5: suppression ratio of 49%). Both peptides almost coincided with the BIG3-binding region predicted by in silico analysis (amino acids in bold letters). Furthermore, peptides No. 2 (42-50aa; SEQ ID NO: 2) and No. 3 (38-50aa; SEQ ID NO: 3) also showed the effect of suppressing the E2-dependent growth by 22% and 23%, respectively. However, each PHB2 sequence-derived peptide had a lower suppressive effect on the E2-dependent growth compared to that of ERAP, suggesting that PHB2 may have multiple BIG3-binding regions.

Figures 1B, 1C:
FIGS. 1B-1C: MCF-7 was treated with 10 μM each of PHB2 sequence-derived peptides surrounding 11-22aa (FIG. 1B) and 76-90aa (FIG. 1C) (SEQ ID NOs: 1, 34 to 43, 5, and 44 to 55), and then immediately stimulated with 10 nM estrogen to evaluate the cell number for 24 hours by MTT assay. The data represents mean±standard deviation of three independent experiments. The positions of the PHB2-derived sequences contained in the synthetic peptides used in the assay are shown on the left side of the graph.

Next, additional PHB2 sequence-derived peptides surrounding No. 1 (11-22aa) and No. 5 (76-90aa) were synthesized (FIGS. 1B and 1C), and the effect of treatment with 10 µM each peptide for 24 hours on the E2-dependent growth was examined. As a result, among the peptides around No. 1 (11-22aa), the PHB2 (11-22aa) peptide showed the highest suppression ratio (63%), while the suppressive effect attenuated with distance from there (FIG. 1B). On the other hand, among the peptides around No. 5 (76-90aa), the PHB2 (76-90aa) peptide showed the highest suppression ratio (51%), and No. 50 (75-89aa) also had almost the same suppressive effect; however, similarly to the above, the suppression ratio decreased with distance from these peptides (FIG. 1C). What is common to these data is that they comprise each amino acid of 11-21aa and 76-88aa, which showed a high score among the BIG3-binding sites predicted by in silico analysis, and the data suggested that there are two BIG3-binding sites in PHB2.

Figure 1E:
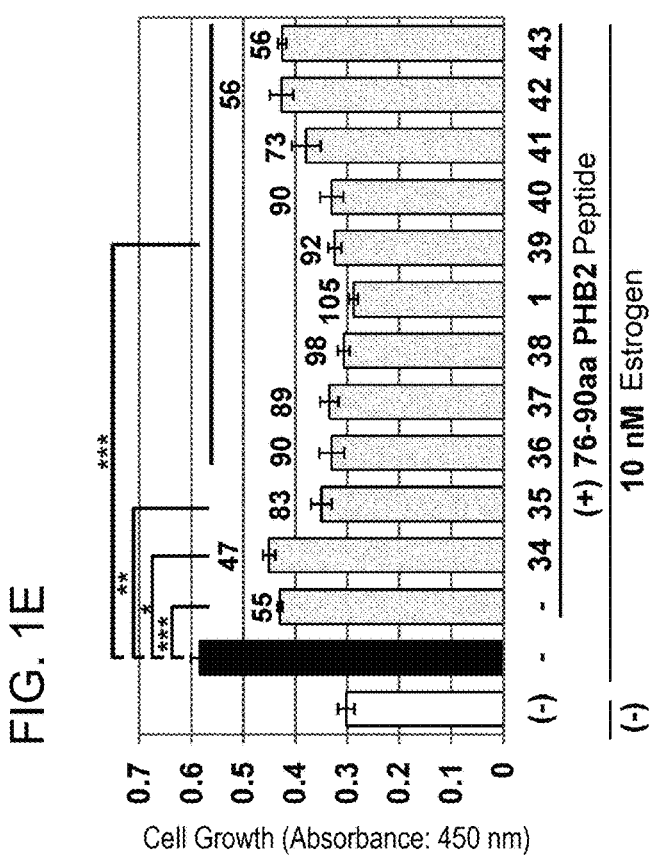
FIG. 1E: MCF-7 was treated with the combinations of 10 μM PHB2 sequence-derived peptide 76-90aa with 10 μM each of PHB2 sequence-derived peptides surrounding 11-22aa, and then the cells were immediately stimulated with 10 nM estrogen to evaluate the cell number for 24 hours by MTT assay. The data represents mean±standard deviation of three independent experiments.
Figure 1D:
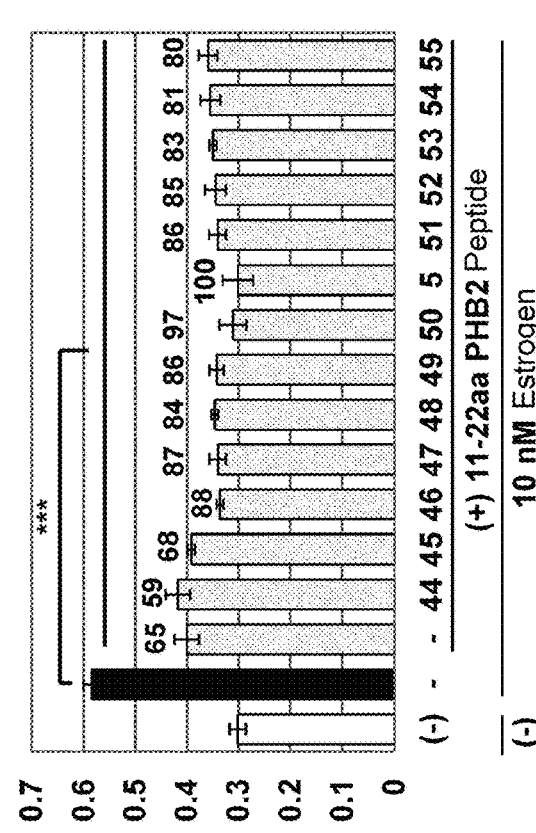
FIG. 1D: MCF-7 was treated with the combinations of 10 μM PHB2 sequence-derived peptide 11-22aa with 10 μM each of PHB2 sequence-derived peptides surrounding 76-90aa, and then the cells were immediately stimulated with 10 nM estrogen to evaluate the cell number for 24 hours by MTT assay.

Thus, the combinations of No. 1 (11-22aa) with peptides surrounding No. 5 (76-90aa) and the combinations of No. 5 (76-90aa) with peptides surrounding No. 1 (11-22aa) were examined for suppressive effect on the E2-dependent growth of MCF-7. As a result, treatment with peptide No. 1 (11-22aa) alone almost reproduced the result with a suppression ratio of 65% for the E2-dependent growth, and when this peptide was used in combination with PHB2 peptides surrounding No. 5 (76-90aa), the combinations with No. 5 (76-90aa) and with No. 50 (75-89aa) showed almost complete suppressive effects of 100% and 97%, respectively (FIG. 1D). Similarly, treatment with No. 5 (76-90aa) alone showed a suppression ratio of 55%, and when this peptide was used in combination with PHB2 peptides surrounding No. 1 (11-22aa), the combination with No. 1 (11-22aa) almost completely suppressed the growth, and the combinations with any of the peptides consisting of a region of 5 to 26 aa (Nos. 36, 37, 38, 39, and 40) showed a suppression ratio of 90% or higher (FIG. 1E). This suggested the importance of the PHB2 regions of No. 1 (11-22aa) and No. 5 (76-90aa) for the binding to BIG3 and the necessity to develop dominant-negative peptides considering these regions.

Suppressive Effects of PHB2 Sequence-Derived Peptides on E2-Dependent Growth

Next, the suppressive effect on E2-dependent growth of MCF-7 was examined when the two types of PHB2 sequence-derived peptides (No. 1 and No. 5), which can suppress E2-dependent growth of MCF-7, were used in combination. As a result, compared to each treatment with No. 1 or No. 5 alone, the use of both peptides in combination enhanced the effect and showed the growth suppressive effect of 88% (FIG. 2A). Moreover, enhanced suppressive effects were not observed when No. 5 was treated in combination with No. 6 (86-100aa), which did not show suppressive effect (suppression ratio of about 10%) in treatment with No. 6 alone. This suggested that there may be a BIG3-binding region in each of 11-22 aa and 76-90 aa of PHB2.

Next, the inhibition of the binding between BIG3 and PHB2 by treatment with 20 µM and 50 µM of No. 1 or No. 5 was examined by immunoprecipitation with a BIG3 antibody. As a result, No. 1 and No. 5 both inhibited the binding between BIG3 and PHB2 in a concentration-dependent manner, and No. 1 and No. 5 showed inhibition ratios of 64% and 80%, respectively, at 50 µM (FIG. 2B). Furthermore, the use of both peptides at 50 µM in combination achieved the inhibition ratio of 87% (FIG. 2B). Next, the effect of each peptide (Nos. 1, 5, and 6) on Ser39 phosphorylation of PHB2 was examined. Compared to Ser39 phosphorylation of PHB2 by treatment with ERAP, a positive control, each treatment with No. 1 or No. 5 alone showed only 40% or 20% band intensity of phosphorylation (FIG. 2C), and even the use of both peptides in combination showed 70% intensity of phosphorylation (FIG. 2C). On the other hand, No. 6 showed 10% band intensity of PHB2 phosphorylation and could hardly induce the phosphorylation (FIG. 2C). Moreover, since even the use of No. 5 and No. 6 in combination showed 20% band intensity, it was suggested that the binding between PHB2 and BIG3 extends over multiple regions of No. 1 and No. 5.

Suppressive Effect of a Novel Peptide (11-90aa) Covering the BIG3-Binding Regions of PHB2 Peptides No. 1 and No. 5 on E2-Dependent Growth Since the PHB2 sequence-derived peptides (No. 1 and No. 5) can suppress E2-dependent growth and can induce Ser39 phosphorylation of PHB2 by only 50%, a PHB2 peptide of 11-90aa comprising these two regions was newly synthesized and its effect on E2-dependent growth of MCF-7 was examined. As a result, the PHB2 peptide 11-90aa suppressed MCF-7 which proliferated twofold by 24 hour-E2 stimulation in a concentration-dependent manner, but had a suppression ratio of only 57% even at 50 μM (FIG. 3A), which ratio was almost the same as that of No. 1 and No. 5 peptides.

Figures 3A, 3B, 3C:
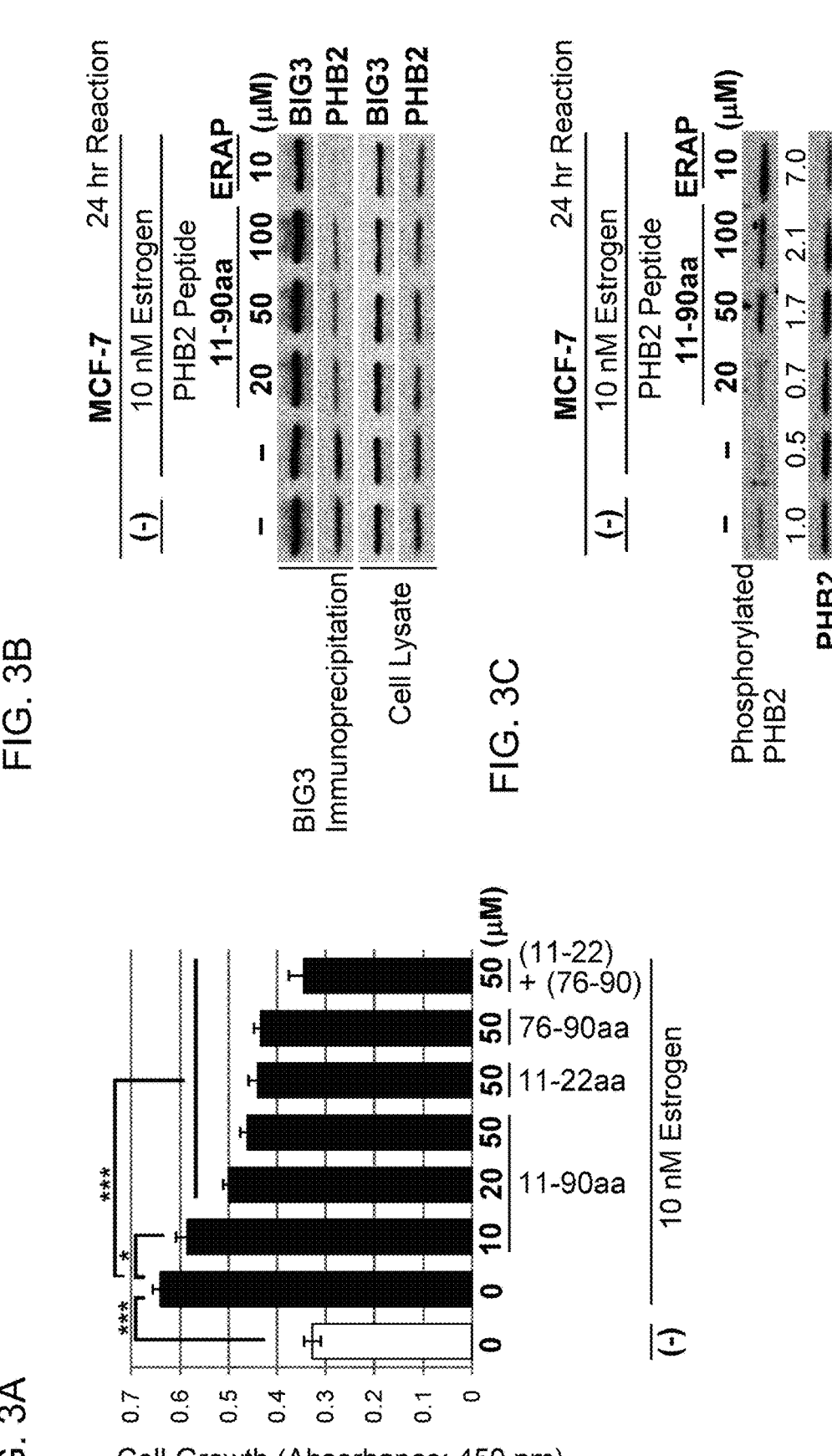
FIGS. 3A-3C show the effect of PHB2 peptide 11-90aa on estrogen-dependent growth and on the interaction between BIG3 and PHB2.

It was then evaluated whether the peptide 11-90aa can inhibit the binding between BIG3 and PHB2 and can induce PHB2 phosphorylation. As a result, the PHB2 peptide 11-90aa inhibited the binding between BIG3 and PHB2 greater than an untreated sample, but did not provide a sufficient effect of inhibiting the binding (FIG. 3B). Furthermore, Ser39 phosphorylation of PHB2 was induced in a manner dependent on the concentration of PHB2 peptide 11-90aa, but it was 30% of the phosphorylation obtained by ERAP treatment, and PHB2 peptide 11-90aa could not induce sufficient phosphorylation (FIG. 3C). This may be because the number of amino acids was large, i.e. 80, and thus the binding to the α-helical structure of BIG3 was insufficient.

Suppressive Effects of Linear, Branched, and Cyclic PHB2 on E2-Dependent Growth

Since the combination of PHB2 sequence-derived peptides 11-22aa and 76-90aa enhanced suppression of estrogen-dependent growth to achieve a suppression ratio of 88% (FIG. 2A), a peptide in which both sequences were synthesized linearly (linear bound type; FIG. 4A), a peptide in which both sequences were synthesized with branching (branched bound type; FIG. 4B), and peptides in which each sequence was synthesized in a cyclic form for stabilizing structure and improving membrane permeability (cyclic type; FIG. 4C) were additionally prepared, and the enhancement of the growth suppressive effect of each peptide was examined (treated with 10 μM each peptide for 24 hours). As a result, the linear bound and branched bound PHB2 peptides, in which both sequences were linked via a PEG (polyethylene glycol) sequence, showed suppression ratios of 71% and 57%, respectively. These suppression ratios were enhanced compared to that of administration of a single linear peptide, but were lower than that of the use of the peptides in combination (FIG. 5A). Furthermore, cyclic PHB2 peptides of 11-21aa and 76-88aa showed enhanced suppression ratios compared to non-cyclic peptides (FIG. 5A). Moreover, the use of the cyclic peptides in combination achieved an almost complete suppressive effect (suppression ratio of 96%; FIG. 5A), but an apoptosis-like phenomenon in which cells floated could not be confirmed.

Next, the effects of the cyclic peptides on growth of normal mammary gland epithelial cells, MCF-10A, which do not express ERα and BIG3, were examined (treated with 10 μM each peptide for 24 hours). As a result, although little suppressive effects were observed in the linear bound and cyclic bound PHB2 peptides (FIG. 5B; linear bound type: inhibition ratio of 10%, cyclic 11-21aa: inhibition ratio of 14%, cyclic 76-88aa: inhibition ratio of 15%), it was suggested that most PHB2 peptides specifically suppress E2-dependent growth with little effect on MCF-10A growth.

Subsequently, it was examined whether these PHB2 peptides can inhibit the interaction between BIG3 and PHB2. As a result, BIG3 strongly bound to PHB2 when the cells were untreated or stimulated with E2 (FIG. 5C) and treatment with each PHB2 peptide alone could hardly inhibit the interaction between BIG3 and PHB2 (FIG. 5C); however, the respective combination of the linear PHB2 peptides and the cyclic PHB2 peptides could markedly inhibit the interaction (FIG. 5C; combination of linear type: inhibition ratio of 67%, combination of cyclic type: inhibition ratio of 81%), and these results suggested that there are two BIG3-binding regions on PHB2. On the other hand, it was judged that the linear bound and branched bound PHB2 peptides cannot cover two BIG3-binding regions on PHB2.

Long-Term Stability of the Suppressive Effects of Cyclic PHB2 Peptides on E2-Dependent Growth Since it was suggested that cyclic PHB2 peptides may acquire low concentration and long-term stability due to enhanced membrane permeability and fixation of structure, the long-term stability for up to 96 hours was examined when cells were treated with 10 μM each cyclic PHB2 peptide alone. As a result, the linear PHB2 peptides 11-22aa and 76-90aa showed suppression ratios of 40% and 61%, respectively, in a 24-hour treatment, but exhibited significantly decreased suppression ratios of 31% and 24%, respectively, after 96 hours (FIG. 6A). Meanwhile, the cyclic peptide 11-21aa and cyclic peptide 76-88aa showed suppression ratios of 67% (53% in a 24-hour treatment) and 72% (58% in a 24-hour treatment), respectively, even after 96 hours (FIG. 6A), and their suppressive effects stably lasted for up to 96 hours. It was considered from these data that the suppressive effects of the cyclic peptides could last for a long time due to stable fixation of their tertiary structure similar to the cross-linked peptides.

Next, since the cyclic PHB2 peptides could sustain their suppressive effects for up to 96 hours, the effect on growth of MCF-10A, which does not express ERα and BIG3, was examined by treating with 1 μM or 10 μM each cyclic PHB2 peptide for up to 96 hours. As a result, the cyclic peptides of PHB2 sequences 11-21 aa and 76-88 aa each had little effect at 1 μM (both of them had suppression ratios of 5% to 7%), but showed suppression ratios of 10% to 15% at 10 μM (FIG. 6B), suggesting that they have a small non-specific suppressive effect. However, it was considered that the suppression of E2-dependent growth of MCF-7 by the cyclic PHB2 peptides was mainly due to the inhibition of the binding between BIG3 and PHB2.

Concentration-Dependent Suppressive Effect of Cyclic PHB2 Peptides on E2-Dependent Growth The 50% inhibition concentrations ($IC_{50}$) of the cyclic PHB2 peptides for E2-dependent growth of MCF-7 were calculated and a synergistic suppressive effect of the peptides at the $IC_{50}$ was examined. As a result, each cyclic PHB2 peptide suppressed E2-dependent growth in a concentration-dependent manner, and the cyclic 11-21aa and cyclic 76-88aa showed $IC_{50}$ values of 4.06 μM and 2.11 μM, respectively (FIG. 7A). Then, 4 μM cyclic 11-21aa and 2 μM cyclic 76-88aa were used to examine the effect of long-term combination, and the use of peptides in combination for 24 hours showed a synergistic suppressive effect of 82%, which effect lasted for up to 96 hours (FIG. 7B; combination: suppression ratio of 88%, cyclic 11-21aa: suppression ratio of 41%, cyclic 76-88aa: suppression ratio of 59%). Furthermore, the peptides at these concentrations had little effect on growth of MCF-10A (FIG. 7C).

Identification of Amino Acids in PHB2 Peptide Sequences that are Important for the Binding to BIG3

Since PHB2-derived peptides No. 1 (11-22aa: SEQ ID NO: 1) and No. 5 (76-90aa: SEQ ID NO: 5) had a suppressive effect by about 50% on E2-dependent growth, peptides were made in which each amino acid in the peptide sequences of No. 1 and No. 5 was mutated to alanine (FIG. 8A) to identify amino acids important for growth suppression. In the experiment, MCF-7 was seeded, 10 μM each PHB2 peptide and 10 nM estrogen were added 48 hours after seeding, and the cell number was monitored after another 24 hours. First, the amino acids of PHB2 sequence 11-22 aa were evaluated and No. 1 (11-22aa) suppressed estrogen-dependent cell growth by up to 65%, while only alanine-mutated peptides No. 59 and No. 62 (SEQ ID NOs: 59 and 62) attenuated suppression ratios of 19% and 8%, respectively (FIG. 8B). On the other hand, since other alanine-mutated peptides showed almost the same suppression ratio as No. 1 (FIG. 8B), glycines at positions 15 and 18 were considered to be important for the binding to BIG3, suggesting that the suppressive activity may be improved by converting these positions into an isomeric form, a D-amino acid.

Next, the amino acids of PHB2 sequence 76-90 aa were evaluated. Although the suppression ratio of No. 5 (76-90aa) on estrogen-dependent growth was 54% and nearly reproduced (FIG. 8C), the suppression ratios of alanine-mutated peptides Nos. 71 to 73 (SEQ ID NOs: 71 to 73) attenuated below No. 5 (76-90aa) and were 38%, 37%, and 13%, respectively (FIG. 8C), and particularly aspartic acid at position 82 was considered to be necessary for the binding between BIG3 and PHB2.

Figures 8D, 8E:
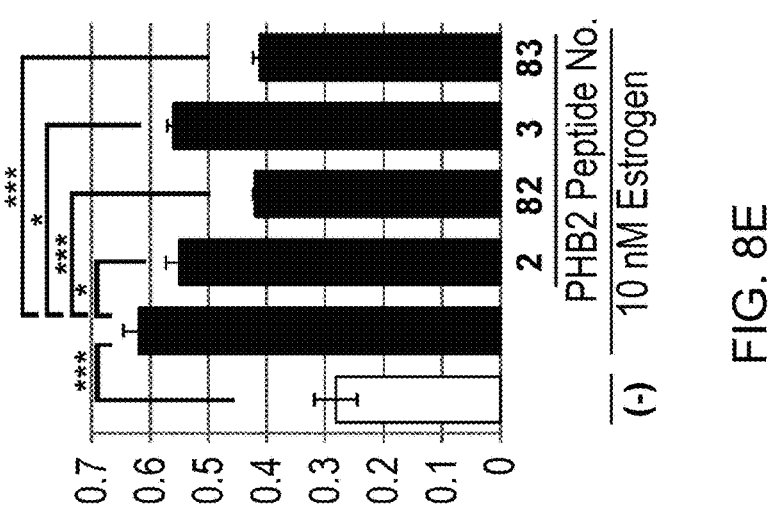
FIG. 8D depicts PHB2 peptides in which 51-57 aa has been added to PHB2 peptides No. 2 (42-50aa) and No. 3 (38-50aa).
FIG. 8E: The PHB2 sequence-derived peptides of FIG. 8D were each added at 10 μM, and the cells were immediately stimulated with 10 nM estrogen to evaluate the cell number for 24 hours by MTT assay. The data represents mean±standard deviation of three independent experiments.

Furthermore, peptides (FIG. 8D; Nos. 82 and 83 (SEQ ID NOs: 82 and 83)) were prepared by adding 51-57aa comprising 53-57 aa, which was predicted to be involved in the interaction between BIG3 and PHB2 by in silico analysis (FIG. 1A), to No. 2 (42-50aa: SEQ ID NO: 2) and to No. 3 (38-50aa: SEQ ID NO: 3), which showed a suppressive effect other than peptides No. 1 (11-22aa) and No. 5 (76-90aa), and these peptides were used to examine the effects on estrogen-dependent cell growth. As a result, while the suppression ratios of No. 2 and No. 3 were 20% and 17%, respectively, peptides No. 82 and No. 83, to which the amino acids at positions up to 57 were added, showed improved suppression ratios of 59% and 61%, respectively (FIG. 8E). Thus, it was suggested that by having the amino acids from glutamic acid at position 44 to glycine at position 57, the PHB2 peptides can be comparable in suppression ratio to No. 1 and No. 5.

[Example 2] Effects on Triple-Negative Breast Cancer

1. Materials and Methods
Cell lines and Culture Conditions
Human breast cancer cell line MDA-MB-231 was purchased from American Type Culture Collection (ATCC, Manassas, Va., USA), and cultured using Leibovitz's L-15 medium (Thermo Fisher Scientific) supplemented with 10% FBS (Thermo Fisher Scientific, Waltham, Mass., USA) and a 1% antibiotic/antimycotic solution (Wako Pure Chemical, Osaka, Japan) at 37° C. without $CO_2$ concentration control.
Cell Growth Assay
MDA-MB-231 cells were seeded into 48-well plates at a cell density of $1 \times 10^4$ cells/200 μL in well. 48 hours later, the medium in each well was exchanged to a medium supplemented with PHB2 peptides 11-22aa or 76-90aa (three-fold serial dilution from 20 μM), and after culturing for another 96 hours, the level of cell growth was measured using the Cell Counting Kit-8 (Dojindo, Kumamoto, Japan). Data were obtained from three independent experiments, a graph (mean±standard deviation) was produced using a graphing and data analyzing software SigmaPlot (Systat Software, San Jose, CA, USA), and the 50% inhibition concentration ($IC_{50}$) of the peptide against cell growth was calculated.
Combination Assay
MDA-MB-231 cells were seeded into 48-well plates at a cell density of $1 \times 10^4$ cells/200 μL in well. 48 hours later, the medium in each well was exchanged to media supplemented with PHB2 peptide 11-22aa (added concentration: $IC_{50}$ value), PHB2 peptide 76-90aa (added concentration: $IC_{50}$ value) and a mixed solution of both peptides (added concentration: respective $IC_{50}$ value), respectively, or to a medium supplemented with phosphate buffered saline (PBS) as a negative control. After culture for another 96 hours, the cell growth level was measured using the Cell Counting Kit-8 (Dojindo, Kumamoto, Japan). The data obtained was used to calculate relative values based on the growth level when PBS was added, and the graph was produced.
2. Results
Growth Suppressive Effects of PHB2 Peptides on a Breast Cancer Cell Line
To examine the cell growth suppressive effects of PHB2 peptides 11-22aa and 76-90aa on the breast cancer cell line MDA-MB-231, serial dilution series of the peptides were prepared and the growth level was measured 96 hours after addition to the cells. As a result, as shown in FIGS. 9A and 9B, concentration-dependent suppressive effects on cell growth were observed in both peptides. The 50% inhibition concentrations ($IC_{50}$) were 0.462 μM in the peptide 11-22aa and 0.273 μM in the peptide 76-90aa, and the peptide 76-90aa showed a more potent growth suppressive effect.
Effect of Use of PHB2 Peptides 11-22aa and 76-90aa in Combination
To examine the effect of use of PHB2 peptides 11-22aa and 76-90aa in combination on suppression of cell growth, the breast cancer cell line MDA-MB-231 was used to compare the cell growth levels when both peptides were mixed and added at respective $IC_{50}$ and when each peptide was added alone at respective $IC_{50}$. As a result, as shown in FIG. 9C, the addition of each peptide alone showed the suppression of growth by about 50% compared to when phosphate buffered saline (PBS), a negative control, was added; however, the combination enhanced the suppressive effect by about 62%.

[Example 3] Effects of Cross-Linking PHB2 Peptide on Estrogen-Dependent Breast Cancer 1. Materials and Methods
Cell lines and Culturing Conditions
Human breast cancer cell line MCF-7 was purchased from JCRB Cell Bank (Osaka, Japan) and maintained in MEM (Thermo Fisher Scientific) supplemented with 10% FBS (Nichirei Biosciences Inc., Tokyo, Japan), a 1% Antibiotic/Antimycotic solution (Thermo Fisher Scientific, Waltham, MA, USA), 0.1 mM NEAA (Thermo Fisher Scientific), 1 mM sodium pyruvate (Thermo Fisher Scientific), and 10 μg/mL insulin (Sigma, St. Louis, MO, USA) under 5% $CO_2$ at 37° C.
Normal mammary gland epithelial cell line MCF-10A was purchased from American Type Culture Collection (ATCC, Manassas, Va., USA), and maintained in MEBM (Lonza) supplemented with a Single Quots kit (BPE, hydrocortisone, hEGF, insulin, gentamycin/amphoterin-B)

(Lonza, Walkersville, MD, USA) and 100 ng/mL cholera toxin under 5% $CO_2$ at 37° C.

Cell Growth Assay

Growth assay on MCF-7 was carried out by seeding cells into 48-well plates ($2 \times 10^4$ cells/200 μL). First, on the next day after seeding, the medium was changed to phenol red-free DMEM/F12 (Thermo Fisher Scientific) supplemented with 10% FBS, 1% Antibiotic/Antimycotic solution, 0.1 mM NEAA, 1 mM sodium pyruvate, and 10 μg/mL insulin. 24 hours later, the cells were treated with 10 nM 17β-estradiol (estrogen, Sigma) alone or with 10 nM estrogen and a PHB2 sequence-derived peptide. Growth assay on MCF-10A was carried out by seeding cells into 48-well plates ($2 \times 10^4$ cells/200 μL). 24 hours after seeding, PHB2 sequence-derived peptide was added. Growth assays were carried out using the Cell Counting Kit-8 (CCK-8) (Dojindo, Kumamoto, Japan). The data are shown by mean±standard deviation of three independent experiments.

2. Results

Suppressive Effects of Cross-Linked PHB2 Peptides on Estrogen-Dependent Growth

PHB2 peptides 11-21aa and 76-88aa were cross-linked by three types of cross-linking methods (FIG. 10A: hexafluorobenzene cross-linking, decafluorobiphenyl cross-linking, and disulfide cross-linking) to prepare cross-linked PHB2 peptides (stapled PHB2 peptides) (FIG. 10B), and the suppressive effects of these peptides on estrogen-dependent growth were examined. In the experiment, breast cancer cells MCF-7 were seeded, 10 μM each PHB2 peptide and 10 nM estrogen were added after 48 hours, and the cell number was evaluated after another 24 hours by MTT assay.

Each cross-linked PHB2 peptide of 11-21aa and 76-88aa improved the suppressive effect on estrogen-dependent growth about 1.5-fold compared to non-cross-linked PHB2 peptides (SEQ ID NOs: 109, 113, 114, 118, and 122) (polyarginine addition: FIG. 10C (left); without polyarginine: FIG. 10C (right)). The improved effects did not vary depending on the cross-linking method (stapling method). Moreover, cross-linked PHB2 peptides which do not have polyarginine at the C terminus (SEQ ID NOs: 115, 116, 117, 119, 120, and 121) showed a slightly higher suppression ratios than peptides to which polyarginine was added (with polyarginine: suppression ratio of about 60%; without polyarginine: suppression ratio of about 70%), suggesting that polyarginine may block the function of cross-linked structure.

Suppressive Effects of Cyclic PHB2 Peptides on Estrogen-Dependent Growth

For improving the cell membrane permeability and the structural stability of cyclic PHB2 peptides (FIG. 4C, SEQ ID NOs: 25 and 26), their cross-linking forms were changed and the suppressive effects on estrogen-dependent growth were examined. In addition to disulfide cross-linking (SEQ ID NOs: 25 and 26) so far examined, hexafluorobenzene cross-linking (FIG. 11A; SEQ ID NOs: 123 and 126) and decafluorobiphenyl cross-linking (FIG. 11A; SEQ ID NOs: 124 and 127) were evaluated. As a result, cyclic PHB2 peptides cross-linked using fluorobenzene (FIG. 11A; SEQ ID NOs: 123, 124, 126, and 127) slightly improved the growth suppressive effect compared to disulfide cross-linking (FIG. 11B), and cyclic PHB2 peptide 11-21aa and cyclic PHB2 peptide 76-88aa enhanced the suppression ratios to about 70% and about 80%. Furthermore, no difference has been observed for fluorobenzene cross-linking between a single cross-linking (hexafluorobenzene cross-linking) and a double cross-linking (decafluorobiphenyl cross-linking).

Effects of Modifications of PHB2 Peptide 11-22aa on Estrogen-Dependent Growth

In the PHB2 peptide 11-22aa, glycines at positions 15 and 18 in the amino acid sequence of SEQ ID NO: 28 (full-length PHB2 polypeptide) were considered to be important for the binding to BIG3 (FIG. 8). Then, it was examined whether substitutions of these positions with D-alanine and D-leucine (FIG. 12A) enhance the suppressive activity or not. As a result, while the PHB2 peptide in which glycines at positions 15 and 18 were substituted with D-leucines (SEQ ID NO: 134) showed a suppression ratio of about 65% (FIG. 12B), the substitutions with D-alanines (SEQ ID NO: 133) had no suppressive effect (FIG. 12B). However, since the suppression ratio of PHB2 peptide 11-22aa (SEQ ID NO: 1; FIG. 8B) was about 65%, the substitutions with D-leucine showed little improvement in suppressive effect.

Effects of Cross-Linked PHB2 Peptides on Growth of Mammary Gland Epithelial Cells The effects of cross-linked and cyclic PHB2 peptides on growth of normal mammary gland epithelial cells MCF-10A, which do not express ERα and BIG3, were examined (treated with 10 μM each PHB2 peptide for 24 hours). As a result, all the PHB2 peptides evaluated had no effect on growth of MCF-10A (FIG. 13).

INDUSTRIAL APPLICABILITY

The present invention provides PHB2 amino acid sequence-derived peptides which exert an inhibitory effect on the BIG3-PHB2 interaction and are useful as therapeutic agents for breast cancer. The peptides provided by the present invention are useful in treating cancer such as breast cancer. More specifically, the peptides of the present invention are useful in treating BIG3-positive and/or estrogen receptor-positive cancer. The peptides of the present invention target not PHB2, whose expression is observed in organs throughout the human body, but BIG3, which is a protein highly expressed specifically in particularly estrogen receptor-positive cancer, and thus these peptides can be expected to have high selectivity for estrogen receptor-positive cancer. Moreover, the peptides of the present invention also exert an antitumor effect against triple-negative breast cancer.

The invention claimed is:

1. A cyclic peptide, comprising a site binding to a BIG3 polypeptide in a PHB2 polypeptide, wherein the cyclic peptide inhibits the binding between the PHB2 polypeptide and the BIG3 polypeptide, wherein the cyclic peptide consists of an amino acid sequence selected from the group consisting of SEQ ID NOs: 25, 123, 124, 106 to 108, and 115 to 117, and wherein the cyclic peptide comprises a single intramolecular crosslink between the two cysteine residues.

2. The cyclic peptide of claim 1, wherein the cyclic peptide has either or both of the following properties (i) and (ii):

(i) suppressing growth of BIG3-positive cells; and
(ii) promoting phosphorylation of a serine residue in the PHB2 polypeptide in BIG3-positive cells.

3. A pharmaceutical composition comprising: at least one ingredient selected from the group consisting of one or more of the cyclic peptides of claim 1, and a pharmaceutically acceptable salt(s) of the peptide(s); and a pharmaceutically acceptable carrier.

4. The cyclic peptide of claim 1, wherein the single intramolecular crosslink is a hexafluorobenzene crosslink.

5. The cyclic peptide of claim 1, wherein the single intramolecular crosslink is a decafluorobiphenyl crosslink.

6. The cyclic peptide of claim 1, wherein the single intramolecular crosslink is a disulfide crosslink.

* * * * *

SEQUENCE LISTING

```
<160> NUMBER OF SEQ ID NOS: 136

<210> SEQ ID NO 1
<211> LENGTH: 12
<212> TYPE: PRT
<213> ORGANISM: Artificial Sequence
<220> FEATURE:
<223> OTHER INFORMATION: PHB2 peptide No. 1
```

```
<400> SEQUENCE: 1

Arg Leu Pro Ala Gly Pro Arg Gly Met Gly Thr Ala
1               5                   10

<210> SEQ ID NO 2
<211> LENGTH: 9
<212> TYPE: PRT
<213> ORGANISM: Artificial Sequence
<220> FEATURE:
<223> OTHER INFORMATION: PHB2 peptide No. 2

<400> SEQUENCE: 2

Thr Val Glu Gly Gly His Arg Ala Ile
1               5

<210> SEQ ID NO 3
<211> LENGTH: 13
<212> TYPE: PRT
<213> ORGANISM: Artificial Sequence
<220> FEATURE:
<223> OTHER INFORMATION: PHB2 peptide No. 3

<400> SEQUENCE: 3

Glu Ser Val Phe Thr Val Glu Gly Gly His Arg Ala Ile
1               5                   10

<210> SEQ ID NO 4
<211> LENGTH: 17
<212> TYPE: PRT
<213> ORGANISM: Artificial Sequence
<220> FEATURE:
<223> OTHER INFORMATION: PHB2 peptide No. 4

<400> SEQUENCE: 4

Tyr Gly Val Arg Glu Ser Val Phe Thr Val Glu Gly Gly His Arg Ala
1               5                   10                  15

Ile

<210> SEQ ID NO 5
<211> LENGTH: 15
<212> TYPE: PRT
<213> ORGANISM: Artificial Sequence
<220> FEATURE:
<223> OTHER INFORMATION: PHB2 peptide No. 5

<400> SEQUENCE: 5

Gln Tyr Pro Ile Ile Tyr Asp Ile Arg Ala Arg Pro Arg Lys Ile
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: PHB2 peptide No. 6

<400> SEQUENCE: 6

Arg Pro Arg Lys Ile Ser Ser Pro Thr Gly Ser Lys Asp Leu Gln
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: PHB2 peptide No. 7
```

-continued

<400> SEQUENCE: 7

Ser Lys Asp Leu Gln Met Val Asn Ile Ser Leu Arg Val Leu Ser
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: PHB2 peptide No. 8

<400> SEQUENCE: 8

Leu Arg Val Leu Ser Arg Pro Asn Ala Gln Glu Leu Pro Ser Met
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: PHB2 peptide No. 9

<400> SEQUENCE: 9

Glu Leu Pro Ser Met Tyr Gln Arg Leu Gly Leu Asp Tyr Glu Glu
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: PHB2 peptide No. 10

<400> SEQUENCE: 10

Leu Asp Tyr Glu Glu Arg Val Leu Pro Ser Ile Val Asn Glu Val
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: PHB2 peptide No. 11

<400> SEQUENCE: 11

Ile Val Asn Glu Val Leu Lys Ser Val Val Ala Lys Phe Asn Ala
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: PHB2 peptide No. 12

<400> SEQUENCE: 12

Ala Lys Phe Asn Ala Ser Gln Leu Ile Thr Gln Arg Ala Gln Val
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: PHB2 peptide No. 13

<400> SEQUENCE: 13

Gln Arg Ala Gln Val Ser Leu Leu Ile Arg Arg Glu Leu Thr Glu
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: PHB2 peptide No. 14

<400> SEQUENCE: 14

Arg Glu Leu Thr Glu Arg Ala Lys Asp Phe Ser Leu Ile Leu Asp
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: PHB2 peptide No. 15

<400> SEQUENCE: 15

Ser Leu Ile Leu Asp Asp Val Ala Ile Thr Glu Leu Ser Phe Ser
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: PHB2 peptide No. 16

<400> SEQUENCE: 16

Glu Leu Ser Phe Ser Arg Glu Tyr Thr Ala Ala Val Glu Ala Lys
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: PHB2 peptide No. 17

<400> SEQUENCE: 17

Ala Val Glu Ala Lys Gln Val Ala Gln Gln Glu Ala Gln Arg Ala
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: PHB2 peptide No. 18

<400> SEQUENCE: 18

Glu Ala Gln Arg Ala Gln Phe Leu Val Glu Lys Ala Lys Gln Glu
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: PHB2 peptide No. 19

<400> SEQUENCE: 19

```
Gln Phe Leu Val Glu Lys Ala Lys Gln Glu Gln Arg Gln Lys Ile
1               5                   10                  15
```

<210> SEQ ID NO 20
<211> LENGTH: 14
<212> TYPE: PRT
<213> ORGANISM: Artificial Sequence
<220> FEATURE:
<223> OTHER INFORMATION: PHB2 peptide No. 20

<400> SEQUENCE: 20

```
Phe Leu Val Glu Lys Ala Lys Gln Glu Gln Arg Gln Lys Ile
1               5                   10
```

<210> SEQ ID NO 21
<211> LENGTH: 80
<212> TYPE: PRT
<213> ORGANISM: Artificial Sequence
<220> FEATURE:
<223> OTHER INFORMATION: PHB2 derived peptide 11-90aa

<400> SEQUENCE: 21

```
Arg Leu Pro Ala Gly Pro Arg Gly Met Gly Thr Ala Leu Lys Leu Leu
1               5                   10                  15

Leu Gly Ala Gly Ala Val Ala Tyr Gly Val Arg Glu Ser Val Phe Thr
                20                  25                  30

Val Glu Gly Gly His Arg Ala Ile Phe Phe Asn Arg Ile Gly Gly Val
            35                  40                  45

Gln Gln Asp Thr Ile Leu Ala Glu Gly Leu His Phe Arg Ile Pro Trp
        50                  55                  60

Phe Gln Tyr Pro Ile Ile Tyr Asp Ile Arg Ala Arg Pro Arg Lys Ile
65                  70                  75                  80
```

<210> SEQ ID NO 22
<211> LENGTH: 12
<212> TYPE: PRT
<213> ORGANISM: Artificial Sequence
<220> FEATURE:
<223> OTHER INFORMATION: PHB2 derived peptide 11-22aa
<220> FEATURE:
<221> NAME/KEY: MOD_RES
<222> LOCATION: (1)..(1)
<223> OTHER INFORMATION: ACETYLATION

<400> SEQUENCE: 22

```
Arg Leu Pro Ala Gly Pro Arg Gly Met Gly Thr Ala
1               5                   10
```

<210> SEQ ID NO 23
<211> LENGTH: 23
<212> TYPE: PRT
<213> ORGANISM: Artificial Sequence
<220> FEATURE:
<223> OTHER INFORMATION: PHB2 derived peptide 76-90aa + 8 Arg residues
<220> FEATURE:
<221> NAME/KEY: MOD_RES
<222> LOCATION: (23)..(23)
<223> OTHER INFORMATION: AMIDATION

<400> SEQUENCE: 23

```
Gln Tyr Pro Ile Ile Tyr Asp Ile Arg Ala Arg Pro Arg Lys Ile Arg
1               5                   10                  15

Arg Arg Arg Arg Arg Arg Arg
                20
```

-continued

```
<210> SEQ ID NO 24
<211> LENGTH: 22
<212> TYPE: PRT
<213> ORGANISM: Artificial Sequence
<220> FEATURE:
<223> OTHER INFORMATION: PHB2 derived peptide 76-89aa + 8 Arg residues
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (22)..(22)
<223> OTHER INFORMATION: AMIDATION

<400> SEQUENCE: 24

Gln Tyr Pro Ile Ile Tyr Asp Ile Arg Ala Arg Pro Arg Lys Arg Arg
1               5                   10                  15

Arg Arg Arg Arg Arg Arg
            20

<210> SEQ ID NO 25
<211> LENGTH: 19
<212> TYPE: PRT
<213> ORGANISM: Artificial Sequence
<220> FEATURE:
<223> OTHER INFORMATION: cyclic peptide containing PHB2 derived peptide
      11-21aa
<220> FEATURE:
<221> NAME/KEY: DISULFID
<222> LOCATION: (1)..(13)
<220> FEATURE:
<221> NAME/KEY: MISC_FEATURE
<222> LOCATION: (10)..(10)
<223> OTHER INFORMATION: Xaa = Nle
<220> FEATURE:
<221> NAME/KEY: MISC_FEATURE
<222> LOCATION: (15)..(15)
<223> OTHER INFORMATION: Xaa = Nal

<400> SEQUENCE: 25

Cys Arg Leu Pro Ala Gly Pro Arg Gly Xaa Gly Thr Cys Phe Xaa Arg
1               5                   10                  15

Arg Arg Arg

<210> SEQ ID NO 26
<211> LENGTH: 21
<212> TYPE: PRT
<213> ORGANISM: Artificial Sequence
<220> FEATURE:
<223> OTHER INFORMATION: cyclic peptide containing PHB2 derived peptide
      76-88aa
<220> FEATURE:
<221> NAME/KEY: DISULFID
<222> LOCATION: (1)..(15)
<220> FEATURE:
<221> NAME/KEY: MISC_FEATURE
<222> LOCATION: (17)..(17)
<223> OTHER INFORMATION: Xaa = Nal

<400> SEQUENCE: 26

Cys Gln Tyr Pro Ile Ile Tyr Asp Ile Arg Ala Arg Pro Arg Cys Phe
1               5                   10                  15

Xaa Arg Arg Arg Arg
            20

<210> SEQ ID NO 27
<211> LENGTH: 1457
<212> TYPE: DNA
```

<213> ORGANISM: Homo sapiens
<220> FEATURE:
<221> NAME/KEY: CDS
<222> LOCATION: (211)..(1110)

<400> SEQUENCE: 27

```
tccgtatgcg cgattcctgt gcgcgaagtt cgggtccgta gtgggctaag ggggagggtt        60
tcaaagggag cgcacttccg ctgccctttc tttcgccagc cttacgggcc cgaaccctcg       120
tgtgaagggt gcagtaccta agccggagcg gggtagaggc gggccggcac ccccttctga       180
cctccagtgc cgccggcctc aagatcagac atg gcc cag aac ttg aag gac ttg       234
                                    Met Ala Gln Asn Leu Lys Asp Leu
                                     1               5 gcg gga cgg ctg ccc gcc ggg ccc cgg ggc atg ggc acg gcc ctg aag       282
Ala Gly Arg Leu Pro Ala Gly Pro Arg Gly Met Gly Thr Ala Leu Lys
     10              15              20 ctg ttg ctg ggg gcc ggc gcc gtg gcc tac ggt gtg cgc gaa tct gtg       330
Leu Leu Leu Gly Ala Gly Ala Val Ala Tyr Gly Val Arg Glu Ser Val
25              30              35              40 ttc acc gtg gaa ggc ggg cac aga gcc atc ttc ttc aat cgg atc ggt       378
Phe Thr Val Glu Gly Gly His Arg Ala Ile Phe Phe Asn Arg Ile Gly
             45              50              55 gga gtg cag cag gac act atc ctg gcc gag ggc ctt cac ttc agg atc       426
Gly Val Gln Gln Asp Thr Ile Leu Ala Glu Gly Leu His Phe Arg Ile
             60              65              70 cct tgg ttc cag tac ccc att atc tat gac att cgg gcc aga cct cga       474
Pro Trp Phe Gln Tyr Pro Ile Ile Tyr Asp Ile Arg Ala Arg Pro Arg
             75              80              85 aaa atc tcc tcc cct aca ggc tcc aaa gac cta cag atg gtg aat atc       522
Lys Ile Ser Ser Pro Thr Gly Ser Lys Asp Leu Gln Met Val Asn Ile
     90              95              100 tcc ctg cga gtg ttg tct cga ccc aat gct cag gag ctt cct agc atg       570
Ser Leu Arg Val Leu Ser Arg Pro Asn Ala Gln Glu Leu Pro Ser Met
105             110             115             120 tac cag cgc cta ggg ctg gac tac gag gaa cga gtg ttg ccg tcc att       618
Tyr Gln Arg Leu Gly Leu Asp Tyr Glu Glu Arg Val Leu Pro Ser Ile
             125             130             135 gtc aac gag gtg ctc aag agt gtg gtg gcc aag ttc aat gcc tca cag       666
Val Asn Glu Val Leu Lys Ser Val Val Ala Lys Phe Asn Ala Ser Gln
             140             145             150 ctg atc acc cag cgg gcc cag gta tcc ctg ttg atc cgc cgg gag ctg       714
Leu Ile Thr Gln Arg Ala Gln Val Ser Leu Leu Ile Arg Arg Glu Leu
             155             160             165 aca gag agg gcc aag gac ttc agc ctc atc ctg gat gat gtg gcc atc       762
Thr Glu Arg Ala Lys Asp Phe Ser Leu Ile Leu Asp Asp Val Ala Ile
     170             175             180 aca gag ctg agc ttt agc cga gag tac aca gct gct gta gaa gcc aaa       810
Thr Glu Leu Ser Phe Ser Arg Glu Tyr Thr Ala Ala Val Glu Ala Lys
185             190             195             200 caa gtg gcc cag cag gag gcc cag cgg gcc caa ttc ttg gta gaa aaa       858
Gln Val Ala Gln Gln Glu Ala Gln Arg Ala Gln Phe Leu Val Glu Lys
             205             210             215 gca aag cag gaa cag cgg cag aaa att gtg cag gcc gag ggt gag gcc       906
Ala Lys Gln Glu Gln Arg Gln Lys Ile Val Gln Ala Glu Gly Glu Ala
             220             225             230 gag gct gcc aag atg ctt gga gaa gca ctg agc aag aac cct ggc tac       954
Glu Ala Ala Lys Met Leu Gly Glu Ala Leu Ser Lys Asn Pro Gly Tyr
     235             240             245 atc aaa ctt cgc aag att cga gca gcc cag aat atc tcc aag acg atc      1002
Ile Lys Leu Arg Lys Ile Arg Ala Ala Gln Asn Ile Ser Lys Thr Ile
```

```
        250                 255                 260 gcc aca tca cag aat cgt atc tat ctc aca gct gac aac ctt gtg ctg      1050
Ala Thr Ser Gln Asn Arg Ile Tyr Leu Thr Ala Asp Asn Leu Val Leu
265                 270                 275                 280 aac cta cag gat gaa agt ttc acc agg gga agt gac agc ctc atc aag      1098
Asn Leu Gln Asp Glu Ser Phe Thr Arg Gly Ser Asp Ser Leu Ile Lys
                285                 290                 295 ggt aag aaa tga gcctagtcac caagaactcc accccagag gaagtggatc          1150
Gly Lys Lys tgcttctcca gttttgagg agccagccag gggtccagca cagccctacc ccgccccagt    1210
atcatgcgat ggtcccccac accggttccc tgaacccctc ttggattaag gaagactgaa   1270
gactagcccc ttttctgggg aattactttc ctcctccctg tgttaactgg ggctgttggg   1330
gacagtgcgt gatttctcag tgatttccta cagtgttgtt ccctccctca aggctgggag   1390
gagataaaca ccaacccagg aattctcaat aaatttttat tacttaacct gaaaaaaaaa   1450
aaaaaaa                                                             1457
```

```
<210> SEQ ID NO 28
<211> LENGTH: 299
<212> TYPE: PRT
<213> ORGANISM: Homo sapiens

<400> SEQUENCE: 28

Met Ala Gln Asn Leu Lys Asp Leu Ala Gly Arg Leu Pro Ala Gly Pro
1                 5                   10                  15

Arg Gly Met Gly Thr Ala Leu Lys Leu Leu Leu Gly Ala Gly Ala Val
                20                  25                  30

Ala Tyr Gly Val Arg Glu Ser Val Phe Thr Val Glu Gly Gly His Arg
            35                  40                  45

Ala Ile Phe Phe Asn Arg Ile Gly Gly Val Gln Gln Asp Thr Ile Leu
        50                  55                  60

Ala Glu Gly Leu His Phe Arg Ile Pro Trp Phe Gln Tyr Pro Ile Ile
65                  70                  75                  80

Tyr Asp Ile Arg Ala Arg Pro Arg Lys Ile Ser Ser Pro Thr Gly Ser
                85                  90                  95

Lys Asp Leu Gln Met Val Asn Ile Ser Leu Arg Val Leu Ser Arg Pro
            100                 105                 110

Asn Ala Gln Glu Leu Pro Ser Met Tyr Gln Arg Leu Gly Leu Asp Tyr
        115                 120                 125

Glu Glu Arg Val Leu Pro Ser Ile Val Asn Glu Val Leu Lys Ser Val
    130                 135                 140

Val Ala Lys Phe Asn Ala Ser Gln Leu Ile Thr Gln Arg Ala Gln Val
145                 150                 155                 160

Ser Leu Leu Ile Arg Arg Glu Leu Thr Glu Arg Ala Lys Asp Phe Ser
                165                 170                 175

Leu Ile Leu Asp Asp Val Ala Ile Thr Glu Leu Ser Phe Ser Arg Glu
            180                 185                 190

Tyr Thr Ala Ala Val Glu Ala Lys Gln Val Ala Gln Gln Glu Ala Gln
        195                 200                 205

Arg Ala Gln Phe Leu Val Glu Lys Ala Lys Gln Glu Gln Arg Gln Lys
    210                 215                 220

Ile Val Gln Ala Glu Gly Glu Ala Glu Ala Ala Lys Met Leu Gly Glu
225                 230                 235                 240

Ala Leu Ser Lys Asn Pro Gly Tyr Ile Lys Leu Arg Lys Ile Arg Ala
```

```
                    245                   250                   255

Ala Gln Asn Ile Ser Lys Thr Ile Ala Thr Ser Gln Asn Arg Ile Tyr
                    260                   265                   270

Leu Thr Ala Asp Asn Leu Val Leu Asn Leu Gln Asp Glu Ser Phe Thr
            275                   280                   285

Arg Gly Ser Asp Ser Leu Ile Lys Gly Lys Lys
        290                   295

<210> SEQ ID NO 29
<211> LENGTH: 1343
<212> TYPE: DNA
<213> ORGANISM: Homo sapiens
<220> FEATURE:
<221> NAME/KEY: CDS
<222> LOCATION: (211)..(996)

<400> SEQUENCE: 29
tccgtatgcg cgattcctgt gcgcgaagtt cgggtccgta gtgggctaag ggggagggtt        60
tcaaagggag cgcacttccg ctgccctttc tttcgccagc cttacgggcc cgaaccctcg       120
tgtgaagggt gcagtaccta agccggagcg gggtagaggc gggccggcac ccccttctga       180
cctccagtgc cgccggcctc aagatcagac atg gcc cag aac ttg aag gac ttg       234
                                    Met Ala Gln Asn Leu Lys Asp Leu
                                    1               5 gcg gga cgg ctg ccc gcc ggg ccc cgg ggc atg ggc acg gcc ctg aag       282
Ala Gly Arg Leu Pro Ala Gly Pro Arg Gly Met Gly Thr Ala Leu Lys
    10                  15                  20 ctg ttg ctg ggg gcc ggc gcc gtg gcc tac ggt gtg cgc gaa tct gtg       330
Leu Leu Leu Gly Ala Gly Ala Val Ala Tyr Gly Val Arg Glu Ser Val
25                  30                  35                  40 ttc acc gtg gaa ggc ggg cac aga gcc atc ttc ttc aat cgg atc ggt       378
Phe Thr Val Glu Gly Gly His Arg Ala Ile Phe Phe Asn Arg Ile Gly
                45                  50                  55 gga gtg cag cag gac act atc ctg gcc gag ggc ctt cac ttc agg atc       426
Gly Val Gln Gln Asp Thr Ile Leu Ala Glu Gly Leu His Phe Arg Ile
            60                  65                  70 cct tgg ttc cag tac ccc att atc tat gac att cgg gcc aga cct cga       474
Pro Trp Phe Gln Tyr Pro Ile Ile Tyr Asp Ile Arg Ala Arg Pro Arg
        75                  80                  85 aaa atc tcc tcc cct aca ggc tcc aaa gac cta cag atg gtg aat atc       522
Lys Ile Ser Ser Pro Thr Gly Ser Lys Asp Leu Gln Met Val Asn Ile
        90                  95                  100 tcc ctg cga gtg ttg tct cga ccc aat gct cag gag ctt cct agc atg       570
Ser Leu Arg Val Leu Ser Arg Pro Asn Ala Gln Glu Leu Pro Ser Met
105                 110                 115                 120 tac cag cgc cta ggg ctg gac tac gag gaa cga gtg ttg ccg tcc att       618
Tyr Gln Arg Leu Gly Leu Asp Tyr Glu Glu Arg Val Leu Pro Ser Ile
                125                 130                 135 gtc aac gag gtg ctc aag agt gtg gtg gcc aag ttc aat gcc tca cag       666
Val Asn Glu Val Leu Lys Ser Val Val Ala Lys Phe Asn Ala Ser Gln
            140                 145                 150 ctg atc acc cag cgg gcc cag gta tcc ctg ttg atc cgc cgg gag ctg       714
Leu Ile Thr Gln Arg Ala Gln Val Ser Leu Leu Ile Arg Arg Glu Leu
        155                 160                 165 aca gag agg gcc aag gac ttc agc ctc atc ctg gat gat gtg gcc atc       762
Thr Glu Arg Ala Lys Asp Phe Ser Leu Ile Leu Asp Asp Val Ala Ile
    170                 175                 180 aca gag ctg agc ttt agc cga gag tac aca gct gct gta gaa gcc aaa       810
Thr Glu Leu Ser Phe Ser Arg Glu Tyr Thr Ala Ala Val Glu Ala Lys
185                 190                 195                 200
```

-continued

```
caa gtg gca ctg agc aag aac cct ggc tac atc aaa ctt cgc aag att        858
Gln Val Ala Leu Ser Lys Asn Pro Gly Tyr Ile Lys Leu Arg Lys Ile
                205                 210                 215 cga gca gcc cag aat atc tcc aag acg atc gcc aca tca cag aat cgt        906
Arg Ala Ala Gln Asn Ile Ser Lys Thr Ile Ala Thr Ser Gln Asn Arg
                220                 225                 230 atc tat ctc aca gct gac aac ctt gtg ctg aac cta cag gat gaa agt        954
Ile Tyr Leu Thr Ala Asp Asn Leu Val Leu Asn Leu Gln Asp Glu Ser
                235                 240                 245 ttc acc agg gga agt gac agc ctc atc aag ggt aag aaa tga              996
Phe Thr Arg Gly Ser Asp Ser Leu Ile Lys Gly Lys Lys
                250                 255                 260 gcctagtcac caagaactcc acccccagag gaagtggatc tgcttctcca gttttttgagg    1056 agccagccag gggtccagca cagccctacc ccgcccagt atcatgcgat ggtcccccac      1116
accggttccc tgaacccctc ttggattaag gaagactgaa gactagcccc ttttctgggg     1176
aattactttc ctcctccctg tgttaactgg ggctgttggg gacagtgcgt gatttctcag     1236
tgatttccta cagtgttgtt ccctccctca aggctgggag gagataaaca ccaacccagg     1296
aattctcaat aaattttttat tacttaacct gaaaaaaaaa aaaaaaa                  1343
```

```
<210> SEQ ID NO 30
<211> LENGTH: 261
<212> TYPE: PRT
<213> ORGANISM: Homo sapiens

<400> SEQUENCE: 30

Met Ala Gln Asn Leu Lys Asp Leu Ala Gly Arg Leu Pro Ala Gly Pro
1               5                   10                  15

Arg Gly Met Gly Thr Ala Leu Lys Leu Leu Leu Gly Ala Gly Ala Val
                20                  25                  30

Ala Tyr Gly Val Arg Glu Ser Val Phe Thr Val Glu Gly Gly His Arg
            35                  40                  45

Ala Ile Phe Phe Asn Arg Ile Gly Gly Val Gln Gln Asp Thr Ile Leu
        50                  55                  60

Ala Glu Gly Leu His Phe Arg Ile Pro Trp Phe Gln Tyr Pro Ile Ile
65                  70                  75                  80

Tyr Asp Ile Arg Ala Arg Pro Arg Lys Ile Ser Ser Pro Thr Gly Ser
                85                  90                  95

Lys Asp Leu Gln Met Val Asn Ile Ser Leu Arg Val Leu Ser Arg Pro
                100                 105                 110

Asn Ala Gln Glu Leu Pro Ser Met Tyr Gln Arg Leu Gly Leu Asp Tyr
                115                 120                 125

Glu Glu Arg Val Leu Pro Ser Ile Val Asn Glu Val Leu Lys Ser Val
            130                 135                 140

Val Ala Lys Phe Asn Ala Ser Gln Leu Ile Thr Gln Arg Ala Gln Val
145                 150                 155                 160

Ser Leu Leu Ile Arg Arg Glu Leu Thr Glu Arg Ala Lys Asp Phe Ser
                165                 170                 175

Leu Ile Leu Asp Asp Val Ala Ile Thr Glu Leu Ser Phe Ser Arg Glu
                180                 185                 190

Tyr Thr Ala Ala Val Glu Ala Lys Gln Val Ala Leu Ser Lys Asn Pro
            195                 200                 205

Gly Tyr Ile Lys Leu Arg Lys Ile Arg Ala Ala Gln Asn Ile Ser Lys
        210                 215                 220
```

```
Thr Ile Ala Thr Ser Gln Asn Arg Ile Tyr Leu Thr Ala Asp Asn Leu
225                 230                 235                 240

Val Leu Asn Leu Gln Asp Glu Ser Phe Thr Arg Gly Ser Asp Ser Leu
                245                 250                 255

Ile Lys Gly Lys Lys
            260

<210> SEQ ID NO 31
<211> LENGTH: 14895
<212> TYPE: DNA
<213> ORGANISM: Homo sapiens
<220> FEATURE:
<221> NAME/KEY: CDS
<222> LOCATION: (172)..(6705)

<400> SEQUENCE: 31
gtggcccgcg gcatggagcg ggcgtgattc atcagcatcc gcgccggggc ggcatggggg      60
cgcgcgcggc ggccgcctag gcgcccaggg ccaggcagcg gcggcttccc cggcccggct     120
cgcccgcgct tctctccctg tgggcggcgg cccggcgcct ggaaggtcaa g atg gaa     177
                                                          Met Glu
                                                            1 gaa atc ctg agg aag ctg cag aag gag gcg tcc ggg agc aag tac aaa     225
Glu Ile Leu Arg Lys Leu Gln Lys Glu Ala Ser Gly Ser Lys Tyr Lys
        5                  10                  15 gcc atc aag gag agc tgc acc tgg gcc ctg gaa act cta ggt ggt ctg     273
Ala Ile Lys Glu Ser Cys Thr Trp Ala Leu Glu Thr Leu Gly Gly Leu
    20                  25                  30 gat acc att gtc aag atc cct cca cat gta ctg agg gag aaa tgc ctg     321
Asp Thr Ile Val Lys Ile Pro Pro His Val Leu Arg Glu Lys Cys Leu
35                  40                  45                  50 ctg cct ctc cag ttg gct ttg gaa tcc aag aat gtg aag ctg gcc caa     369
Leu Pro Leu Gln Leu Ala Leu Glu Ser Lys Asn Val Lys Leu Ala Gln
                55                  60                  65 cat gct ttg gca ggg atg cag aag ctt ctg tcg gaa gag agg ttt gta     417
His Ala Leu Ala Gly Met Gln Lys Leu Leu Ser Glu Glu Arg Phe Val
            70                  75                  80 tcc atg gaa aca gat tct gat gag aag cag ctg ctc aat cag ata ctg     465
Ser Met Glu Thr Asp Ser Asp Glu Lys Gln Leu Leu Asn Gln Ile Leu
            85                  90                  95 aat gcc gtg aaa gtg acg cct tcg ctc aac gag gac ctg cag gtg gaa     513
Asn Ala Val Lys Val Thr Pro Ser Leu Asn Glu Asp Leu Gln Val Glu
        100                 105                 110 gtg atg aag gtt tta cta tgc atc acc tac acg cca aca ttt gat ctg     561
Val Met Lys Val Leu Leu Cys Ile Thr Tyr Thr Pro Thr Phe Asp Leu
115                 120                 125                 130 aat ggg agt gcc gtg ctg aag atc gcg gag gtg tgc att gag acg tac     609
Asn Gly Ser Ala Val Leu Lys Ile Ala Glu Val Cys Ile Glu Thr Tyr
                135                 140                 145 ata agc agc tgt cac cag cgt agc ata aac act gct gtg cgg gca act     657
Ile Ser Ser Cys His Gln Arg Ser Ile Asn Thr Ala Val Arg Ala Thr
            150                 155                 160 ctc agt caa atg ctg agt gac ttg act tta cag tta cga cag agg cag     705
Leu Ser Gln Met Leu Ser Asp Leu Thr Leu Gln Leu Arg Gln Arg Gln
        165                 170                 175 gag aat acg ata att gaa aac cca gat gtc cca cag gat ttc ggg aat     753
Glu Asn Thr Ile Ile Glu Asn Pro Asp Val Pro Gln Asp Phe Gly Asn
        180                 185                 190 caa ggg tca aca gta gag tcc ctc tgt gat gat gtt gtc tct gta ctc     801
Gln Gly Ser Thr Val Glu Ser Leu Cys Asp Asp Val Val Ser Val Leu
195                 200                 205                 210
```

-continued

```
acc gtc ctg tgt gag aag ctg caa gcc gcc ata aat gac agc cag cag      849
Thr Val Leu Cys Glu Lys Leu Gln Ala Ala Ile Asn Asp Ser Gln Gln
                215             220             225 ctg cag ctt ctc tac ctg gag tgc atc ctg tct gtg ctc agc agc tcc      897
Leu Gln Leu Leu Tyr Leu Glu Cys Ile Leu Ser Val Leu Ser Ser Ser
                230             235             240 tcc tcc tcc atg cac ctg cac agg cgc ttc acg gac ctg atc tgg aaa      945
Ser Ser Ser Met His Leu His Arg Arg Phe Thr Asp Leu Ile Trp Lys
                245             250             255 aac ctc tgc cct gct ctc atc gtg atc ttg ggg aat cca att cat gac      993
Asn Leu Cys Pro Ala Leu Ile Val Ile Leu Gly Asn Pro Ile His Asp
        260             265             270 aaa acc atc acc tct gct cac acc agc agc acc agt acc agc ctg gag     1041
Lys Thr Ile Thr Ser Ala His Thr Ser Ser Thr Ser Thr Ser Leu Glu
275             280             285             290 tcg gac tct gcg tct ccg gga gtg tct gac cac ggc cga gga tca ggc     1089
Ser Asp Ser Ala Ser Pro Gly Val Ser Asp His Gly Arg Gly Ser Gly
                295             300             305 tgc tcc tgc act gcg ccg gcc ctg agc gga cct gtg gct cgg act atc     1137
Cys Ser Cys Thr Ala Pro Ala Leu Ser Gly Pro Val Ala Arg Thr Ile
                310             315             320 tat tac atc gca gcc gag ctg gtc cgg ctg gtg ggg tct gtg gac tcc     1185
Tyr Tyr Ile Ala Ala Glu Leu Val Arg Leu Val Gly Ser Val Asp Ser
                325             330             335 atg aag ccc gtg ctc cag tcc ctc tac cac cga gtg ctg ctc tac ccc     1233
Met Lys Pro Val Leu Gln Ser Leu Tyr His Arg Val Leu Leu Tyr Pro
        340             345             350 cca ccc cag cac cgg gtg gaa gcc atc aaa ata atg aaa gag ata ctt     1281
Pro Pro Gln His Arg Val Glu Ala Ile Lys Ile Met Lys Glu Ile Leu
355             360             365             370 ggg agc cca cag cgt ctc tgt gac ttg gca gga ccc agc tcc act gaa     1329
Gly Ser Pro Gln Arg Leu Cys Asp Leu Ala Gly Pro Ser Ser Thr Glu
                375             380             385 tca gag tcc aga aaa aga tca att tca aaa aga aag tct cat ctg gat     1377
Ser Glu Ser Arg Lys Arg Ser Ile Ser Lys Arg Lys Ser His Leu Asp
                390             395             400 ctc ctc aaa ctc atc atg gat ggc atg acc gaa gca tgc atc aag ggt     1425
Leu Leu Lys Leu Ile Met Asp Gly Met Thr Glu Ala Cys Ile Lys Gly
        405             410             415 ggc atc gaa gct tgc tat gca gcc gtg tcc tgt gtc tgc acc ttg ctg     1473
Gly Ile Glu Ala Cys Tyr Ala Ala Val Ser Cys Val Cys Thr Leu Leu
        420             425             430 ggt gcc ctg gat gag ctc agc cag ggg aag ggc ttg agc gaa ggt cag     1521
Gly Ala Leu Asp Glu Leu Ser Gln Gly Lys Gly Leu Ser Glu Gly Gln
435             440             445             450 gtg caa ctg ctg ctt ctg cgc ctt gag gag ctg aag gat ggg gct gag     1569
Val Gln Leu Leu Leu Leu Arg Leu Glu Glu Leu Lys Asp Gly Ala Glu
                455             460             465 tgg agc cga gat tcc atg gag atc aat gag gct gac ttc cgc tgg cag     1617
Trp Ser Arg Asp Ser Met Glu Ile Asn Glu Ala Asp Phe Arg Trp Gln
                470             475             480 cgg cga gtg ctg tcc tca gaa cac acg ccg tgg gag tca ggg aac gag     1665
Arg Arg Val Leu Ser Ser Glu His Thr Pro Trp Glu Ser Gly Asn Glu
                485             490             495 agg agc ctt gac atc agc atc agt gtc acc aca gac aca ggc cag acc     1713
Arg Ser Leu Asp Ile Ser Ile Ser Val Thr Thr Asp Thr Gly Gln Thr
        500             505             510 act ctc gag gga gag ttg ggt cag act aca ccc gag gac cat tcg gga     1761
Thr Leu Glu Gly Glu Leu Gly Gln Thr Thr Pro Glu Asp His Ser Gly
```

-continued

```
            515                     520                     525                     530 aac cac aag aac agt ctc aag tcg cca gcc atc cca gag ggt aag gag       1809
Asn His Lys Asn Ser Leu Lys Ser Pro Ala Ile Pro Glu Gly Lys Glu
                    535                     540                     545 acg ctg agc aaa gta ttg gaa aca gag gcg gta gac cag cca gat gtc       1857
Thr Leu Ser Lys Val Leu Glu Thr Glu Ala Val Asp Gln Pro Asp Val
                550                     555                     560 gtg cag aga agc cac acg gtc cct tac cct gac ata act aac ttc ctg       1905
Val Gln Arg Ser His Thr Val Pro Tyr Pro Asp Ile Thr Asn Phe Leu
            565                     570                     575 tca gta gac tgc agg aca agg tcc tat gga tct agg tat agt gag agc       1953
Ser Val Asp Cys Arg Thr Arg Ser Tyr Gly Ser Arg Tyr Ser Glu Ser
        580                     585                     590 aat ttt agc gtt gat gac caa gac ctt tct agg aca gag ttt gat tcc       2001
Asn Phe Ser Val Asp Asp Gln Asp Leu Ser Arg Thr Glu Phe Asp Ser
595                     600                     605                     610 tgt gat cag tac tct atg gca gca gaa aag gac tcg ggc agg tcc gac       2049
Cys Asp Gln Tyr Ser Met Ala Ala Glu Lys Asp Ser Gly Arg Ser Asp
                    615                     620                     625 gtg tca gac att ggg tcg gac aac tgt tca cta gcc gat gaa gag cag       2097
Val Ser Asp Ile Gly Ser Asp Asn Cys Ser Leu Ala Asp Glu Glu Gln
                630                     635                     640 aca ccc cgg gac tgc cta ggc cac cgg tcc ctg cga act gcc gcc ctg       2145
Thr Pro Arg Asp Cys Leu Gly His Arg Ser Leu Arg Thr Ala Ala Leu
            645                     650                     655 tct cta aaa ctg ctg aag aac cag gag gcg gat cag cac agc gcc agg       2193
Ser Leu Lys Leu Leu Lys Asn Gln Glu Ala Asp Gln His Ser Ala Arg
        660                     665                     670 ctg ttc ata cag tcc ctg gaa ggc ctc ctc cct cgg ctc ctg tct ctc       2241
Leu Phe Ile Gln Ser Leu Glu Gly Leu Leu Pro Arg Leu Leu Ser Leu
675                     680                     685                     690 tcc aat gta gag gag gtg gac acc gct ctg cag aac ttt gcc tct act       2289
Ser Asn Val Glu Glu Val Asp Thr Ala Leu Gln Asn Phe Ala Ser Thr
                    695                     700                     705 ttc tgc tca ggc atg atg cac tct cct ggc ttt gac ggg aat agc agc       2337
Phe Cys Ser Gly Met Met His Ser Pro Gly Phe Asp Gly Asn Ser Ser
                710                     715                     720 ctc agc ttc cag atg ctg atg aac gca gac agc ctc tac aca gct gca       2385
Leu Ser Phe Gln Met Leu Met Asn Ala Asp Ser Leu Tyr Thr Ala Ala
            725                     730                     735 cac tgc gcc ctg ctc ctc aac ctg aag ctc tcc cac ggt gac tac tac       2433
His Cys Ala Leu Leu Leu Asn Leu Lys Leu Ser His Gly Asp Tyr Tyr
        740                     745                     750 agg aag cgg ccg acc ctg gcg cca ggc gtg atg aag gac ttc atg aag       2481
Arg Lys Arg Pro Thr Leu Ala Pro Gly Val Met Lys Asp Phe Met Lys
755                     760                     765                     770 cag gtg cag acc agc ggc gtg ctg atg gtc ttc tct cag gcc tgg att       2529
Gln Val Gln Thr Ser Gly Val Leu Met Val Phe Ser Gln Ala Trp Ile
                    775                     780                     785 gag gag ctc tac cat cag gtg ctc gac agg aac atg ctt gga gag gct       2577
Glu Glu Leu Tyr His Gln Val Leu Asp Arg Asn Met Leu Gly Glu Ala
                790                     795                     800 ggc tat tgg ggc agc cca gaa gat aac agc ctt ccc ctc atc aca atg       2625
Gly Tyr Trp Gly Ser Pro Glu Asp Asn Ser Leu Pro Leu Ile Thr Met
            805                     810                     815 ctg acc gat att gac ggc tta gag agc agt gcc att ggt ggc cag ctg       2673
Leu Thr Asp Ile Asp Gly Leu Glu Ser Ser Ala Ile Gly Gly Gln Leu
        820                     825                     830 atg gcc tcg gct gct aca gag tct cct ttc gcc cag agc agg aga att       2721
```

```
Met Ala Ser Ala Ala Thr Glu Ser Pro Phe Ala Gln Ser Arg Arg Ile
835                 840                 845                 850 gat gac tcc aca gtg gca ggc gtg gca ttt gct cgc tat att ctg gtg      2769
Asp Asp Ser Thr Val Ala Gly Val Ala Phe Ala Arg Tyr Ile Leu Val
                855                 860                 865 ggc tgc tgg aag aac ttg atc gat act tta tca acc cca ctg act ggt      2817
Gly Cys Trp Lys Asn Leu Ile Asp Thr Leu Ser Thr Pro Leu Thr Gly
            870                 875                 880 cga atg gcg ggg agc tcc aaa ggg ctg gcc ttc att ctg gga gct gaa      2865
Arg Met Ala Gly Ser Ser Lys Gly Leu Ala Phe Ile Leu Gly Ala Glu
        885                 890                 895 ggc atc aaa gag cag aac cag aag gag cgg gac gcc atc tgc atg agc      2913
Gly Ile Lys Glu Gln Asn Gln Lys Glu Arg Asp Ala Ile Cys Met Ser
    900                 905                 910 ctc gac ggg ctg cgg aaa gcc gca cgg ctg agc tgc gct cta ggc gtt      2961
Leu Asp Gly Leu Arg Lys Ala Ala Arg Leu Ser Cys Ala Leu Gly Val
915                 920                 925                 930 gct gct aac tgc gcc tca gcc ctt gcc cag atg gca gct gcc tcc tgt      3009
Ala Ala Asn Cys Ala Ser Ala Leu Ala Gln Met Ala Ala Ala Ser Cys
                935                 940                 945 gtc caa gaa gaa aaa gaa gag agg gag gcc caa gaa ccc agt gat gcc      3057
Val Gln Glu Glu Lys Glu Glu Arg Glu Ala Gln Glu Pro Ser Asp Ala
            950                 955                 960 atc aca caa gtg aaa cta aaa gtg gag cag aaa ctg gag cag att ggg      3105
Ile Thr Gln Val Lys Leu Lys Val Glu Gln Lys Leu Glu Gln Ile Gly
        965                 970                 975 aag gtg cag ggg gtg tgg ctg cac act gcc cac gtc ttg tgc atg gag      3153
Lys Val Gln Gly Val Trp Leu His Thr Ala His Val Leu Cys Met Glu
    980                 985                 990 gcc atc ctc agc gta ggc  ctg gag atg gga agc  cac aac ccg gac        3198
Ala Ile Leu Ser Val Gly  Leu Glu Met Gly Ser  His Asn Pro Asp
995                 1000                 1005 tgc  tgg cca cac gtg ttc  agg gtg tgt gaa tac  gtg ggc acc ctg       3243
Cys  Trp Pro His Val Phe  Arg Val Cys Glu Tyr  Val Gly Thr Leu
1010                 1015                 1020 gag  cac aac cac ttc agc  gat ggt gcc tcg cag  ccc cct ctg acc       3288
Glu  His Asn His Phe Ser  Asp Gly Ala Ser Gln  Pro Pro Leu Thr
1025                 1030                 1035 atc  agc cag ccc cag aag  gcc act gga agc gct  ggc ctc ctt ggg       3333
Ile  Ser Gln Pro Gln Lys  Ala Thr Gly Ser Ala  Gly Leu Leu Gly
1040                 1045                 1050 gac  ccc gag tgt gag ggc  tcg ccc ccc gag cac  agc ccg gag cag       3378
Asp  Pro Glu Cys Glu Gly  Ser Pro Pro Glu His  Ser Pro Glu Gln
1055                 1060                 1065 ggg  cgc tcc ctg agc acg  gcc cct gtc gtc cag  ccc ctg tcc atc       3423
Gly  Arg Ser Leu Ser Thr  Ala Pro Val Val Gln  Pro Leu Ser Ile
1070                 1075                 1080 cag  gac ctc gtc cgg gaa  ggc agc cgg ggt cgg  gcc tcc gac ttc       3468
Gln  Asp Leu Val Arg Glu  Gly Ser Arg Gly Arg  Ala Ser Asp Phe
1085                 1090                 1095 cgc  ggc ggg agc ctc atg  agc ggg agc agc gcg  gcc aag gtg gtg       3513
Arg  Gly Gly Ser Leu Met  Ser Gly Ser Ser Ala  Ala Lys Val Val
1100                 1105                 1110 ctc  acc ctc tcc acg caa  gcc gac agg ctc ttt  gaa gat gct acg       3558
Leu  Thr Leu Ser Thr Gln  Ala Asp Arg Leu Phe  Glu Asp Ala Thr
1115                 1120                 1125 gat  aag ttg aac ctc atg  gcc ttg gga ggt ttt  ctt tac cag ctg       3603
Asp  Lys Leu Asn Leu Met  Ala Leu Gly Gly Phe  Leu Tyr Gln Leu
1130                 1135                 1140
```

-continued

```
aag  aaa  gca  tcg  cag  tct  cag  ctt  ttc  cat  tct  gtt  aca  gat  aca     3648
Lys  Lys  Ala  Ser  Gln  Ser  Gln  Leu  Phe  His  Ser  Val  Thr  Asp  Thr
1145            1150                1155 gtt  gat  tac  tct  ctg  gca  atg  cca  gga  gaa  gtt  aaa  tcc  act  caa     3693
Val  Asp  Tyr  Ser  Leu  Ala  Met  Pro  Gly  Glu  Val  Lys  Ser  Thr  Gln
1160            1165                1170 gac  cga  aaa  agc  gcc  ctc  cac  ctg  ttc  cgc  ctg  ggg  aat  gcc  atg     3738
Asp  Arg  Lys  Ser  Ala  Leu  His  Leu  Phe  Arg  Leu  Gly  Asn  Ala  Met
1175            1180                1185 ctg  agg  att  gtg  cgg  agc  aaa  gca  cgg  ccc  ctg  ctc  cac  gtg  atg     3783
Leu  Arg  Ile  Val  Arg  Ser  Lys  Ala  Arg  Pro  Leu  Leu  His  Val  Met
1190            1195                1200 cgc  tgc  tgg  agc  ctt  gtg  gcc  cca  cac  ctg  gtg  gag  gct  gct  tgc     3828
Arg  Cys  Trp  Ser  Leu  Val  Ala  Pro  His  Leu  Val  Glu  Ala  Ala  Cys
1205            1210                1215 cat  aag  gaa  aga  cat  gtg  tct  cag  aag  gct  gtt  tcc  ttc  atc  cat     3873
His  Lys  Glu  Arg  His  Val  Ser  Gln  Lys  Ala  Val  Ser  Phe  Ile  His
1220            1225                1230 gac  ata  ctg  aca  gaa  gtc  ctc  act  gac  tgg  aat  gag  cca  cct  cat     3918
Asp  Ile  Leu  Thr  Glu  Val  Leu  Thr  Asp  Trp  Asn  Glu  Pro  Pro  His
1235            1240                1245 ttt  cac  ttc  aat  gaa  gca  ctc  ttc  cga  cct  ttc  gag  cgc  att  atg     3963
Phe  His  Phe  Asn  Glu  Ala  Leu  Phe  Arg  Pro  Phe  Glu  Arg  Ile  Met
1250            1255                1260 cag  ctg  gaa  ttg  tgt  gat  gag  gac  gtc  caa  gac  cag  gtt  gtc  aca     4008
Gln  Leu  Glu  Leu  Cys  Asp  Glu  Asp  Val  Gln  Asp  Gln  Val  Val  Thr
1265            1270                1275 tcc  att  ggt  gag  ctg  gtt  gaa  gtg  tgt  tcc  acg  cag  atc  cag  tcg     4053
Ser  Ile  Gly  Glu  Leu  Val  Glu  Val  Cys  Ser  Thr  Gln  Ile  Gln  Ser
1280            1285                1290 gga  tgg  aga  ccc  ttg  ttc  agt  gcc  ctg  gaa  aca  gtg  cat  ggc  ggg     4098
Gly  Trp  Arg  Pro  Leu  Phe  Ser  Ala  Leu  Glu  Thr  Val  His  Gly  Gly
1295            1300                1305 aac  aag  tca  gag  atg  aag  gag  tac  ctg  gtt  ggt  gac  tac  tcc  atg     4143
Asn  Lys  Ser  Glu  Met  Lys  Glu  Tyr  Leu  Val  Gly  Asp  Tyr  Ser  Met
1310            1315                1320 gga  aaa  ggc  caa  gct  cca  gtg  ttt  gat  gta  ttt  gaa  gct  ttt  ctc     4188
Gly  Lys  Gly  Gln  Ala  Pro  Val  Phe  Asp  Val  Phe  Glu  Ala  Phe  Leu
1325            1330                1335 aat  act  gac  aac  atc  cag  gtc  ttt  gct  aat  gca  gcc  act  agc  tac     4233
Asn  Thr  Asp  Asn  Ile  Gln  Val  Phe  Ala  Asn  Ala  Ala  Thr  Ser  Tyr
1340            1345                1350 atc  atg  tgc  ctt  atg  aag  ttt  gtc  aaa  gga  ctg  ggg  gag  gtg  gac     4278
Ile  Met  Cys  Leu  Met  Lys  Phe  Val  Lys  Gly  Leu  Gly  Glu  Val  Asp
1355            1360                1365 tgt  aaa  gag  att  gga  gac  tgt  gcc  cca  gca  ccc  gga  gcc  ccg  tcc     4323
Cys  Lys  Glu  Ile  Gly  Asp  Cys  Ala  Pro  Ala  Pro  Gly  Ala  Pro  Ser
1370            1375                1380 aca  gac  ctg  tgc  ctc  ccg  gcc  ctg  gat  tac  ctc  agg  cgc  tgc  tct     4368
Thr  Asp  Leu  Cys  Leu  Pro  Ala  Leu  Asp  Tyr  Leu  Arg  Arg  Cys  Ser
1385            1390                1395 cag  tta  ttg  gcc  aaa  atc  tac  aaa  atg  ccc  ttg  aag  cca  ata  ttc     4413
Gln  Leu  Leu  Ala  Lys  Ile  Tyr  Lys  Met  Pro  Leu  Lys  Pro  Ile  Phe
1400            1405                1410 ctt  agt  ggg  aga  ctt  gcc  ggc  ttg  cct  cga  aga  ctt  cag  gaa  cag     4458
Leu  Ser  Gly  Arg  Leu  Ala  Gly  Leu  Pro  Arg  Arg  Leu  Gln  Glu  Gln
1415            1420                1425 tca  gcc  agc  agt  gag  gat  gga  att  gaa  tca  gtc  ctg  tct  gat  ttt     4503
Ser  Ala  Ser  Ser  Glu  Asp  Gly  Ile  Glu  Ser  Val  Leu  Ser  Asp  Phe
1430            1435                1440
```

-continued

```
gat  gat  gac  acc  ggt  ctg  ata  gaa  gtc  tgg  ata  atc  ctg  ctg  gag        4548
Asp  Asp  Asp  Thr  Gly  Leu  Ile  Glu  Val  Trp  Ile  Ile  Leu  Leu  Glu
1445                 1450                1455 cag  ctg  aca  gcg  gct  gtg  tcc  aat  tgt  cca  cgg  cag  cac  caa  cca        4593
Gln  Leu  Thr  Ala  Ala  Val  Ser  Asn  Cys  Pro  Arg  Gln  His  Gln  Pro
1460                 1465                1470 cca  act  ctg  gat  tta  ctc  ttt  gag  ctg  ttg  aga  gat  gtg  acg  aaa        4638
Pro  Thr  Leu  Asp  Leu  Leu  Phe  Glu  Leu  Leu  Arg  Asp  Val  Thr  Lys
1475                 1480                1485 aca  cca  gga  cca  ggg  ttt  ggt  atc  tat  gca  gtg  gtt  cac  ctc  ctc        4683
Thr  Pro  Gly  Pro  Gly  Phe  Gly  Ile  Tyr  Ala  Val  Val  His  Leu  Leu
1490                 1495                1500 ctt  cct  gtg  atg  tcc  gtt  tgg  ctc  cgc  cgg  agc  cat  aaa  gac  cat        4728
Leu  Pro  Val  Met  Ser  Val  Trp  Leu  Arg  Arg  Ser  His  Lys  Asp  His
1505                 1510                1515 tcc  tac  tgg  gat  atg  gcc  tct  gcc  aat  ttc  aag  cac  gct  att  ggt        4773
Ser  Tyr  Trp  Asp  Met  Ala  Ser  Ala  Asn  Phe  Lys  His  Ala  Ile  Gly
1520                 1525                1530 ctg  tcc  tgt  gag  ctg  gtg  gtg  gag  cac  att  caa  agc  ttt  cta  cat        4818
Leu  Ser  Cys  Glu  Leu  Val  Val  Glu  His  Ile  Gln  Ser  Phe  Leu  His
1535                 1540                1545 tca  gat  atc  agg  tac  gag  agc  atg  atc  aat  acc  atg  ctg  aag  gac        4863
Ser  Asp  Ile  Arg  Tyr  Glu  Ser  Met  Ile  Asn  Thr  Met  Leu  Lys  Asp
1550                 1555                1560 ctc  ttt  gag  ttg  ctg  gtc  gcc  tgt  gtg  gcc  aag  ccc  act  gaa  acc        4908
Leu  Phe  Glu  Leu  Leu  Val  Ala  Cys  Val  Ala  Lys  Pro  Thr  Glu  Thr
1565                 1570                1575 atc  tcc  aga  gtg  ggc  tgc  tcc  tgt  att  aga  tac  gtc  ctt  gtg  aca        4953
Ile  Ser  Arg  Val  Gly  Cys  Ser  Cys  Ile  Arg  Tyr  Val  Leu  Val  Thr
1580                 1585                1590 gcg  ggc  cct  gtg  ttc  act  gag  gag  atg  tgg  agg  ctt  gcc  tgc  tgt        4998
Ala  Gly  Pro  Val  Phe  Thr  Glu  Glu  Met  Trp  Arg  Leu  Ala  Cys  Cys
1595                 1600                1605 gcc  ctg  caa  gat  gcg  ttc  tct  gcc  aca  ctc  aag  cca  gtg  aag  gac        5043
Ala  Leu  Gln  Asp  Ala  Phe  Ser  Ala  Thr  Leu  Lys  Pro  Val  Lys  Asp
1610                 1615                1620 ctg  ctg  ggc  tgc  ttc  cac  agc  ggc  acg  gag  agc  ttc  agc  ggg  gaa        5088
Leu  Leu  Gly  Cys  Phe  His  Ser  Gly  Thr  Glu  Ser  Phe  Ser  Gly  Glu
1625                 1630                1635 ggc  tgc  cag  gtg  cga  gtg  gcg  gcc  ccg  tcc  tcc  tcc  cca  agt  gcc        5133
Gly  Cys  Gln  Val  Arg  Val  Ala  Ala  Pro  Ser  Ser  Ser  Pro  Ser  Ala
1640                 1645                1650 gag  gcc  gag  tac  tgg  cgc  atc  cga  gcc  atg  gcc  cag  cag  gtg  ttt        5178
Glu  Ala  Glu  Tyr  Trp  Arg  Ile  Arg  Ala  Met  Ala  Gln  Gln  Val  Phe
1655                 1660                1665 atg  ctg  gac  acc  cag  tgc  tca  cca  aag  aca  cca  aac  aac  ttt  gac        5223
Met  Leu  Asp  Thr  Gln  Cys  Ser  Pro  Lys  Thr  Pro  Asn  Asn  Phe  Asp
1670                 1675                1680 cac  gct  cag  tcc  tgc  cag  ctc  att  att  gag  ctg  cct  cct  gat  gaa        5268
His  Ala  Gln  Ser  Cys  Gln  Leu  Ile  Ile  Glu  Leu  Pro  Pro  Asp  Glu
1685                 1690                1695 aaa  cca  aat  gga  cac  acc  aag  aaa  agc  gtg  tct  ttc  agg  gaa  att        5313
Lys  Pro  Asn  Gly  His  Thr  Lys  Lys  Ser  Val  Ser  Phe  Arg  Glu  Ile
1700                 1705                1710 gtg  gtg  agc  ctg  ctg  tct  cat  cag  gtg  tta  ctc  cag  aac  tta  tat        5358
Val  Val  Ser  Leu  Leu  Ser  His  Gln  Val  Leu  Leu  Gln  Asn  Leu  Tyr
1715                 1720                1725 gac  atc  ttg  tta  gaa  gag  ttt  gtc  aaa  ggc  ccc  tct  cct  gga  gag        5403
Asp  Ile  Leu  Leu  Glu  Glu  Phe  Val  Lys  Gly  Pro  Ser  Pro  Gly  Glu
```

-continued

```
                    1730                    1735                    1740 gaa   aag acg ata caa gtg   cca gaa gcc aag ctg   gct ggc ttc ctc          5448
Glu   Lys Thr Ile Gln Val   Pro Glu Ala Lys Leu   Ala Gly Phe Leu
1745                    1750                    1755 aga   tac atc tct atg cag   aac ttg gca gtc ata   ttc gac ctg ctg          5493
Arg   Tyr Ile Ser Met Gln   Asn Leu Ala Val Ile   Phe Asp Leu Leu
1760                    1765                    1770 ctg   gac tct tat agg act   gcc agg gag ttt gac   acc agc ccc ggg          5538
Leu   Asp Ser Tyr Arg Thr   Ala Arg Glu Phe Asp   Thr Ser Pro Gly
1775                    1780                    1785 ctg   aag tgc ctg ctg aag   aaa gtg tct ggc atc   ggg ggc gcc gcc          5583
Leu   Lys Cys Leu Leu Lys   Lys Val Ser Gly Ile   Gly Gly Ala Ala
1790                    1795                    1800 aac   ctc tac cgc cag tct   gcg atg agc ttt aac   att tat ttc cac          5628
Asn   Leu Tyr Arg Gln Ser   Ala Met Ser Phe Asn   Ile Tyr Phe His
1805                    1810                    1815 gcc   ctg gtg tgt gct gtt   ctc acc aat caa gaa   acc atc acg gcc          5673
Ala   Leu Val Cys Ala Val   Leu Thr Asn Gln Glu   Thr Ile Thr Ala
1820                    1825                    1830 gag   caa gtg aag aag gtc   ctt ttt gag gac gac   gag aga agc acg          5718
Glu   Gln Val Lys Lys Val   Leu Phe Glu Asp Asp   Glu Arg Ser Thr
1835                    1840                    1845 gat   tct tcc cag cag tgt   tca tct gag gat gaa   gac atc ttt gag          5763
Asp   Ser Ser Gln Gln Cys   Ser Ser Glu Asp Glu   Asp Ile Phe Glu
1850                    1855                    1860 gaa   acc gcc cag gtc agc   ccc ccg aga ggc aag   gag aag aga cag          5808
Glu   Thr Ala Gln Val Ser   Pro Pro Arg Gly Lys   Glu Lys Arg Gln
1865                    1870                    1875 tgg   cgg gca cgg atg ccc   ttg ctc agc gtc cag   cct gtc agc aac          5853
Trp   Arg Ala Arg Met Pro   Leu Leu Ser Val Gln   Pro Val Ser Asn
1880                    1885                    1890 gca   gat tgg gtg tgg ctg   gtc aag agg ctg cac   aag ctg tgc atg          5898
Ala   Asp Trp Val Trp Leu   Val Lys Arg Leu His   Lys Leu Cys Met
1895                    1900                    1905 gaa   ctg tgc aac aac tac   atc cag atg cac ttg   gac ctg gag aac          5943
Glu   Leu Cys Asn Asn Tyr   Ile Gln Met His Leu   Asp Leu Glu Asn
1910                    1915                    1920 tgt   atg gag gag cct ccc   atc ttc aag ggc gac   ccg ttc ttc atc          5988
Cys   Met Glu Glu Pro Pro   Ile Phe Lys Gly Asp   Pro Phe Phe Ile
1925                    1930                    1935 ctg   ccc tcc ttc cag tcc   gag tca tcc acc cca   tcc acc ggg ggc          6033
Leu   Pro Ser Phe Gln Ser   Glu Ser Ser Thr Pro   Ser Thr Gly Gly
1940                    1945                    1950 ttc   tct ggg aaa gaa acc   cct tcc gag gat gac   aga agc cag tcc          6078
Phe   Ser Gly Lys Glu Thr   Pro Ser Glu Asp Asp   Arg Ser Gln Ser
1955                    1960                    1965 cgg   gag cac atg ggc gag   tcc ctg agc ctg aag   gcc ggt ggt ggg          6123
Arg   Glu His Met Gly Glu   Ser Leu Ser Leu Lys   Ala Gly Gly Gly
1970                    1975                    1980 gac   ctg ctg ctg ccc ccc   agc ccc aaa gtg gag   aag aag gat ccc          6168
Asp   Leu Leu Leu Pro Pro   Ser Pro Lys Val Glu   Lys Lys Asp Pro
1985                    1990                    1995 agc   cgg aag aag gag tgg   tgg gag aat gcg ggg   aac aaa atc tac          6213
Ser   Arg Lys Lys Glu Trp   Trp Glu Asn Ala Gly   Asn Lys Ile Tyr
2000                    2005                    2010 acc   atg gca gcc gac aag   acc att tca aag ttg   atg acc gaa tac          6258
Thr   Met Ala Ala Asp Lys   Thr Ile Ser Lys Leu   Met Thr Glu Tyr
2015                    2020                    2025 aaa   aag agg aaa cag cag   cac aac ctg tcc gcg   ttc ccc aaa gag          6303
```

-continued

```
Lys  Lys Arg Lys Gln Gln  His Asn Leu Ser Ala  Phe Pro Lys Glu
2030             2035              2040 gtc  aaa gtg gag aag aaa  gga gag cca ctg ggt  ccc agg ggc cag       6348
Val  Lys Val Glu Lys Lys  Gly Glu Pro Leu Gly  Pro Arg Gly Gln
2045             2050              2055 gac  tcc ccg ctg ctt cag  cgt ccc cag cac ttg  atg gac caa ggg       6393
Asp  Ser Pro Leu Leu Gln  Arg Pro Gln His Leu  Met Asp Gln Gly
2060             2065              2070 caa  atg cgg cat tcc ttc  agc gca ggc ccc gag  ctg ctg cga cag       6438
Gln  Met Arg His Ser Phe  Ser Ala Gly Pro Glu  Leu Leu Arg Gln
2075             2080              2085 gac  aag agg ccc cgc tca  ggc tcc acc ggg agc  tcc ctc agt gtc       6483
Asp  Lys Arg Pro Arg Ser  Gly Ser Thr Gly Ser  Ser Leu Ser Val
2090             2095              2100 tcg  gtg aga gac gca gaa  gca cag atc cag gca  tgg acc aac atg       6528
Ser  Val Arg Asp Ala Glu  Ala Gln Ile Gln Ala  Trp Thr Asn Met
2105             2110              2115 gtg  cta aca gtt ctc aat  cag att cag att ctc  cca gac cag acc       6573
Val  Leu Thr Val Leu Asn  Gln Ile Gln Ile Leu  Pro Asp Gln Thr
2120             2125              2130 ttc  acg gcc ctc cag ccc  gca gtg ttc ccg tgc  atc agt cag ctg       6618
Phe  Thr Ala Leu Gln Pro  Ala Val Phe Pro Cys  Ile Ser Gln Leu
2135             2140              2145 acc  tgt cac gtg acc gac  atc aga gtt cgc cag  gct gtg agg gag       6663
Thr  Cys His Val Thr Asp  Ile Arg Val Arg Gln  Ala Val Arg Glu
2150             2155              2160 tgg  ctg ggc agg gtg ggc  cgt gtc tat gac atc  att gtg tag           6705
Trp  Leu Gly Arg Val Gly  Arg Val Tyr Asp Ile  Ile Val
2165             2170              2175 ccgactcctg ttctactctc ccaccaaata acagtagtga gggttagagt cctgccaata    6765
cagctgttgc attttcccca ccactagccc cacttaaact actactactg tctcagagaa    6825
cagtgtttcc taatgtaaaa agcctttcca accactgatc agcattgggg ccatactaag    6885
gtttgtatct agatgacaca aacgatattc tgattttgca cattattata gaagaatcta    6945
taatccttga tatgtttcta actcttgaag tatatttccc agtgcttttg cttacagtgt    7005
tgtccccaaa tgggtcattt tcaaggatta ctcatttgaa aacactatat tgatccattt    7065
gatccatcat ttaaaaaata aatacaattc ctaaggcaat atctgctggt aagtcaagct    7125
gataaacact cagacatcta gtaccaggga ttattaattg gaggaagatt tatggttatg    7185
ggtctggctg ggaagaagac aactataaat acatattctt gggtgtcata atcaagaaag    7245
aggtgacttc tgttgtaaaa taatccagaa cacttcaaaa ttattcctaa atcattaaga    7305
ttttcaggta ttcaccaatt tccccatgta aggtactgtg ttgtaccttt atttctgtat    7365
ttctaaaaga agaaagttct ttcctagcag ggtttgaagt ctgtggctta tcagcctgtg    7425
acacagagta cccagtgaaa gtggctggta cgtagattgt caagagacat aagaccgacc    7485
agccaccctg gctgttcttg tggtgtttgt ttccatcccc aaggcaaaca aggaaaggaa    7545
aggaaagaag aaaaggtgcc ttagtccttt gttgcacttc catttccatg ccccacaatt    7605
gtctgaacat aaggtatagc atttggtttt taagaaaaca aaacattaag acgcaactca    7665
ttttatatca acacgcttgg aggaaaggga ctcaggaag ggagcaggga gtgtggggtg      7725
gggatggatt atgatgaaat cattttcaat cttaaaatat aatacaacaa tcttgcaaaa    7785
ttatggtgtc agttacacaa gctctagtct caaaatgaaa gtaatggaga aagacactga    7845
aatttagaaa attttgtcga tttaaaatat ttctcctatc taccaagtaa agttacccta    7905
```

-continued

```
tgtttgatgt ctttgcattc agaccaatat ttcaggtgga tatttctaag tattactaga     7965
aaatacgttt gaaagcttta tcttattatt tacagtattt ttatatttct tacattatcc     8025
taatgattga aaactcctca atcaagctta cttacacaca ttctacagag ttatttaagg     8085
catacattat aatctcccag ccccattcat aatgaataag tcacccttta aatataagac     8145
acaaattcta cagtattgaa ataaggattt aaaggggtat ttgtaaactt tgccctcctt     8205
gagaaatatg gaactacctt agaggttaag aggaaggcag tgttctgact tctttaggtg     8265
atctgaaaaa aacaccctta tcatccagtg taccatctag agatcaccac agaatccatt     8325
tttttcccag ttccacaaaa cactctgttt gccttcagtt tttactcact agacaataat     8385
tcaagtttag aaacaggtaa tcagctattt gatcttaaaa ggcaatgaat tgttgggata     8445
tcagtgaact atgttgtata cttttgaatt tttacatttt ataaatggaa ttgaaagttg     8505
gataactgct ttttttaaat tttccaacag aagtaacacc acagttgctt tgtttctttt     8565
tatagcttac ctgaggttca gttcttcttt gtgaacctgt gagtactcca cagtttactg     8625
ggggaaaagg cttcagtaaa gcagaggcta gaattacagt atttatacat agcaactttt     8685
cataaagtag aaaaattcaa aggaagctgt ctcaatttga gaataccagc tgggcacggt     8745
ggctcacgcc tgtaatccca gcacttactt tgggaggcca aggtgggcag ataacctgcg     8805
gtcaggagtt tgagaccagg ctggacaaca tggtgaaacc tcgtctctac taaaaataca     8865
aaaattagcc aggtgtggta ggatgcacct gtaatcccag ctacttagga ggccgagaca     8925
ggagaatcgc tcgaacccag gaggcggacg ttgcagtgag ccaagattgc accattgcac     8985
tccagactgg gtgacaagag tgaaactcca tctaaaaaaa aaaaaaaaaa aaagtgaata     9045
ctgtatccca aagtatgtta gttgtttgtt tggaaatcag cattctcccc gatgctctat     9105
tatgggatcc aaaattcttg aacataagtt taccctgtac tgtgtccaaa cactgttcta     9165
gttctagcct gattatgggt cccaagaata aaaggatgag taggtgtaca gagctcttga     9225
cctacaattt tttaagagtg ttttggtacc ttcccattgt cttctctata actcagtcct     9285
aacatactct gcactcgagt taccagccat ccacactgac atcagatttc aaccagaacc     9345
atcactgagt gacagcagta cttctcagag gtatttgcag cttgatgcaa agtagtctct     9405
aatgagtagg cattcaggtg gttcttccca gcaggtggag aagaaaggga ggagatgaag     9465
aacactgaga ggggagtggc accttcccag gctgcccagc tcagtctctt gccctgttcc     9525
tgtgactcag ctgcccactc ccccaacttt gtttccctcc ctcccagtct ctgaaagtgt     9585
caggtgtttc tctcctcaca gtctcttttg cagcaacagt aagacaaaat tcaaggcagc     9645
cttttaaagt tacgaacagt tattagcatg tatttacaga cctaagcaga atgagagttt     9705
atacattgtt tttagttgcc tgtatttata gccaaaagta tattacctta aagttgagat     9765
ctttctcttc ttttcctaaa ttttggtaaa gtgtgcttca tgaaacaaac atctggaaaa     9825
ctccaagtat aagagaccct ggactgatga tggcccagcc aagtatatgg agggacagag     9885
ttctctctgt cattaatgag gacatcggtt ttcacaattg aacctcatgc actgtccaca     9945
gcatctcacc tagctcctgt atctcctgat ctgcttttaa aaatagttag ttaggctgcc     10005
tttttacacc accttctctc tctccccttg tggtaatttt ccagccttcc ccatagatat     10065
aaaactagaa cacctttatg atttggggtc tatgtaatga ctgaccgata agaacccagg     10125
cagatgctaa catacttaac agctcgcatt aaaatacttt aaatcaggcg tgatggctca     10185
ttcctgtaat ctcaagcact ttgggaggct aaggtgggtg gatctcttga ggtcaggagt     10245
tcgagaccaa cctggccaac gtggtgaaac cccgtctcta ctaaaaatac aaaattagcc     10305
```

-continued

```
gggcatggtg gcagctgcct gtaatcccag ctactcggga agctgaggca ggagaattgc   10365
ttgaacctgg gaggtgggga ttgcagtcag ccaagattgt tctgcagcat gggtgacaaa   10425
gtgagacttc gtctcaagta aataaaacta aaatttttaa atcaaacatg acaaaaatgt   10485
taatataatt cagaagtacc ttgaaattga aacatatttg tgcaatgatc attaggcttt   10545
ttgtccttgt tgttttaaaa tgaggcttat acagagtgag ttgagagtca agtagccttc   10605
gctgtgagac ggtaatgcag ttatataata gatacccttg actttgccag attcatcaca   10665
atactgctta tacaggaaag ttttctcaga aaggaaaatc cattagtatc agtcccatca   10725
agccaaacag aatgaagacc tttgatagta atagcaagag gttacaaata gcagggagga   10785
ggcgagtagt gaatgtcact gtgattgcaa acccttacct gtattatcac acgtagtcct   10845
cacaacaacc ttgtgagaca agtgttgtgt tcctcatttt ttcagagggg aacacagacc   10905
cagagaggtt aagaaatttg cccaagataa caagtaaaag gcaaagttgg ttgcaaaaga   10965
ggtgtttctg aattcaaggg ccatactctc tctctgacaa catgctctaa gtccatagag   11025
taagcactct agtatgaaaa aaagtttcaa ggaacgaggc catgaaaatg agactatttg   11085
acatctcaga tctgtctggg atgttatgga ggttttttaaa aataaagttg aaaaaagaaa   11145
atgaatcatg tttatacata aaaaaatcac atgtaacaca tttcaagtgt ttgaaaataa   11205
aaccaaaatc taaactttag tcttcaagca gacattcagt gttactttag aaaactcact   11265
gaattaggtg gaaatgatgg aataatacta ttcatggcca gctattaaca cagaagaaca   11325
tggcagtgtg tgtctggaac ggcatgcaca atttgtaaac ctttttcaaa tatcatttaa   11385
tcaactcaga ataaagtgcc ctgtagccaa cagtgcctct ttacttgctt ctctgggaaa   11445
tacatggtac taaattagta gcacaaagtt tgggaatatg caaaataatg gataaccatt   11505
tttcaaaatg tacattctct gaagaggaag cagctggttg gacaggattt cttgaagagc   11565
caggtgctaa gggcatcagg tcgacatcca tagtaaccat gtgccataac atctacacat   11625
ttccacttgt tttacagaca aggtaacagg cagaaggaaa atccagagtc ttgcagtaag   11685
cagatgacaa aacttcaata tgcttgggca ccacttaggt gaccccaggg agatttagtg   11745
tggccttagg aaagcaaaag agcacttttt attggaaata tgagcttgtc actgggaaag   11805
atttgtaaaa ttgatcaaga acttgattta taattatgcc tcaaaaaaaa aagttctcat   11865
ttagtagtgg agcaatctag aaaacatacc tttttttgttt gtttggaaga tcctctttcc   11925
ctggctgtat tgtagtgttt gctatttgat gtggaaataa ctaataactt aagattttgg   11985
aacagaacac cctttagatt tccaaaacac aattcttatt tcaggaaga cagaccaaaa   12045 atatctcctg agatcattgg tttctttata aattgtggta ccactccatc attgaagaga   12105
aaccactacc acaccactag caccatacag aaccttttct ctgtatcttt gtacaatact   12165
acaaaggggt accagggagg agagagtggc tgaccacttt agtgacaaaa cagcactcca   12225
ctgctggtga atcccatcta attatggtcc ttccacccctt ttcaaccacc aacaactgtt   12285
cgtactgtta attcctatcc tgaaggttta accagtggtt gtctagtatc ttctgtcttt   12345
agaacagtgg ttctcaaact ttagtacaca tcagcatcac ctggagggcc ttttttttaaa   12405 ataagacaca gattgctggg ctcatggtca gagttcccag ttaagtaaat caggaaattt   12465
gtatttctaa caagtttata ggtgaggcca atactgctgt tttgggaact atgctttgag   12525
aaccactgcc ttgaaaaaat ttccaacttc tacctttaag atcagcctga cttatcaaac   12585
gctagagaaa aactgaatct acccttgggc agatgacttg ggattggatt ctatacagca   12645
```

```
gtcttgctca atcttcccag tttccagttt tattatacca acaattggtt tttacaagct   12705
agaagacaat gaatgtataa gttctatgga acagtgagat aaatctaagc ttcttgtctt   12765
tgtatttaga aacattgatt ctatggatga tcatttgtat catgttgacc ctttgacttg   12825
tactgaaggt gattttaaat ttaagtatgt agtgtttgaa tttcttccat ccatgtcgtt   12885
ttaatgagat gtttccatgt cagctccttt acagccttgg ctcctggctt acagattttt   12945
gaatagttgt ttgcttgcca gttgtttttac atctttcatt ggccaccaaa atattagcca   13005
tttgagatga gatgagacta cttgttgtac cttcatcttt catttaattt tctggcgtaa   13065
attaacattt taatttcata tatatctgta aagagtctac ccaaaggctt cacggaaatt   13125
tgcaaaatga actaattccc tttttaagcag caggtgtgcc tgtttttgac ttttcagtaa   13185
atatgttgtt tgtgcacata tctacatggt ggagaccata ttcattattt catcttccaa   13245
ataatgggaa aaatataaaa gtgaatcagt gtgctttggg aattcagtga aatcatgtta   13305
actcatatag agggggcctt agtttatctc ttctttactg aattaattag ttttggaaat   13365
tcttttacca ttaaaaaaaa ttaaggacca tacagagaat gatttaagaa aaaacaagtc   13425
acttaaaaat catcacctat ttataaactg tattaattac acataatgct tattgattca   13485
atgaggtttc tctaaagact tctgcttaat aaatatgctg acttcattta aattagttta   13545
gactattgta ggaatggaag gaaatgatta tatttactag aattagtgag atcagaaagc   13605
atatcagaat gttgatgata tcaaggagac aatctcacaga gtttttgcct ctgtggatgg   13665
aaataagggt gttttttttt ggtttttttt ttactttagt ttcccataat ttttggaaat   13725
tatgtgtgca tttagttctt ttagtaacac tgattttaaa attaaatttc aaaagtcaat   13785
ctctaagagt aatttatttt tgttttacca accagtgcca aaaggagag gagggaatcc   13845 aaaagccaat cttttgaacc aatgtgtaaa agattatgtt ttttcttaaa gttagggagg   13905
ctcgggccct gacactgcca gccccagtga gcatccctgg ctacctcggg attatgtgca   13965
agctgctttg tcctacattt cttttcatctg gttcttattg ggagtgcttc tctctaataa   14025
aaattgattt cccacaaaat aggcaaagct gaacaaagat gaatgctttt gataagttgg   14085
gtttcacttc agttgaaaca atgtgataga atatccaggt gtggcatgat ggggcaggag   14145
gaggtgccta gagggaaaag ttattttttgt ttcttagtgt tgtgttgtgg ggatgggaca   14205
gataagaata agatgtttat tgccctaatc atgctaagag actattattc aatatgcttt   14265
tcccgctttt ctaagaggaa taaacttaga caaattacat tataaacagt tcccctacta   14325
ctatctccca ctctagataa agccagtggg tggtatgggt cctttattc cttatagtat   14385 tatgccaaag aatcaactta ttttcattga agattataaa taaatgaagc ttgttatagc   14445
cataatgatt tgagtcagta taccatttta cctataaaat gcaaaattca tccttgcaac   14505
cccattcacc aggagccttg aagcattttg tttactccaa aggccttgtc aaggaagcat   14565 aatttttttgt tttgccttct tatttagtca gtttggtcat atttacttaa aaaaacaaac   14625
tgaaaatcac actcctttat atgttgatat aactgatttt atagaatctg tctgttcttt   14685
gtttaacagg tctctgtaag caagcttgca agtgtatttt gtgtacattt tatctgaggt   14745
ggaaatgaaa attctaaaga gaaaatattt taaaagatat tgtatttatg ttgcttgtgt   14805
tgtagaataa agattcaaat gcattaaaaa tctggtacat gaaacaattg tgtttactga   14865
ataaatatat ataaataaaa aaaaaaaaaa                                    14895
```

<210> SEQ ID NO 32
<211> LENGTH: 2177

-continued

<212> TYPE: PRT
<213> ORGANISM: Homo sapiens

<400> SEQUENCE: 32

```
Met Glu Glu Ile Leu Arg Lys Leu Gln Lys Glu Ala Ser Gly Ser Lys
1               5                   10                  15

Tyr Lys Ala Ile Lys Glu Ser Cys Thr Trp Ala Leu Glu Thr Leu Gly
                20                  25                  30

Gly Leu Asp Thr Ile Val Lys Ile Pro Pro His Val Leu Arg Glu Lys
            35                  40                  45

Cys Leu Leu Pro Leu Gln Leu Ala Leu Glu Ser Lys Asn Val Lys Leu
        50                  55                  60

Ala Gln His Ala Leu Ala Gly Met Gln Lys Leu Leu Ser Glu Glu Arg
65                  70                  75                  80

Phe Val Ser Met Glu Thr Asp Ser Asp Glu Lys Gln Leu Leu Asn Gln
                85                  90                  95

Ile Leu Asn Ala Val Lys Val Thr Pro Ser Leu Asn Glu Asp Leu Gln
                100                 105                 110

Val Glu Val Met Lys Val Leu Leu Cys Ile Thr Tyr Thr Pro Thr Phe
            115                 120                 125

Asp Leu Asn Gly Ser Ala Val Leu Lys Ile Ala Glu Val Cys Ile Glu
        130                 135                 140

Thr Tyr Ile Ser Ser Cys His Gln Arg Ser Ile Asn Thr Ala Val Arg
145                 150                 155                 160

Ala Thr Leu Ser Gln Met Leu Ser Asp Leu Thr Leu Gln Leu Arg Gln
                165                 170                 175

Arg Gln Glu Asn Thr Ile Ile Glu Asn Pro Asp Val Pro Gln Asp Phe
                180                 185                 190

Gly Asn Gln Gly Ser Thr Val Glu Ser Leu Cys Asp Asp Val Val Ser
            195                 200                 205

Val Leu Thr Val Leu Cys Glu Lys Leu Gln Ala Ala Ile Asn Asp Ser
        210                 215                 220

Gln Gln Leu Gln Leu Leu Tyr Leu Glu Cys Ile Leu Ser Val Leu Ser
225                 230                 235                 240

Ser Ser Ser Ser Ser Met His Leu His Arg Arg Phe Thr Asp Leu Ile
                245                 250                 255

Trp Lys Asn Leu Cys Pro Ala Leu Ile Val Ile Leu Gly Asn Pro Ile
            260                 265                 270

His Asp Lys Thr Ile Thr Ser Ala His Thr Ser Ser Thr Ser Thr Ser
            275                 280                 285

Leu Glu Ser Asp Ser Ala Ser Pro Gly Val Ser Asp His Gly Arg Gly
        290                 295                 300

Ser Gly Cys Ser Cys Thr Ala Pro Ala Leu Ser Gly Pro Val Ala Arg
305                 310                 315                 320

Thr Ile Tyr Tyr Ile Ala Ala Glu Leu Val Arg Leu Val Gly Ser Val
                325                 330                 335

Asp Ser Met Lys Pro Val Leu Gln Ser Leu Tyr His Arg Val Leu Leu
            340                 345                 350

Tyr Pro Pro Pro Gln His Arg Val Glu Ala Ile Lys Ile Met Lys Glu
            355                 360                 365

Ile Leu Gly Ser Pro Gln Arg Leu Cys Asp Leu Ala Gly Pro Ser Ser
        370                 375                 380

Thr Glu Ser Glu Ser Arg Lys Arg Ser Ile Ser Lys Arg Lys Ser His
385                 390                 395                 400
```

-continued

```
Leu Asp Leu Leu Lys Leu Ile Met Asp Gly Met Thr Glu Ala Cys Ile
            405             410             415

Lys Gly Gly Ile Glu Ala Cys Tyr Ala Ala Val Ser Cys Val Cys Thr
            420             425             430

Leu Leu Gly Ala Leu Asp Glu Leu Ser Gln Gly Lys Gly Leu Ser Glu
            435             440             445

Gly Gln Val Gln Leu Leu Leu Arg Leu Glu Glu Leu Lys Asp Gly
    450             455             460

Ala Glu Trp Ser Arg Asp Ser Met Glu Ile Asn Glu Ala Asp Phe Arg
465             470             475             480

Trp Gln Arg Arg Val Leu Ser Ser Glu His Thr Pro Trp Glu Ser Gly
            485             490             495

Asn Glu Arg Ser Leu Asp Ile Ser Ile Ser Val Thr Thr Asp Thr Gly
            500             505             510

Gln Thr Thr Leu Glu Gly Glu Leu Gly Gln Thr Thr Pro Glu Asp His
            515             520             525

Ser Gly Asn His Lys Asn Ser Leu Lys Ser Pro Ala Ile Pro Glu Gly
            530             535             540

Lys Glu Thr Leu Ser Lys Val Leu Glu Thr Glu Ala Val Asp Gln Pro
545             550             555             560

Asp Val Val Gln Arg Ser His Thr Val Pro Tyr Pro Asp Ile Thr Asn
            565             570             575

Phe Leu Ser Val Asp Cys Arg Thr Arg Ser Tyr Gly Ser Arg Tyr Ser
            580             585             590

Glu Ser Asn Phe Ser Val Asp Asp Gln Asp Leu Ser Arg Thr Glu Phe
            595             600             605

Asp Ser Cys Asp Gln Tyr Ser Met Ala Ala Glu Lys Asp Ser Gly Arg
    610             615             620

Ser Asp Val Ser Asp Ile Gly Ser Asp Asn Cys Ser Leu Ala Asp Glu
625             630             635             640

Glu Gln Thr Pro Arg Asp Cys Leu Gly His Arg Ser Leu Arg Thr Ala
            645             650             655

Ala Leu Ser Leu Lys Leu Leu Lys Asn Gln Glu Ala Asp Gln His Ser
            660             665             670

Ala Arg Leu Phe Ile Gln Ser Leu Glu Gly Leu Leu Pro Arg Leu Leu
            675             680             685

Ser Leu Ser Asn Val Glu Glu Val Asp Thr Ala Leu Gln Asn Phe Ala
    690             695             700

Ser Thr Phe Cys Ser Gly Met Met His Ser Pro Gly Phe Asp Gly Asn
705             710             715             720

Ser Ser Leu Ser Phe Gln Met Leu Met Asn Ala Asp Ser Leu Tyr Thr
            725             730             735

Ala Ala His Cys Ala Leu Leu Leu Asn Leu Lys Leu Ser His Gly Asp
            740             745             750

Tyr Tyr Arg Lys Arg Pro Thr Leu Ala Pro Gly Val Met Lys Asp Phe
            755             760             765

Met Lys Gln Val Gln Thr Ser Gly Val Leu Met Val Phe Ser Gln Ala
    770             775             780

Trp Ile Glu Glu Leu Tyr His Gln Val Leu Asp Arg Asn Met Leu Gly
785             790             795             800

Glu Ala Gly Tyr Trp Gly Ser Pro Glu Asp Asn Ser Leu Pro Leu Ile
            805             810             815
```

```
Thr Met Leu Thr Asp Ile Asp Gly Leu Glu Ser Ser Ala Ile Gly Gly
        820             825             830

Gln Leu Met Ala Ser Ala Ala Thr Glu Ser Pro Phe Ala Gln Ser Arg
        835             840             845

Arg Ile Asp Asp Ser Thr Val Ala Gly Val Ala Phe Ala Arg Tyr Ile
        850             855             860

Leu Val Gly Cys Trp Lys Asn Leu Ile Asp Thr Leu Ser Thr Pro Leu
865             870             875             880

Thr Gly Arg Met Ala Gly Ser Ser Lys Gly Leu Ala Phe Ile Leu Gly
                885             890             895

Ala Glu Gly Ile Lys Glu Gln Asn Gln Lys Glu Arg Asp Ala Ile Cys
                900             905             910

Met Ser Leu Asp Gly Leu Arg Lys Ala Ala Arg Leu Ser Cys Ala Leu
        915             920             925

Gly Val Ala Ala Asn Cys Ala Ser Ala Leu Ala Gln Met Ala Ala Ala
        930             935             940

Ser Cys Val Gln Glu Glu Lys Glu Glu Arg Glu Ala Gln Glu Pro Ser
945             950             955             960

Asp Ala Ile Thr Gln Val Lys Leu Lys Val Glu Gln Lys Leu Glu Gln
                965             970             975

Ile Gly Lys Val Gln Gly Val Trp Leu His Thr Ala His Val Leu Cys
        980             985             990

Met Glu Ala Ile Leu Ser Val Gly  Leu Glu Met Gly Ser  His Asn Pro
        995             1000            1005

Asp Cys  Trp Pro His Val Phe  Arg Val Cys Glu Tyr  Val Gly Thr
1010            1015            1020

Leu Glu  His Asn His Phe Ser  Asp Gly Ala Ser Gln  Pro Pro Leu
1025            1030            1035

Thr Ile  Ser Gln Pro Gln Lys  Ala Thr Gly Ser Ala  Gly Leu Leu
1040            1045            1050

Gly Asp  Pro Glu Cys Glu Gly  Ser Pro Pro Glu His  Ser Pro Glu
1055            1060            1065

Gln Gly  Arg Ser Leu Ser Thr  Ala Pro Val Val Gln  Pro Leu Ser
1070            1075            1080

Ile Gln  Asp Leu Val Arg Glu  Gly Ser Arg Gly Arg  Ala Ser Asp
1085            1090            1095

Phe Arg  Gly Gly Ser Leu Met  Ser Gly Ser Ser Ala  Ala Lys Val
1100            1105            1110

Val Leu  Thr Leu Ser Thr Gln  Ala Asp Arg Leu Phe  Glu Asp Ala
1115            1120            1125

Thr Asp  Lys Leu Asn Leu Met  Ala Leu Gly Gly Phe  Leu Tyr Gln
1130            1135            1140

Leu Lys  Lys Ala Ser Gln Ser  Gln Leu Phe His Ser  Val Thr Asp
1145            1150            1155

Thr Val  Asp Tyr Ser Leu Ala  Met Pro Gly Glu Val  Lys Ser Thr
1160            1165            1170

Gln Asp  Arg Lys Ser Ala Leu  His Leu Phe Arg Leu  Gly Asn Ala
1175            1180            1185

Met Leu  Arg Ile Val Arg Ser  Lys Ala Arg Pro Leu  Leu His Val
1190            1195            1200

Met Arg  Cys Trp Ser Leu Val  Ala Pro His Leu Val  Glu Ala Ala
1205            1210            1215

Cys His  Lys Glu Arg His Val  Ser Gln Lys Ala Val  Ser Phe Ile
```

-continued

```
             1220              1225              1230

His Asp  Ile Leu Thr Glu Val  Leu Thr Asp Trp Asn  Glu Pro Pro
    1235              1240              1245

His Phe  His Phe Asn Glu Ala  Leu Phe Arg Pro Phe  Glu Arg Ile
    1250              1255              1260

Met Gln  Leu Glu Leu Cys Asp  Glu Asp Val Gln Asp  Gln Val Val
    1265              1270              1275

Thr Ser  Ile Gly Glu Leu Val  Glu Val Cys Ser Thr  Gln Ile Gln
    1280              1285              1290

Ser Gly  Trp Arg Pro Leu Phe  Ser Ala Leu Glu Thr  Val His Gly
    1295              1300              1305

Gly Asn  Lys Ser Glu Met Lys  Glu Tyr Leu Val Gly  Asp Tyr Ser
    1310              1315              1320

Met Gly  Lys Gly Gln Ala Pro  Val Phe Asp Val Phe  Glu Ala Phe
    1325              1330              1335

Leu Asn  Thr Asp Asn Ile Gln  Val Phe Ala Asn Ala  Ala Thr Ser
    1340              1345              1350

Tyr Ile  Met Cys Leu Met Lys  Phe Val Lys Gly Leu  Gly Glu Val
    1355              1360              1365

Asp Cys  Lys Glu Ile Gly Asp  Cys Ala Pro Ala Pro  Gly Ala Pro
    1370              1375              1380

Ser Thr  Asp Leu Cys Leu Pro  Ala Leu Asp Tyr Leu  Arg Arg Cys
    1385              1390              1395

Ser Gln  Leu Leu Ala Lys Ile  Tyr Lys Met Pro Leu  Lys Pro Ile
    1400              1405              1410

Phe Leu  Ser Gly Arg Leu Ala  Gly Leu Pro Arg Arg  Leu Gln Glu
    1415              1420              1425

Gln Ser  Ala Ser Ser Glu Asp  Gly Ile Glu Ser Val  Leu Ser Asp
    1430              1435              1440

Phe Asp  Asp Asp Thr Gly Leu  Ile Glu Val Trp Ile  Ile Leu Leu
    1445              1450              1455

Glu Gln  Leu Thr Ala Ala Val  Ser Asn Cys Pro Arg  Gln His Gln
    1460              1465              1470

Pro Pro  Thr Leu Asp Leu Leu  Phe Glu Leu Leu Arg  Asp Val Thr
    1475              1480              1485

Lys Thr  Pro Gly Pro Gly Phe  Gly Ile Tyr Ala Val  Val His Leu
    1490              1495              1500

Leu Leu  Pro Val Met Ser Val  Trp Leu Arg Arg Ser  His Lys Asp
    1505              1510              1515

His Ser  Tyr Trp Asp Met Ala  Ser Ala Asn Phe Lys  His Ala Ile
    1520              1525              1530

Gly Leu  Ser Cys Glu Leu Val  Val Glu His Ile Gln  Ser Phe Leu
    1535              1540              1545

His Ser  Asp Ile Arg Tyr Glu  Ser Met Ile Asn Thr  Met Leu Lys
    1550              1555              1560

Asp Leu  Phe Glu Leu Leu Val  Ala Cys Val Ala Lys  Pro Thr Glu
    1565              1570              1575

Thr Ile  Ser Arg Val Gly Cys  Ser Cys Ile Arg Tyr  Val Leu Val
    1580              1585              1590

Thr Ala  Gly Pro Val Phe Thr  Glu Glu Met Trp Arg  Leu Ala Cys
    1595              1600              1605

Cys Ala  Leu Gln Asp Ala Phe  Ser Ala Thr Leu Lys  Pro Val Lys
    1610              1615              1620
```

-continued

```
Asp Leu  Leu Gly Cys Phe His  Ser Gly Thr Glu Ser  Phe Ser Gly
    1625             1630              1635

Glu Gly  Cys Gln Val Arg Val  Ala Ala Pro Ser Ser  Ser Pro Ser
    1640             1645              1650

Ala Glu  Ala Glu Tyr Trp Arg  Ile Arg Ala Met Ala  Gln Gln Val
    1655             1660              1665

Phe Met  Leu Asp Thr Gln Cys  Ser Pro Lys Thr Pro  Asn Asn Phe
    1670             1675              1680

Asp His  Ala Gln Ser Cys Gln  Leu Ile Ile Glu Leu  Pro Pro Asp
    1685             1690              1695

Glu Lys  Pro Asn Gly His Thr  Lys Lys Ser Val Ser  Phe Arg Glu
    1700             1705              1710

Ile Val  Val Ser Leu Leu Ser  His Gln Val Leu Leu  Gln Asn Leu
    1715             1720              1725

Tyr Asp  Ile Leu Leu Glu Glu  Phe Val Lys Gly Pro  Ser Pro Gly
    1730             1735              1740

Glu Glu  Lys Thr Ile Gln Val  Pro Glu Ala Lys Leu  Ala Gly Phe
    1745             1750              1755

Leu Arg  Tyr Ile Ser Met Gln  Asn Leu Ala Val Ile  Phe Asp Leu
    1760             1765              1770

Leu Leu  Asp Ser Tyr Arg Thr  Ala Arg Glu Phe Asp  Thr Ser Pro
    1775             1780              1785

Gly Leu  Lys Cys Leu Leu Lys  Lys Val Ser Gly Ile  Gly Gly Ala
    1790             1795              1800

Ala Asn  Leu Tyr Arg Gln Ser  Ala Met Ser Phe Asn  Ile Tyr Phe
    1805             1810              1815

His Ala  Leu Val Cys Ala Val  Leu Thr Asn Gln Glu  Thr Ile Thr
    1820             1825              1830

Ala Glu  Gln Val Lys Lys Val  Leu Phe Glu Asp Asp  Glu Arg Ser
    1835             1840              1845

Thr Asp  Ser Ser Gln Gln Cys  Ser Ser Glu Asp Glu  Asp Ile Phe
    1850             1855              1860

Glu Glu  Thr Ala Gln Val Ser  Pro Pro Arg Gly Lys  Glu Lys Arg
    1865             1870              1875

Gln Trp  Arg Ala Arg Met Pro  Leu Leu Ser Val Gln  Pro Val Ser
    1880             1885              1890

Asn Ala  Asp Trp Val Trp Leu  Val Lys Arg Leu His  Lys Leu Cys
    1895             1900              1905

Met Glu  Leu Cys Asn Asn Tyr  Ile Gln Met His His Leu  Asp Leu Glu
    1910             1915              1920

Asn Cys  Met Glu Glu Pro Pro  Ile Phe Lys Gly Asp  Pro Phe Phe
    1925             1930              1935

Ile Leu  Pro Ser Phe Gln Ser  Glu Ser Ser Thr Pro  Ser Thr Gly
    1940             1945              1950

Gly Phe  Ser Gly Lys Glu Thr  Pro Ser Glu Asp Asp  Arg Ser Gln
    1955             1960              1965

Ser Arg  Glu His Met Gly Glu  Ser Leu Ser Leu Lys  Ala Gly Gly
    1970             1975              1980

Gly Asp  Leu Leu Leu Pro Pro  Ser Pro Lys Val Glu  Lys Lys Asp
    1985             1990              1995

Pro Ser  Arg Lys Lys Glu Trp  Trp Glu Asn Ala Gly  Asn Lys Ile
    2000             2005              2010
```

```
Tyr Thr  Met Ala Ala Asp Lys  Thr Ile Ser Lys Leu  Met Thr Glu
    2015             2020              2025

Tyr Lys  Lys Arg Lys Gln Gln  His Asn Leu Ser Ala  Phe Pro Lys
    2030             2035              2040

Glu Val  Lys Val Glu Lys Lys  Gly Glu Pro Leu Gly  Pro Arg Gly
    2045             2050              2055

Gln Asp  Ser Pro Leu Leu Gln  Arg Pro Gln His Leu  Met Asp Gln
    2060             2065              2070

Gly Gln  Met Arg His Ser Phe  Ser Ala Gly Pro Glu  Leu Leu Arg
    2075             2080              2085

Gln Asp  Lys Arg Pro Arg Ser  Gly Ser Thr Gly Ser  Ser Leu Ser
    2090             2095              2100

Val Ser  Val Arg Asp Ala Glu  Ala Gln Ile Gln Ala  Trp Thr Asn
    2105             2110              2115

Met Val  Leu Thr Val Leu Asn  Gln Ile Gln Ile Leu  Pro Asp Gln
    2120             2125              2130

Thr Phe  Thr Ala Leu Gln Pro  Ala Val Phe Pro Cys  Ile Ser Gln
    2135             2140              2145

Leu Thr  Cys His Val Thr Asp  Ile Arg Val Arg Gln  Ala Val Arg
    2150             2155              2160

Glu Trp  Leu Gly Arg Val Gly  Arg Val Tyr Asp Ile  Ile Val
    2165             2170              2175
```

<210> SEQ ID NO 33
<211> LENGTH: 13
<212> TYPE: PRT
<213> ORGANISM: Artificial Sequence
<220> FEATURE:
<223> OTHER INFORMATION: PHB2-binding peptide derived from BIG3

<400> SEQUENCE: 33

```
Gln Met Leu Ser Asp Leu Thr Leu Gln Leu Arg Gln Arg
1               5                   10
```

<210> SEQ ID NO 34
<211> LENGTH: 12
<212> TYPE: PRT
<213> ORGANISM: Artificial Sequence
<220> FEATURE:
<223> OTHER INFORMATION: PHB2 peptide No. 34

<400> SEQUENCE: 34

```
Met Ala Gln Asn Leu Lys Asp Leu Ala Gly Arg Leu
1               5                   10
```

<210> SEQ ID NO 35
<211> LENGTH: 12
<212> TYPE: PRT
<213> ORGANISM: Artificial Sequence
<220> FEATURE:
<223> OTHER INFORMATION: PHB2 peptide No. 35

<400> SEQUENCE: 35

```
Gln Asn Leu Lys Asp Leu Ala Gly Arg Leu Pro Ala
1               5                   10
```

<210> SEQ ID NO 36
<211> LENGTH: 12
<212> TYPE: PRT
<213> ORGANISM: Artificial Sequence
<220> FEATURE:
<223> OTHER INFORMATION: PHB2 peptide No. 36

<400> SEQUENCE: 36

Leu Lys Asp Leu Ala Gly Arg Leu Pro Ala Gly Pro
1               5                   10

<210> SEQ ID NO 37
<211> LENGTH: 12
<212> TYPE: PRT
<213> ORGANISM: Artificial Sequence
<220> FEATURE:
<223> OTHER INFORMATION: PHB2 peptide No. 37

<400> SEQUENCE: 37

Asp Leu Ala Gly Arg Leu Pro Ala Gly Pro Arg Gly
1               5                   10

<210> SEQ ID NO 38
<211> LENGTH: 12
<212> TYPE: PRT
<213> ORGANISM: Artificial Sequence
<220> FEATURE:
<223> OTHER INFORMATION: PHB2 peptide No. 38

<400> SEQUENCE: 38

Ala Gly Arg Leu Pro Ala Gly Pro Arg Gly Met Gly
1               5                   10

<210> SEQ ID NO 39
<211> LENGTH: 12
<212> TYPE: PRT
<213> ORGANISM: Artificial Sequence
<220> FEATURE:
<223> OTHER INFORMATION: PHB2 peptide No. 39

<400> SEQUENCE: 39

Pro Ala Gly Pro Arg Gly Met Gly Thr Ala Leu Lys
1               5                   10

<210> SEQ ID NO 40
<211> LENGTH: 12
<212> TYPE: PRT
<213> ORGANISM: Artificial Sequence
<220> FEATURE:
<223> OTHER INFORMATION: PHB2 peptide No. 40

<400> SEQUENCE: 40

Gly Pro Arg Gly Met Gly Thr Ala Leu Lys Leu Leu
1               5                   10

<210> SEQ ID NO 41
<211> LENGTH: 12
<212> TYPE: PRT
<213> ORGANISM: Artificial Sequence
<220> FEATURE:
<223> OTHER INFORMATION: PHB2 peptide No. 41

<400> SEQUENCE: 41

Arg Gly Met Gly Thr Ala Leu Lys Leu Leu Leu Gly
1               5                   10

<210> SEQ ID NO 42
<211> LENGTH: 12
<212> TYPE: PRT
<213> ORGANISM: Artificial Sequence
<220> FEATURE:
<223> OTHER INFORMATION: PHB2 peptide No. 42

```
<400> SEQUENCE: 42

Met Gly Thr Ala Leu Lys Leu Leu Leu Gly Ala Gly
1               5                   10

<210> SEQ ID NO 43
<211> LENGTH: 12
<212> TYPE: PRT
<213> ORGANISM: Artificial Sequence
<220> FEATURE:
<223> OTHER INFORMATION: PHB2 peptide No. 43

<400> SEQUENCE: 43

Thr Ala Leu Lys Leu Leu Leu Gly Ala Gly Ala Val
1               5                   10

<210> SEQ ID NO 44
<211> LENGTH: 15
<212> TYPE: PRT
<213> ORGANISM: Artificial Sequence
<220> FEATURE:
<223> OTHER INFORMATION: PHB2 peptide No. 44

<400> SEQUENCE: 44

Ile Leu Ala Glu Gly Leu His Phe Arg Ile Pro Trp Phe Gln Tyr
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: PHB2 peptide No. 45

<400> SEQUENCE: 45

Ala Glu Gly Leu His Phe Arg Ile Pro Trp Phe Gln Tyr Pro Ile
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: PHB2 peptide No. 46

<400> SEQUENCE: 46

Gly Leu His Phe Arg Ile Pro Trp Phe Gln Tyr Pro Ile Ile Tyr
1               5                   10                  15

<210> SEQ ID NO 47
<211> LENGTH: 14
<212> TYPE: PRT
<213> ORGANISM: Artificial Sequence
<220> FEATURE:
<223> OTHER INFORMATION: PHB2 peptide No. 47

<400> SEQUENCE: 47

His Phe Arg Ile Pro Trp Phe Gln Tyr Pro Ile Ile Tyr Asp
1               5                   10

<210> SEQ ID NO 48
<211> LENGTH: 15
<212> TYPE: PRT
<213> ORGANISM: Artificial Sequence
<220> FEATURE:
<223> OTHER INFORMATION: PHB2 peptide No. 48

<400> SEQUENCE: 48
```

Arg Ile Pro Trp Phe Gln Tyr Pro Ile Ile Tyr Asp Ile Arg Ala
1               5                    10                   15

<210> SEQ ID NO 49
<211> LENGTH: 15
<212> TYPE: PRT
<213> ORGANISM: Artificial Sequence
<220> FEATURE:
<223> OTHER INFORMATION: PHB2 peptide No. 49

<400> SEQUENCE: 49

Pro Trp Phe Gln Tyr Pro Ile Ile Tyr Asp Ile Arg Ala Arg Pro
1               5                    10                   15

<210> SEQ ID NO 50
<211> LENGTH: 15
<212> TYPE: PRT
<213> ORGANISM: Artificial Sequence
<220> FEATURE:
<223> OTHER INFORMATION: PHB2 peptide No. 50

<400> SEQUENCE: 50

Phe Gln Tyr Pro Ile Ile Tyr Asp Ile Arg Ala Arg Pro Arg Lys
1               5                    10                   15

<210> SEQ ID NO 51
<211> LENGTH: 15
<212> TYPE: PRT
<213> ORGANISM: Artificial Sequence
<220> FEATURE:
<223> OTHER INFORMATION: PHB2 peptide No. 51

<400> SEQUENCE: 51

Tyr Pro Ile Ile Tyr Asp Ile Arg Ala Arg Pro Arg Lys Ile Ser
1               5                    10                   15

<210> SEQ ID NO 52
<211> LENGTH: 15
<212> TYPE: PRT
<213> ORGANISM: Artificial Sequence
<220> FEATURE:
<223> OTHER INFORMATION: PHB2 peptide No. 52

<400> SEQUENCE: 52

Ile Ile Tyr Asp Ile Arg Ala Arg Pro Arg Lys Ile Ser Ser Pro
1               5                    10                   15

<210> SEQ ID NO 53
<211> LENGTH: 15
<212> TYPE: PRT
<213> ORGANISM: Artificial Sequence
<220> FEATURE:
<223> OTHER INFORMATION: PHB2 peptide No. 53

<400> SEQUENCE: 53

Tyr Asp Ile Arg Ala Arg Pro Arg Lys Ile Ser Ser Pro Thr Gly
1               5                    10                   15

<210> SEQ ID NO 54
<211> LENGTH: 15
<212> TYPE: PRT
<213> ORGANISM: Artificial Sequence
<220> FEATURE:
<223> OTHER INFORMATION: PHB2 peptide No. 54

<400> SEQUENCE: 54

```
Ile Arg Ala Arg Pro Arg Lys Ile Ser Ser Pro Thr Gly Ser Lys
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: PHB2 peptide No. 55

<400> SEQUENCE: 55

Ala Arg Pro Arg Lys Ile Ser Ser Pro Thr Gly Ser Lys Asp Leu
1               5                   10                  15

<210> SEQ ID NO 56
<211> LENGTH: 12
<212> TYPE: PRT
<213> ORGANISM: Artificial Sequence
<220> FEATURE:
<223> OTHER INFORMATION: PHB2 peptide No. 56

<400> SEQUENCE: 56

Ala Leu Pro Ala Gly Pro Arg Gly Met Gly Thr Ala
1               5                   10

<210> SEQ ID NO 57
<211> LENGTH: 12
<212> TYPE: PRT
<213> ORGANISM: Artificial Sequence
<220> FEATURE:
<223> OTHER INFORMATION: PHB2 peptide No. 57

<400> SEQUENCE: 57

Arg Ala Pro Ala Gly Pro Arg Gly Met Gly Thr Ala
1               5                   10

<210> SEQ ID NO 58
<211> LENGTH: 12
<212> TYPE: PRT
<213> ORGANISM: Artificial Sequence
<220> FEATURE:
<223> OTHER INFORMATION: PHB2 peptide No. 58

<400> SEQUENCE: 58

Arg Leu Ala Ala Gly Pro Arg Gly Met Gly Thr Ala
1               5                   10

<210> SEQ ID NO 59
<211> LENGTH: 12
<212> TYPE: PRT
<213> ORGANISM: Artificial Sequence
<220> FEATURE:
<223> OTHER INFORMATION: PHB2 peptide No. 59

<400> SEQUENCE: 59

Arg Leu Pro Ala Ala Pro Arg Gly Met Gly Thr Ala
1               5                   10

<210> SEQ ID NO 60
<211> LENGTH: 12
<212> TYPE: PRT
<213> ORGANISM: Artificial Sequence
<220> FEATURE:
<223> OTHER INFORMATION: PHB2 peptide No. 60

<400> SEQUENCE: 60

Arg Leu Pro Ala Gly Ala Arg Gly Met Gly Thr Ala
```

```
1               5                   10
```

<210> SEQ ID NO 61
<211> LENGTH: 12
<212> TYPE: PRT
<213> ORGANISM: Artificial Sequence
<220> FEATURE:
<223> OTHER INFORMATION: PHB2 peptide No. 61

<400> SEQUENCE: 61

```
Arg Leu Pro Ala Gly Pro Ala Gly Met Gly Thr Ala
1               5                   10
```

<210> SEQ ID NO 62
<211> LENGTH: 12
<212> TYPE: PRT
<213> ORGANISM: Artificial Sequence
<220> FEATURE:
<223> OTHER INFORMATION: PHB2 peptide No. 62

<400> SEQUENCE: 62

```
Arg Leu Pro Ala Gly Pro Arg Ala Met Gly Thr Ala
1               5                   10
```

<210> SEQ ID NO 63
<211> LENGTH: 12
<212> TYPE: PRT
<213> ORGANISM: Artificial Sequence
<220> FEATURE:
<223> OTHER INFORMATION: PHB2 peptide No. 63

<400> SEQUENCE: 63

```
Arg Leu Pro Ala Gly Pro Arg Gly Ala Gly Thr Ala
1               5                   10
```

<210> SEQ ID NO 64
<211> LENGTH: 12
<212> TYPE: PRT
<213> ORGANISM: Artificial Sequence
<220> FEATURE:
<223> OTHER INFORMATION: PHB2 peptide No. 64

<400> SEQUENCE: 64

```
Arg Leu Pro Ala Gly Pro Arg Gly Met Ala Thr Ala
1               5                   10
```

<210> SEQ ID NO 65
<211> LENGTH: 12
<212> TYPE: PRT
<213> ORGANISM: Artificial Sequence
<220> FEATURE:
<223> OTHER INFORMATION: PHB2 peptide No. 65

<400> SEQUENCE: 65

```
Arg Leu Pro Ala Gly Pro Arg Gly Met Gly Ala Ala
1               5                   10
```

<210> SEQ ID NO 66
<211> LENGTH: 12
<212> TYPE: PRT
<213> ORGANISM: Artificial Sequence
<220> FEATURE:
<223> OTHER INFORMATION: PHB2 peptide No. 66

<400> SEQUENCE: 66

```
Ala Leu Pro Ala Gly Pro Ala Gly Met Gly Thr Ala
1               5                   10
```

```
<210> SEQ ID NO 67
<211> LENGTH: 15
<212> TYPE: PRT
<213> ORGANISM: Artificial Sequence
<220> FEATURE:
<223> OTHER INFORMATION: PHB2 peptide No. 67

<400> SEQUENCE: 67

Ala Tyr Pro Ile Ile Tyr Asp Ile Arg Ala Arg Pro Arg Lys Ile
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: PHB2 peptide No. 68

<400> SEQUENCE: 68

Gln Ala Pro Ile Ile Tyr Asp Ile Arg Ala Arg Pro Arg Lys Ile
1               5                   10                  15

<210> SEQ ID NO 69
<211> LENGTH: 15
<212> TYPE: PRT
<213> ORGANISM: Artificial Sequence
<220> FEATURE:
<223> OTHER INFORMATION: PHB2 peptide No. 69

<400> SEQUENCE: 69

Gln Tyr Ala Ile Ile Tyr Asp Ile Arg Ala Arg Pro Arg Lys Ile
1               5                   10                  15

<210> SEQ ID NO 70
<211> LENGTH: 15
<212> TYPE: PRT
<213> ORGANISM: Artificial Sequence
<220> FEATURE:
<223> OTHER INFORMATION: PHB2 peptide No. 70

<400> SEQUENCE: 70

Gln Tyr Pro Ala Ile Tyr Asp Ile Arg Ala Arg Pro Arg Lys Ile
1               5                   10                  15

<210> SEQ ID NO 71
<211> LENGTH: 15
<212> TYPE: PRT
<213> ORGANISM: Artificial Sequence
<220> FEATURE:
<223> OTHER INFORMATION: PHB2 peptide No. 71

<400> SEQUENCE: 71

Gln Tyr Pro Ile Ala Tyr Asp Ile Arg Ala Arg Pro Arg Lys Ile
1               5                   10                  15

<210> SEQ ID NO 72
<211> LENGTH: 15
<212> TYPE: PRT
<213> ORGANISM: Artificial Sequence
<220> FEATURE:
<223> OTHER INFORMATION: PHB2 peptide No. 72

<400> SEQUENCE: 72

Gln Tyr Pro Ile Ile Ala Asp Ile Arg Ala Arg Pro Arg Lys Ile
1               5                   10                  15
```

<210> SEQ ID NO 73
<211> LENGTH: 15
<212> TYPE: PRT
<213> ORGANISM: Artificial Sequence
<220> FEATURE:
<223> OTHER INFORMATION: PHB2 peptide No. 73

<400> SEQUENCE: 73

Gln Tyr Pro Ile Ile Tyr Ala Ile Arg Ala Arg Pro Arg Lys Ile
1               5                   10                  15

<210> SEQ ID NO 74
<211> LENGTH: 15
<212> TYPE: PRT
<213> ORGANISM: Artificial Sequence
<220> FEATURE:
<223> OTHER INFORMATION: PHB2 peptide No. 74

<400> SEQUENCE: 74

Gln Tyr Pro Ile Ile Tyr Asp Ala Arg Ala Arg Pro Arg Lys Ile
1               5                   10                  15

<210> SEQ ID NO 75
<211> LENGTH: 15
<212> TYPE: PRT
<213> ORGANISM: Artificial Sequence
<220> FEATURE:
<223> OTHER INFORMATION: PHB2 peptide No. 75

<400> SEQUENCE: 75

Gln Tyr Pro Ile Ile Tyr Asp Ile Ala Ala Arg Pro Arg Lys Ile
1               5                   10                  15

<210> SEQ ID NO 76
<211> LENGTH: 15
<212> TYPE: PRT
<213> ORGANISM: Artificial Sequence
<220> FEATURE:
<223> OTHER INFORMATION: PHB2 peptide No. 76

<400> SEQUENCE: 76

Gln Tyr Pro Ile Ile Tyr Asp Ile Arg Ala Ala Pro Arg Lys Ile
1               5                   10                  15

<210> SEQ ID NO 77
<211> LENGTH: 15
<212> TYPE: PRT
<213> ORGANISM: Artificial Sequence
<220> FEATURE:
<223> OTHER INFORMATION: PHB2 peptide No. 77

<400> SEQUENCE: 77

Gln Tyr Pro Ile Ile Tyr Asp Ile Arg Ala Arg Ala Arg Lys Ile
1               5                   10                  15

<210> SEQ ID NO 78
<211> LENGTH: 15
<212> TYPE: PRT
<213> ORGANISM: Artificial Sequence
<220> FEATURE:
<223> OTHER INFORMATION: PHB2 peptide No. 78

<400> SEQUENCE: 78

Gln Tyr Pro Ile Ile Tyr Asp Ile Arg Ala Arg Pro Ala Lys Ile
1               5                   10                  15

-continued

```
<210> SEQ ID NO 79
<211> LENGTH: 15
<212> TYPE: PRT
<213> ORGANISM: Artificial Sequence
<220> FEATURE:
<223> OTHER INFORMATION: PHB2 peptide No. 79

<400> SEQUENCE: 79

Gln Tyr Pro Ile Ile Tyr Asp Ile Arg Ala Arg Pro Arg Ala Ile
1               5                   10                  15

<210> SEQ ID NO 80
<211> LENGTH: 15
<212> TYPE: PRT
<213> ORGANISM: Artificial Sequence
<220> FEATURE:
<223> OTHER INFORMATION: PHB2 peptide No. 80

<400> SEQUENCE: 80

Gln Tyr Pro Ile Ile Tyr Asp Ile Arg Ala Arg Pro Arg Lys Ala
1               5                   10                  15

<210> SEQ ID NO 81
<211> LENGTH: 15
<212> TYPE: PRT
<213> ORGANISM: Artificial Sequence
<220> FEATURE:
<223> OTHER INFORMATION: PHB2 peptide No. 81

<400> SEQUENCE: 81

Gln Ala Pro Ile Ile Tyr Asp Ile Ala Ala Arg Pro Arg Lys Ile
1               5                   10                  15

<210> SEQ ID NO 82
<211> LENGTH: 14
<212> TYPE: PRT
<213> ORGANISM: Artificial Sequence
<220> FEATURE:
<223> OTHER INFORMATION: PHB2 peptide No. 82

<400> SEQUENCE: 82

Glu Gly Gly His Arg Ala Ile Phe Phe Asn Arg Ile Gly Gly
1               5                   10

<210> SEQ ID NO 83
<211> LENGTH: 20
<212> TYPE: PRT
<213> ORGANISM: Artificial Sequence
<220> FEATURE:
<223> OTHER INFORMATION: PHB2 peptide No. 83

<400> SEQUENCE: 83

Glu Ser Val Phe Thr Val Glu Gly Gly His Arg Ala Ile Phe Phe Asn
1               5                   10                  15

Arg Ile Gly Gly
            20

<210> SEQ ID NO 84
<211> LENGTH: 11
<212> TYPE: PRT
<213> ORGANISM: Artificial Sequence
<220> FEATURE:
<223> OTHER INFORMATION: PHB2 derived peptide 11-21aa

<400> SEQUENCE: 84

Arg Leu Pro Ala Gly Pro Arg Gly Met Gly Thr
1               5                   10
```

```
<210> SEQ ID NO 85
<211> LENGTH: 13
<212> TYPE: PRT
<213> ORGANISM: Artificial Sequence
<220> FEATURE:
<223> OTHER INFORMATION: PHB2 derived peptide 76-88aa

<400> SEQUENCE: 85

Gln Tyr Pro Ile Ile Tyr Asp Ile Arg Ala Arg Pro Arg
1               5                   10

<210> SEQ ID NO 86
<211> LENGTH: 6330
<212> TYPE: DNA
<213> ORGANISM: Homo sapiens
<220> FEATURE:
<221> NAME/KEY: CDS
<222> LOCATION: (235)..(2022)

<400> SEQUENCE: 86
aggagctggc ggagggcgtt cgtcctggga ctgcacttgc tcccgtcggg tcgcccggct       60
tcaccggacc cgcaggctcc cggggcaggg ccggggccag agctcgcgtg tcggcgggac      120
atgcgctgcg tcgcctctaa cctcgggctg tgctcttttt ccaggtggcc cgccggtttc      180
tgagccttct gccctgcggg gacacggtct gcaccctgcc cgcggccacg gacc atg       237
                                                            Met
                                                            1 acc atg acc ctc cac acc aaa gca tct ggg atg gcc cta ctg cat cag       285
Thr Met Thr Leu His Thr Lys Ala Ser Gly Met Ala Leu Leu His Gln
        5                   10                  15 atc caa ggg aac gag ctg gag ccc ctg aac cgt ccg cag ctc aag atc       333
Ile Gln Gly Asn Glu Leu Glu Pro Leu Asn Arg Pro Gln Leu Lys Ile
            20                  25                  30 ccc ctg gag cgg ccc ctg ggc gag gtg tac ctg gac agc agc aag ccc       381
Pro Leu Glu Arg Pro Leu Gly Glu Val Tyr Leu Asp Ser Ser Lys Pro
    35                  40                  45 gcc gtg tac aac tac ccc gag ggc gcc gcc tac gag ttc aac gcc gcg       429
Ala Val Tyr Asn Tyr Pro Glu Gly Ala Ala Tyr Glu Phe Asn Ala Ala
50                  55                  60                  65 gcc gcc gcc aac gcg cag gtc tac ggt cag acc ggc ctc ccc tac ggc       477
Ala Ala Ala Asn Ala Gln Val Tyr Gly Gln Thr Gly Leu Pro Tyr Gly
                70                  75                  80 ccc ggg tct gag gct gcg gcg ttc ggc tcc aac ggc ctg ggg ggt ttc       525
Pro Gly Ser Glu Ala Ala Ala Phe Gly Ser Asn Gly Leu Gly Gly Phe
                85                  90                  95 ccc cca ctc aac agc gtg tct ccg agc ccg ctg atg cta ctg cac ccg       573
Pro Pro Leu Asn Ser Val Ser Pro Ser Pro Leu Met Leu Leu His Pro
            100                 105                 110 ccg ccg cag ctg tcg cct ttc ctg cag ccc cac ggc cag cag gtg ccc       621
Pro Pro Gln Leu Ser Pro Phe Leu Gln Pro His Gly Gln Gln Val Pro
        115                 120                 125 tac tac ctg gag aac gag ccc agc ggc tac acg gtg cgc gag gcc ggc       669
Tyr Tyr Leu Glu Asn Glu Pro Ser Gly Tyr Thr Val Arg Glu Ala Gly
130                 135                 140                 145 ccg ccg gca ttc tac agg cca aat tca gat aat cga cgc cag ggt ggc       717
Pro Pro Ala Phe Tyr Arg Pro Asn Ser Asp Asn Arg Arg Gln Gly Gly
                150                 155                 160 aga gaa aga ttg gcc agt acc aat gac aag gga agt atg gct atg gaa       765
Arg Glu Arg Leu Ala Ser Thr Asn Asp Lys Gly Ser Met Ala Met Glu
            165                 170                 175
```

-continued

```
tct gcc aag gag act cgc tac tgt gca gtg tgc aat gac tat gct tca      813
Ser Ala Lys Glu Thr Arg Tyr Cys Ala Val Cys Asn Asp Tyr Ala Ser
        180                 185                 190 ggc tac cat tat gga gtc tgg tcc tgt gag ggc tgc aag gcc ttc ttc      861
Gly Tyr His Tyr Gly Val Trp Ser Cys Glu Gly Cys Lys Ala Phe Phe
        195                 200                 205 aag aga agt att caa gga cat aac gac tat atg tgt cca gcc acc aac      909
Lys Arg Ser Ile Gln Gly His Asn Asp Tyr Met Cys Pro Ala Thr Asn
210                 215                 220                 225 cag tgc acc att gat aaa aac agg agg aag agc tgc cag gcc tgc cgg      957
Gln Cys Thr Ile Asp Lys Asn Arg Arg Lys Ser Cys Gln Ala Cys Arg
                230                 235                 240 ctc cgc aaa tgc tac gaa gtg gga atg atg aaa ggt ggg ata cga aaa     1005
Leu Arg Lys Cys Tyr Glu Val Gly Met Met Lys Gly Gly Ile Arg Lys
                245                 250                 255 gac cga aga gga ggg aga atg ttg aaa cac aag cgc cag aga gat gat     1053
Asp Arg Arg Gly Gly Arg Met Leu Lys His Lys Arg Gln Arg Asp Asp
                260                 265                 270 ggg gag ggc agg ggt gaa gtg ggg tct gct gga gac atg aga gct gcc     1101
Gly Glu Gly Arg Gly Glu Val Gly Ser Ala Gly Asp Met Arg Ala Ala
        275                 280                 285 aac ctt tgg cca agc ccg ctc atg atc aaa cgc tct aag aag aac agc     1149
Asn Leu Trp Pro Ser Pro Leu Met Ile Lys Arg Ser Lys Lys Asn Ser
290                 295                 300                 305 ctg gcc ttg tcc ctg acg gcc gac cag atg gtc agt gcc ttg ttg gat     1197
Leu Ala Leu Ser Leu Thr Ala Asp Gln Met Val Ser Ala Leu Leu Asp
                310                 315                 320 gct gag ccc ccc ata ctc tat tcc gag tat gat cct acc aga ccc ttc     1245
Ala Glu Pro Pro Ile Leu Tyr Ser Glu Tyr Asp Pro Thr Arg Pro Phe
                325                 330                 335 agt gaa gct tcg atg atg ggc tta ctc acc aac ctg gca gac agg gag     1293
Ser Glu Ala Ser Met Met Gly Leu Leu Thr Asn Leu Ala Asp Arg Glu
        340                 345                 350 ctg gtt cac atg atc aac tgg gcg aag agg gtg cca ggc ttt gtg gat     1341
Leu Val His Met Ile Asn Trp Ala Lys Arg Val Pro Gly Phe Val Asp
        355                 360                 365 ttg acc ctc cat gat cag gtc cac ctt cta gaa tgt gcc tgg cta gag     1389
Leu Thr Leu His Asp Gln Val His Leu Leu Glu Cys Ala Trp Leu Glu
370                 375                 380                 385 atc ctg atg att ggt ctc gtc tgg cgc tcc atg gag cac cca ggg aag     1437
Ile Leu Met Ile Gly Leu Val Trp Arg Ser Met Glu His Pro Gly Lys
                390                 395                 400 cta ctg ttt gct cct aac ttg ctc ttg gac agg aac cag gga aaa tgt     1485
Leu Leu Phe Ala Pro Asn Leu Leu Leu Asp Arg Asn Gln Gly Lys Cys
                405                 410                 415 gta gag ggc atg gtg gag atc ttc gac atg ctg ctg gct aca tca tct     1533
Val Glu Gly Met Val Glu Ile Phe Asp Met Leu Leu Ala Thr Ser Ser
        420                 425                 430 cgg ttc cgc atg atg aat ctg cag gga gag gag ttt gtg tgc ctc aaa     1581
Arg Phe Arg Met Met Asn Leu Gln Gly Glu Glu Phe Val Cys Leu Lys
        435                 440                 445 tct att att ttg ctt aat tct gga gtg tac aca ttt ctg tcc agc acc     1629
Ser Ile Ile Leu Leu Asn Ser Gly Val Tyr Thr Phe Leu Ser Ser Thr
450                 455                 460                 465 ctg aag tct ctg gaa gag aag gac cat atc cac cga gtc ctg gac aag     1677
Leu Lys Ser Leu Glu Glu Lys Asp His Ile His Arg Val Leu Asp Lys
                470                 475                 480 atc aca gac act ttg atc cac ctg atg gcc aag gca ggc ctg acc ctg     1725
Ile Thr Asp Thr Leu Ile His Leu Met Ala Lys Ala Gly Leu Thr Leu
                485                 490                 495
```

-continued

```
cag cag cag cac cag cgg ctg gcc cag ctc ctc ctc atc ctc tcc cac     1773
Gln Gln Gln His Gln Arg Leu Ala Gln Leu Leu Leu Ile Leu Ser His
        500             505             510 atc agg cac atg agt aac aaa ggc atg gag cat ctg tac agc atg aag     1821
Ile Arg His Met Ser Asn Lys Gly Met Glu His Leu Tyr Ser Met Lys
        515             520             525 tgc aag aac gtg gtg ccc ctc tat gac ctg ctg ctg gag atg ctg gac     1869
Cys Lys Asn Val Val Pro Leu Tyr Asp Leu Leu Leu Glu Met Leu Asp
530             535             540             545 gcc cac cgc cta cat gcg ccc act agc cgt gga ggg gca tcc gtg gag     1917
Ala His Arg Leu His Ala Pro Thr Ser Arg Gly Gly Ala Ser Val Glu
                550             555             560 gag acg gac caa agc cac ttg gcc act gcg ggc tct act tca tcg cat     1965
Glu Thr Asp Gln Ser His Leu Ala Thr Ala Gly Ser Thr Ser Ser His
                565             570             575 tcc ttg caa aag tat tac atc acg ggg gag gca gag ggt ttc cct gcc     2013
Ser Leu Gln Lys Tyr Tyr Ile Thr Gly Glu Ala Glu Gly Phe Pro Ala
        580             585             590 acg gtc tga gagctccctg gctcccacac ggttcagata atccctgctg             2062
Thr Val
    595 cattttaccc tcatcatgca ccactttagc caaattctgt ctcctgcata cactccggca     2122 tgcatccaac accaatggct ttctagatga gtggccattc atttgcttgc tcagttctta     2182 gtggcacatc ttctgtcttc tgttgggaac agccaaaggg attccaaggc taaatctttg     2242 taacagctct ctttcccct tgctatgtta ctaagcgtga ggattcccgt agctcttcac     2302 agctgaactc agtctatggg ttggggctca gataactctg tgcatttaag ctacttgtag     2362 agacccaggc ctggagagta gacattttgc ctctgataag cactttttaa atggctctaa     2422 gaataagcca cagcaaagaa tttaaagtgg ctcctttaat tggtgacttg agaaaagcta     2482 ggtcaagggt ttattatagc accctcttgt attcctatgg caatgcatcc ttttatgaaa     2542 gtggtacacc ttaaagcttt tatatgactg tagcagagta tctggtgatt gtcaattcat     2602 tcccctata ggaatacaag gggcacacag ggaaggcaga tcccctagtt ggcaagacta      2662 ttttaacttg atacactgca gattcagatg tgctgaaagc tctgcctctg gctttccggt     2722 catgggttcc agttaattca tgcctcccat ggacctatgg agagcagcaa gttgatctta     2782 gttaagtctc cctatatgag ggataagttc ctgatttttg ttttttatttt tgtgttacaa    2842 aagaaagccc tccctccctg aacttgcagt aaggtcagct tcaggacctg ttccagtggg     2902 cactgtactt ggatcttccc ggcgtgtgtg tgccttacac aggggtgaac tgttcactgt     2962 ggtgatgcat gatgagggta aatggtagtt gaaaggagca ggggccctgg tgttgcattt     3022 agccctgggg catggagctg aacagtactt gtgcaggatt gttgtggcta ctagagaaca     3082 agagggaaag tagggcagaa actggataca gttctgaggc acagccagac ttgctcaggg     3142 tggccctgcc acaggctgca gctacctagg aacattcctt gcagaccccg cattgccctt     3202 tggggggtgcc ctgggatccc tggggtagtc cagctcttct tcatttccca gcgtggccct    3262 ggttggaaga agcagctgtc acagctgctg tagacagctg tgttcctaca attggcccag     3322 caccctgggg cacgggagaa gggtggggac cgttgctgtc actactcagg ctgactgggg     3382 cctggtcaga ttacgtatgc ccttggtggt ttagagataa tccaaaatca gggtttggtt     3442 tggggaagaa aatcctcccc cttcctcccc cgccccgttc cctaccgcct ccactcctgc     3502 cagctcattt ccttcaattt cctttgacct ataggctaaa aaagaaaggc tcattccagc     3562
```

-continued

```
cacagggcag ccttccctgg gcctttgctt ctctagcaca attatgggtt acttcctttt   3622
tcttaacaaa aaagaatgtt tgatttcctc tgggtgacct tattgtctgt aattgaaacc   3682
ctattgagag gtgatgtctg tgttagccaa tgacccaggt gagctgctcg ggcttctctt   3742
ggtatgtctt gtttggaaaa gtggatttca ttcatttctg attgtccagt taagtgatca   3802
ccaaaggact gagaatctgg gagggcaaaa aaaaaaaaa agtttttatg tgcacttaaa   3862 tttgggaca attttatgta tctgtgttaa ggatatgttt aagaacataa ttcttttgtt   3922
gctgtttgtt taagaagcac cttagtttgt ttaagaagca ccttatatag tataatatat   3982
atttttttga aattacattg cttgtttatc agacaattga atgtagtaat tctgttctgg   4042
atttaatttg actgggttaa catgcaaaaa ccaaggaaaa atatttagtt tttttttttt   4102
tttttgtata cttttcaagc taccttgtca tgtatacagt catttatgcc taaagcctgg   4162
tgattattca tttaaatgaa gatcacattt catatcaact tttgtatcca cagtagacaa   4222
aatagcacta atccagatgc ctattgttgg atactgaatg acagacaatc ttatgtagca   4282
aagattatgc ctgaaaagga aaattattca gggcagctaa ttttgctttt accaaaatat   4342
cagtagtaat attttttggac agtagctaat gggtcagtgg gttctttta atgtttatac   4402 ttagattttc ttttaaaaaa attaaaataa aacaaaaaaa aatttctagg actagacgat   4462
gtaataccag ctaaagccaa acaattatac agtggaaggt tttacattat tcatccaatg   4522
tgtttctatt catgttaaga tactactaca tttgaagtgg gcagagaaca tcagatgatt   4582
gaaatgttcg cccaggggtc tccagcaact ttggaaatct ctttgtattt ttacttgaag   4642
tgccactaat ggacagcaga tattttctgg ctgatgttgg tattgggtgt aggaacatga   4702
tttaaaaaaa aactcttgcc tctgctttcc cccactctga ggcaagttaa aatgtaaaag   4762
atgtgattta tctggggggc tcaggtatgg tggggaagtg gattcaggaa tctggggaat   4822
ggcaaatata ttaagaagag tattgaaagt atttggagga aaatggttaa ttctgggtgt   4882
gcaccagggt tcagtagagt ccacttctgc cctggagacc acaaatcaac tagctccatt   4942
tacagccatt tctaaaatgg cagcttcagt tctagagaag aaagaacaac atcagcagta   5002
aagtccatgg aatagctagt ggtctgtgtt tcttttcgcc attgcctagc ttgccgtaat   5062
gattctataa tgccatcatg cagcaattat gagaggctag gtcatccaaa gagaagaccc   5122
tatcaatgta ggttgcaaaa tctaacccct aaggaagtgc agtctttgat ttgatttccc   5182
tagtaacctt gcagatatgt ttaaccaagc catagcccat gccttttgag ggctgaacaa   5242
ataagggact tactgataat ttacttttga tcacattaag gtgttctcac cttgaaatct   5302
tatacactga aatggccatt gatttaggcc actggcttag agtactcctt cccctgcatg   5362
acactgatta caaatacttt cctattcata cttttccaatt atgagatgga ctgtgggtac   5422
tgggagtgat cactaacacc atagtaatgt ctaatattca caggcagatc tgcttgggga   5482
agctagttat gtgaaaggca aatagagtca tacagtagct caaaaggcaa ccataattct   5542
ctttggtgca ggtcttggga gcgtgatcta gattacactg caccattccc aagttaatcc   5602
cctgaaaact tactctcaac tggagcaaat gaactttggt cccaaatatc catcttttca   5662
gtagcgttaa ttatgctctg tttccaactg catttccttt ccaattgaat taaagtgtgg   5722
cctcgttttt agtcatttaa aattgttttc taagtaattg ctgcctctat tatggcactt   5782
caattttgca ctgtcttttg agattcaaga aaaatttcta ttcttttttt tgcatccaat   5842
tgtgcctgaa cttttaaaat atgtaaatgc tgccatgttc caaacccatc gtcagtgtgt   5902
gtgtttagag ctgtgcaccc tagaaacaac atattgtccc atgagcaggt gcctgagaca   5962
```

```
cagaccccctt tgcattcaca gagaggtcat tggttataga gacttgaatt aataagtgac    6022
attatgccag tttctgttct ctcacaggtg ataaacaatg cttttttgtgc actacatact    6082 cttcagtgta gagctcttgt tttatgggaa aaggctcaaa tgccaaattg tgtttgatgg    6142
attaatatgc cctttttgccg atgcatacta ttactgatgt gactcggttt tgtcgcagct    6202
ttgctttgtt taatgaaaca cacttgtaaa cctcttttgc actttgaaaa agaatccagc    6262
gggatgctcg agcacctgta aacaattttc tcaacctatt tgatgttcaa ataaagaatt    6322
aaactaaa                                                                6330
```

```
<210> SEQ ID NO 87
<211> LENGTH: 595
<212> TYPE: PRT
<213> ORGANISM: Homo sapiens

<400> SEQUENCE: 87

Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
                20                  25                  30

Ile Pro Leu Glu Arg Pro Leu Gly Glu Val Tyr Leu Asp Ser Ser Lys
            35                  40                  45

Pro Ala Val Tyr Asn Tyr Pro Glu Gly Ala Ala Tyr Glu Phe Asn Ala
        50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His
                100                 105                 110

Pro Pro Pro Gln Leu Ser Pro Phe Leu Gln Pro His Gly Gln Gln Val
            115                 120                 125

Pro Tyr Tyr Leu Glu Asn Glu Pro Ser Gly Tyr Thr Val Arg Glu Ala
        130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
        195                 200                 205

Phe Lys Arg Ser Ile Gln Gly His Asn Asp Tyr Met Cys Pro Ala Thr
        210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
                260                 265                 270

Asp Gly Glu Gly Arg Gly Glu Val Gly Ser Ala Gly Asp Met Arg Ala
            275                 280                 285

Ala Asn Leu Trp Pro Ser Pro Leu Met Ile Lys Arg Ser Lys Lys Asn
        290                 295                 300
```

-continued

```
Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
        355                 360                 365

Asp Leu Thr Leu His Asp Gln Val His Leu Leu Glu Cys Ala Trp Leu
    370                 375                 380

Glu Ile Leu Met Ile Gly Leu Val Trp Arg Ser Met Glu His Pro Gly
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
            420                 425                 430

Ser Arg Phe Arg Met Met Asn Leu Gln Gly Glu Glu Phe Val Cys Leu
        435                 440                 445

Lys Ser Ile Ile Leu Leu Asn Ser Gly Val Tyr Thr Phe Leu Ser Ser
    450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
            500                 505                 510

His Ile Arg His Met Ser Asn Lys Gly Met Glu His Leu Tyr Ser Met
        515                 520                 525

Lys Cys Lys Asn Val Val Pro Leu Tyr Asp Leu Leu Leu Glu Met Leu
    530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe Pro
            580                 585                 590

Ala Thr Val
        595
```

```
<210> SEQ ID NO 88
<211> LENGTH: 2169
<212> TYPE: DNA
<213> ORGANISM: Homo sapiens
<220> FEATURE:
<221> NAME/KEY: CDS
<222> LOCATION: (469)..(2061)

<400> SEQUENCE: 88
ctcggtcttt aaaaggaaga aggggcttat cgttaagtcg cttgtgatct tttcagtttc      60
tccagctgct ggcttttgg acacccactc ccccgccagg aggcagttgc aagcgcggag      120
gctgcgagaa ataactgcct cttgaaactt gcagggcgaa gagcaggcgg cgagcgctgg      180 gccgggagg gaccacccga gctgcgacgg gctctggggc tgcggggcag ggctggcgcc      240
cggagcctga gctgcaggag gtgcgctcgc tttcctcaac aggtggcggc ggggcgcgcg      300
```

```
ccgggagacc cccctaatg cgggaaaagc acgtgtccgc attttagaga aggcaaggcc      360
ggtgtgttta tctgcaagcc attatacttg cccacgaatc tttgagaaca ttataatgac      420
ctttgtgcct cttcttgcaa ggtgttttct cagctgttat ctcaagac atg gat ata      477
                                                       Met Asp Ile
                                                        1 aaa aac tca cca tct agc ctt aat tct cct tcc tcc tac aac tgc agt      525
Lys Asn Ser Pro Ser Ser Leu Asn Ser Pro Ser Ser Tyr Asn Cys Ser
      5              10                  15 caa tcc atc tta ccc ctg gag cac ggc tcc ata tac ata cct tcc tcc      573
Gln Ser Ile Leu Pro Leu Glu His Gly Ser Ile Tyr Ile Pro Ser Ser
20              25                  30                  35 tat gta gac agc cac cat gaa tat cca gcc atg aca ttc tat agc cct      621
Tyr Val Asp Ser His His Glu Tyr Pro Ala Met Thr Phe Tyr Ser Pro
              40                  45                  50 gct gtg atg aat tac agc att ccc agc aat gtc act aac ttg gaa ggt      669
Ala Val Met Asn Tyr Ser Ile Pro Ser Asn Val Thr Asn Leu Glu Gly
              55                  60                  65 ggg cct ggt cgg cag acc aca agc cca aat gtg ttg tgg cca aca cct      717
Gly Pro Gly Arg Gln Thr Thr Ser Pro Asn Val Leu Trp Pro Thr Pro
          70                  75                  80 ggg cac ctt tct cct tta gtg gtc cat cgc cag tta tca cat ctg tat      765
Gly His Leu Ser Pro Leu Val Val His Arg Gln Leu Ser His Leu Tyr
      85                  90                  95 gcg gaa cct caa aag agt ccc tgg tgt gaa gca aga tcg cta gaa cac      813
Ala Glu Pro Gln Lys Ser Pro Trp Cys Glu Ala Arg Ser Leu Glu His
100                 105                 110                 115 acc tta cct gta aac aga gag aca ctg aaa agg aag gtt agt ggg aac      861
Thr Leu Pro Val Asn Arg Glu Thr Leu Lys Arg Lys Val Ser Gly Asn
                120                 125                 130 cgt tgc gcc agc cct gtt act ggt cca ggt tca aag agg gat gct cac      909
Arg Cys Ala Ser Pro Val Thr Gly Pro Gly Ser Lys Arg Asp Ala His
              135                 140                 145 ttc tgc gct gtc tgc agc gat tac gca tcg gga tat cac tat gga gtc      957
Phe Cys Ala Val Cys Ser Asp Tyr Ala Ser Gly Tyr His Tyr Gly Val
              150                 155                 160 tgg tcg tgt gaa gga tgt aag gcc ttt ttt aaa aga agc att caa gga     1005
Trp Ser Cys Glu Gly Cys Lys Ala Phe Phe Lys Arg Ser Ile Gln Gly
          165                 170                 175 cat aat gat tat att tgt cca gct aca aat cag tgt aca atc gat aaa     1053
His Asn Asp Tyr Ile Cys Pro Ala Thr Asn Gln Cys Thr Ile Asp Lys
180                 185                 190                 195 aac cgg cgc aag agc tgc cag gcc tgc cga ctt cgg aag tgt tac gaa     1101
Asn Arg Arg Lys Ser Cys Gln Ala Cys Arg Leu Arg Lys Cys Tyr Glu
                200                 205                 210 gtg gga atg gtg aag tgt ggc tcc cgg aga gag aga tgt ggg tac cgc     1149
Val Gly Met Val Lys Cys Gly Ser Arg Arg Glu Arg Cys Gly Tyr Arg
              215                 220                 225 ctt gtg cgg aga cag aga agt gcc gac gag cag ctg cac tgt gcc ggc     1197
Leu Val Arg Arg Gln Arg Ser Ala Asp Glu Gln Leu His Cys Ala Gly
              230                 235                 240 aag gcc aag aga agt ggc ggc cac gcg ccc cga gtg cgg gag ctg ctg     1245
Lys Ala Lys Arg Ser Gly Gly His Ala Pro Arg Val Arg Glu Leu Leu
      245                 250                 255 ctg gac gcc ctg agc ccc gag cag cta gtg ctc acc ctc ctg gag gct     1293
Leu Asp Ala Leu Ser Pro Glu Gln Leu Val Leu Thr Leu Leu Glu Ala
260                 265                 270                 275 gag ccg ccc cat gtg ctg atc agc cgc ccc agt gcg ccc ttc acc gag     1341
Glu Pro Pro His Val Leu Ile Ser Arg Pro Ser Ala Pro Phe Thr Glu
                280                 285                 290
```

-continued

```
gcc tcc atg atg atg tcc ctg acc aag ttg gcc gac aag gag ttg gta      1389
Ala Ser Met Met Met Ser Leu Thr Lys Leu Ala Asp Lys Glu Leu Val
            295                 300                 305 cac atg atc agc tgg gcc aag aag att ccc ggc ttt gtg gag ctc agc      1437
His Met Ile Ser Trp Ala Lys Lys Ile Pro Gly Phe Val Glu Leu Ser
            310                 315                 320 ctg ttc gac caa gtg cgg ctc ttg gag agc tgt tgg atg gag gtg tta      1485
Leu Phe Asp Gln Val Arg Leu Leu Glu Ser Cys Trp Met Glu Val Leu
            325                 330                 335 atg atg ggg ctg atg tgg cgc tca att gac cac ccc ggc aag ctc atc      1533
Met Met Gly Leu Met Trp Arg Ser Ile Asp His Pro Gly Lys Leu Ile
340                 345                 350                 355 ttt gct cca gat ctt gtt ctg gac agg gat gag ggg aaa tgc gta gaa      1581
Phe Ala Pro Asp Leu Val Leu Asp Arg Asp Glu Gly Lys Cys Val Glu
                360                 365                 370 gga att ctg gaa atc ttt gac atg ctc ctg gca act act tca agg ttt      1629
Gly Ile Leu Glu Ile Phe Asp Met Leu Leu Ala Thr Thr Ser Arg Phe
            375                 380                 385 cga gag tta aaa ctc caa cac aaa gaa tat ctc tgt gtc aag gcc atg      1677
Arg Glu Leu Lys Leu Gln His Lys Glu Tyr Leu Cys Val Lys Ala Met
            390                 395                 400 atc ctg ctc aat tcc agt atg tac cct ctg gtc aca gcg acc cag gat      1725
Ile Leu Leu Asn Ser Ser Met Tyr Pro Leu Val Thr Ala Thr Gln Asp
            405                 410                 415 gct gac agc agc cgg aag ctg gct cac ttg ctg aac gcc gtg acc gat      1773
Ala Asp Ser Ser Arg Lys Leu Ala His Leu Leu Asn Ala Val Thr Asp
420                 425                 430                 435 gct ttg gtt tgg gtg att gcc aag agc ggc atc tcc tcc cag cag caa      1821
Ala Leu Val Trp Val Ile Ala Lys Ser Gly Ile Ser Ser Gln Gln Gln
                440                 445                 450 tcc atg cgc ctg gct aac ctc ctg atg ctc ctg tcc cac gtc agg cat      1869
Ser Met Arg Leu Ala Asn Leu Leu Met Leu Leu Ser His Val Arg His
            455                 460                 465 gcg agt aac aag ggc atg gaa cat ctg ctc aac atg aag tgc aaa aat      1917
Ala Ser Asn Lys Gly Met Glu His Leu Leu Asn Met Lys Cys Lys Asn
            470                 475                 480 gtg gtc cca gtg tat gac ctg ctg ctg gag atg ctg aat gcc cac gtg      1965
Val Val Pro Val Tyr Asp Leu Leu Leu Glu Met Leu Asn Ala His Val
            485                 490                 495 ctt cgc ggg tgc aag tcc tcc atc acg ggg tcc gag tgc agc ccg gca      2013
Leu Arg Gly Cys Lys Ser Ser Ile Thr Gly Ser Glu Cys Ser Pro Ala
500                 505                 510                 515 gag gac agt aaa agc aaa gag ggc tcc cag aac cca cag tct cag tga      2061
Glu Asp Ser Lys Ser Lys Glu Gly Ser Gln Asn Pro Gln Ser Gln
                520                 525                 530 cgcctggccc tgaggtgaac tggcccacag aggtcacagg ctgaagcgtg aactccagtg      2121
tgtcaggagc ctgggcttca tctttctgct gtgtggtccc tcatttgg                   2169
```

<210> SEQ ID NO 89
<211> LENGTH: 530
<212> TYPE: PRT
<213> ORGANISM: Homo sapiens

<400> SEQUENCE: 89

```
Met Asp Ile Lys Asn Ser Pro Ser Ser Leu Asn Ser Pro Ser Ser Tyr
1               5                   10                  15

Asn Cys Ser Gln Ser Ile Leu Pro Leu Glu His Gly Ser Ile Tyr Ile
                20                  25                  30
```

```
Pro Ser Ser Tyr Val Asp Ser His His Glu Tyr Pro Ala Met Thr Phe
        35              40              45

Tyr Ser Pro Ala Val Met Asn Tyr Ser Ile Pro Ser Asn Val Thr Asn
    50              55              60

Leu Glu Gly Gly Pro Gly Arg Gln Thr Thr Ser Pro Asn Val Leu Trp
65              70              75              80

Pro Thr Pro Gly His Leu Ser Pro Leu Val Val His Arg Gln Leu Ser
            85              90              95

His Leu Tyr Ala Glu Pro Gln Lys Ser Pro Trp Cys Glu Ala Arg Ser
            100             105             110

Leu Glu His Thr Leu Pro Val Asn Arg Glu Thr Leu Lys Arg Lys Val
        115             120             125

Ser Gly Asn Arg Cys Ala Ser Pro Val Thr Gly Pro Gly Ser Lys Arg
    130             135             140

Asp Ala His Phe Cys Ala Val Cys Ser Asp Tyr Ala Ser Gly Tyr His
145             150             155             160

Tyr Gly Val Trp Ser Cys Glu Gly Cys Lys Ala Phe Phe Lys Arg Ser
            165             170             175

Ile Gln Gly His Asn Asp Tyr Ile Cys Pro Ala Thr Asn Gln Cys Thr
            180             185             190

Ile Asp Lys Asn Arg Arg Lys Ser Cys Gln Ala Cys Arg Leu Arg Lys
        195             200             205

Cys Tyr Glu Val Gly Met Val Lys Cys Gly Ser Arg Arg Glu Arg Cys
    210             215             220

Gly Tyr Arg Leu Val Arg Arg Gln Arg Ser Ala Asp Glu Gln Leu His
225             230             235             240

Cys Ala Gly Lys Ala Lys Arg Ser Gly Gly His Ala Pro Arg Val Arg
            245             250             255

Glu Leu Leu Leu Asp Ala Leu Ser Pro Glu Gln Leu Val Leu Thr Leu
            260             265             270

Leu Glu Ala Glu Pro Pro His Val Leu Ile Ser Arg Pro Ser Ala Pro
        275             280             285

Phe Thr Glu Ala Ser Met Met Met Ser Leu Thr Lys Leu Ala Asp Lys
    290             295             300

Glu Leu Val His Met Ile Ser Trp Ala Lys Lys Ile Pro Gly Phe Val
305             310             315             320

Glu Leu Ser Leu Phe Asp Gln Val Arg Leu Leu Glu Ser Cys Trp Met
            325             330             335

Glu Val Leu Met Met Gly Leu Met Trp Arg Ser Ile Asp His Pro Gly
            340             345             350

Lys Leu Ile Phe Ala Pro Asp Leu Val Leu Asp Arg Asp Glu Gly Lys
        355             360             365

Cys Val Glu Gly Ile Leu Glu Ile Phe Asp Met Leu Leu Ala Thr Thr
    370             375             380

Ser Arg Phe Arg Glu Leu Lys Leu Gln His Lys Glu Tyr Leu Cys Val
385             390             395             400

Lys Ala Met Ile Leu Leu Asn Ser Ser Met Tyr Pro Leu Val Thr Ala
            405             410             415

Thr Gln Asp Ala Asp Ser Ser Arg Lys Leu Ala His Leu Leu Asn Ala
            420             425             430

Val Thr Asp Ala Leu Val Trp Val Ile Ala Lys Ser Gly Ile Ser Ser
        435             440             445

Gln Gln Gln Ser Met Arg Leu Ala Asn Leu Leu Met Leu Leu Ser His
```

-continued

```
       450                455                460

Val Arg His Ala Ser Asn Lys Gly Met Glu His Leu Leu Asn Met Lys
465                470                475                480

Cys Lys Asn Val Val Pro Val Tyr Asp Leu Leu Leu Glu Met Leu Asn
                485                490                495

Ala His Val Leu Arg Gly Cys Lys Ser Ser Ile Thr Gly Ser Glu Cys
                500                505                510

Ser Pro Ala Glu Asp Ser Lys Ser Lys Glu Gly Ser Gln Asn Pro Gln
        515                520                525

Ser Gln
    530

<210> SEQ ID NO 90
<211> LENGTH: 9
<212> TYPE: PRT
<213> ORGANISM: Artificial Sequence
<220> FEATURE:
<223> OTHER INFORMATION: A cell membrane permeable peptide

<400> SEQUENCE: 90

Arg Lys Lys Arg Arg Gln Arg Arg Arg
1               5

<210> SEQ ID NO 91
<211> LENGTH: 21
<212> TYPE: PRT
<213> ORGANISM: Artificial Sequence
<220> FEATURE:
<223> OTHER INFORMATION: A cell membrane permeable peptide

<400> SEQUENCE: 91

Thr Arg Ser Ser Arg Ala Gly Leu Gln Phe Pro Val Gly Arg Val His
1               5                10                15

Arg Leu Leu Arg Lys
            20

<210> SEQ ID NO 92
<211> LENGTH: 27
<212> TYPE: PRT
<213> ORGANISM: Artificial Sequence
<220> FEATURE:
<223> OTHER INFORMATION: A cell membrane permeable peptide

<400> SEQUENCE: 92

Gly Trp Thr Leu Asn Ser Ala Gly Tyr Leu Leu Gly Lys Ile Asn Leu
1               5                10                15

Lys Ala Leu Ala Ala Leu Ala Lys Lys Ile Leu
            20                25

<210> SEQ ID NO 93
<211> LENGTH: 18
<212> TYPE: PRT
<213> ORGANISM: Artificial Sequence
<220> FEATURE:
<223> OTHER INFORMATION: A cell membrane permeable peptide

<400> SEQUENCE: 93

Lys Leu Ala Leu Lys Leu Ala Leu Lys Ala Leu Lys Ala Ala Leu Lys
1               5                10                15

Leu Ala

<210> SEQ ID NO 94
```

```
<211> LENGTH: 16
<212> TYPE: PRT
<213> ORGANISM: Artificial Sequence
<220> FEATURE:
<223> OTHER INFORMATION: A cell membrane permeable peptide

<400> SEQUENCE: 94

Ala Ala Val Ala Leu Leu Pro Ala Val Leu Leu Ala Leu Leu Ala Pro
1               5                   10                  15

<210> SEQ ID NO 95
<211> LENGTH: 5
<212> TYPE: PRT
<213> ORGANISM: Artificial Sequence
<220> FEATURE:
<223> OTHER INFORMATION: A cell membrane permeable peptide

<400> SEQUENCE: 95

Val Pro Met Leu Lys
1               5

<210> SEQ ID NO 96
<211> LENGTH: 5
<212> TYPE: PRT
<213> ORGANISM: Artificial Sequence
<220> FEATURE:
<223> OTHER INFORMATION: A cell membrane permeable peptide

<400> SEQUENCE: 96

Pro Met Leu Lys Glu
1               5

<210> SEQ ID NO 97
<211> LENGTH: 28
<212> TYPE: PRT
<213> ORGANISM: Artificial Sequence
<220> FEATURE:
<223> OTHER INFORMATION: A cell membrane permeable peptide

<400> SEQUENCE: 97

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
            20                  25

<210> SEQ ID NO 98
<211> LENGTH: 18
<212> TYPE: PRT
<213> ORGANISM: Artificial Sequence
<220> FEATURE:
<223> OTHER INFORMATION: A cell membrane permeable peptide

<400> SEQUENCE: 98

Leu Leu Ile Ile Leu Arg Arg Arg Ile Arg Lys Gln Ala His Ala His
1               5                   10                  15

Ser Lys

<210> SEQ ID NO 99
<211> LENGTH: 21
<212> TYPE: PRT
<213> ORGANISM: Artificial Sequence
<220> FEATURE:
<223> OTHER INFORMATION: A cell membrane permeable peptide

<400> SEQUENCE: 99

Lys Glu Thr Trp Trp Glu Thr Trp Trp Thr Glu Trp Ser Gln Pro Lys
```

```
1               5               10              15

Lys Lys Arg Lys Val
            20

<210> SEQ ID NO 100
<211> LENGTH: 18
<212> TYPE: PRT
<213> ORGANISM: Artificial Sequence
<220> FEATURE:
<223> OTHER INFORMATION: A cell membrane permeable peptide

<400> SEQUENCE: 100

Arg Gly Gly Arg Leu Ser Tyr Ser Arg Arg Arg Phe Ser Thr Ser Thr
1               5               10              15

Gly Arg

<210> SEQ ID NO 101
<211> LENGTH: 15
<212> TYPE: PRT
<213> ORGANISM: Artificial Sequence
<220> FEATURE:
<223> OTHER INFORMATION: A cell membrane permeable peptide

<400> SEQUENCE: 101

Ser Asp Leu Trp Glu Met Met Met Val Ser Leu Ala Cys Gln Tyr
1               5               10              15

<210> SEQ ID NO 102
<211> LENGTH: 12
<212> TYPE: PRT
<213> ORGANISM: Artificial Sequence
<220> FEATURE:
<223> OTHER INFORMATION: A cell membrane permeable peptide

<400> SEQUENCE: 102

Thr Ser Pro Leu Asn Ile His Asn Gly Gln Lys Leu
1               5               10

<210> SEQ ID NO 103
<211> LENGTH: 16
<212> TYPE: PRT
<213> ORGANISM: Artificial Sequence
<220> FEATURE:
<223> OTHER INFORMATION: A cell membrane permeable peptide

<400> SEQUENCE: 103

Arg Gln Ile Lys Ile Trp Phe Gln Asn Arg Arg Met Lys Trp Lys Lys
1               5               10              15

<210> SEQ ID NO 104
<211> LENGTH: 32
<212> TYPE: PRT
<213> ORGANISM: Artificial Sequence
<220> FEATURE:
<223> OTHER INFORMATION: PHB2 derived peptide 1-32aa

<400> SEQUENCE: 104

Met Ala Gln Asn Leu Lys Asp Leu Ala Gly Arg Leu Pro Ala Gly Pro
1               5               10              15

Arg Gly Met Gly Thr Ala Leu Lys Leu Leu Leu Gly Ala Gly Ala Val
            20              25              30

<210> SEQ ID NO 105
<211> LENGTH: 37
<212> TYPE: PRT
```

```
<213> ORGANISM: Artificial Sequence
<220> FEATURE:
<223> OTHER INFORMATION: PHB2 derived peptide 63-99aa

<400> SEQUENCE: 105

Ile Leu Ala Glu Gly Leu His Phe Arg Ile Pro Trp Phe Gln Tyr Pro
1               5                   10                  15

Ile Ile Tyr Asp Ile Arg Ala Arg Pro Arg Lys Ile Ser Ser Pro Thr
            20                  25                  30

Gly Ser Lys Asp Leu
        35

<210> SEQ ID NO 106
<211> LENGTH: 21
<212> TYPE: PRT
<213> ORGANISM: Artificial Sequence
<220> FEATURE:
<223> OTHER INFORMATION: cross-linked peptide containing PHB2 derived
      peptide 11-21aa
<220> FEATURE:
<221> NAME/KEY: MISC_FEATURE
<222> LOCATION: (1)..(13)
<223> OTHER INFORMATION: linked by using hexafluorobenzene
<220> FEATURE:
<221> NAME/KEY: MISC_FEATURE
<222> LOCATION: (10)..(10)
<223> OTHER INFORMATION: Xaa = Nle

<400> SEQUENCE: 106

Cys Arg Leu Pro Ala Gly Pro Arg Gly Xaa Gly Thr Cys Arg Arg Arg
1               5                   10                  15

Arg Arg Arg Arg Arg
            20

<210> SEQ ID NO 107
<211> LENGTH: 21
<212> TYPE: PRT
<213> ORGANISM: Artificial Sequence
<220> FEATURE:
<223> OTHER INFORMATION: cross-linked peptide containing PHB2 derived
      peptide 11-21aa
<220> FEATURE:
<221> NAME/KEY: MISC_FEATURE
<222> LOCATION: (1)..(13)
<223> OTHER INFORMATION: linked by using decafluorobiphenyl
<220> FEATURE:
<221> NAME/KEY: MISC_FEATURE
<222> LOCATION: (10)..(10)
<223> OTHER INFORMATION: Xaa = Nle

<400> SEQUENCE: 107

Cys Arg Leu Pro Ala Gly Pro Arg Gly Xaa Gly Thr Cys Arg Arg Arg
1               5                   10                  15

Arg Arg Arg Arg Arg
            20

<210> SEQ ID NO 108
<211> LENGTH: 21
<212> TYPE: PRT
<213> ORGANISM: Artificial Sequence
<220> FEATURE:
<223> OTHER INFORMATION: cross-linked peptide containing PHB2 derived
      peptide 11-21aa
<220> FEATURE:
<221> NAME/KEY: DISULFID
<222> LOCATION: (1)..(13)
<220> FEATURE:
<221> NAME/KEY: MISC_FEATURE
<222> LOCATION: (10)..(10)
```

```
<223> OTHER INFORMATION: Xaa = Nle

<400> SEQUENCE: 108

Cys Arg Leu Pro Ala Gly Pro Arg Gly Xaa Gly Thr Cys Arg Arg Arg
1               5                   10                  15

Arg Arg Arg Arg Arg
            20

<210> SEQ ID NO 109
<211> LENGTH: 21
<212> TYPE: PRT
<213> ORGANISM: Artificial Sequence
<220> FEATURE:
<223> OTHER INFORMATION: uncross-linked peptide containing PHB2 derived
      peptide 11-21aa
<220> FEATURE:
<221> NAME/KEY: MISC_FEATURE
<222> LOCATION: (10)..(10)
<223> OTHER INFORMATION: Xaa = Nle

<400> SEQUENCE: 109

Ala Arg Leu Pro Ala Gly Pro Arg Gly Xaa Gly Thr Ala Arg Arg Arg
1               5                   10                  15

Arg Arg Arg Arg Arg
            20

<210> SEQ ID NO 110
<211> LENGTH: 23
<212> TYPE: PRT
<213> ORGANISM: Artificial Sequence
<220> FEATURE:
<223> OTHER INFORMATION: cross-linked peptide containing PHB2 derived
      peptide 76-88aa
<220> FEATURE:
<221> NAME/KEY: MISC_FEATURE
<222> LOCATION: (1)..(15)
<223> OTHER INFORMATION: linked by using hexafluorobenzene

<400> SEQUENCE: 110

Cys Gln Tyr Pro Ile Ile Tyr Asp Ile Arg Ala Arg Pro Arg Cys Arg
1               5                   10                  15

Arg Arg Arg Arg Arg Arg Arg
            20

<210> SEQ ID NO 111
<211> LENGTH: 23
<212> TYPE: PRT
<213> ORGANISM: Artificial Sequence
<220> FEATURE:
<223> OTHER INFORMATION: cross-linked peptide containing PHB2 derived
      peptide 76-88aa
<220> FEATURE:
<221> NAME/KEY: MISC_FEATURE
<222> LOCATION: (1)..(15)
<223> OTHER INFORMATION: linked by using decafluorobiphenyl

<400> SEQUENCE: 111

Cys Gln Tyr Pro Ile Ile Tyr Asp Ile Arg Ala Arg Pro Arg Cys Arg
1               5                   10                  15

Arg Arg Arg Arg Arg Arg Arg
            20

<210> SEQ ID NO 112
<211> LENGTH: 23
<212> TYPE: PRT
<213> ORGANISM: Artificial Sequence
<220> FEATURE:
```

```
<223> OTHER INFORMATION: cross-linked peptide containing PHB2 derived
      peptide 76-88aa
<220> FEATURE:
<221> NAME/KEY: DISULFID
<222> LOCATION: (1)..(15)

<400> SEQUENCE: 112

Cys Gln Tyr Pro Ile Ile Tyr Asp Ile Arg Ala Arg Pro Arg Cys Arg
1               5                   10                  15

Arg Arg Arg Arg Arg Arg Arg
            20

<210> SEQ ID NO 113
<211> LENGTH: 23
<212> TYPE: PRT
<213> ORGANISM: Artificial Sequence
<220> FEATURE:
<223> OTHER INFORMATION: uncross-linked peptide containing PHB2 derived
      peptide 76-88aa

<400> SEQUENCE: 113

Ala Gln Tyr Pro Ile Ile Tyr Asp Ile Arg Ala Arg Pro Arg Ala Arg
1               5                   10                  15

Arg Arg Arg Arg Arg Arg Arg
            20

<210> SEQ ID NO 114
<211> LENGTH: 21
<212> TYPE: PRT
<213> ORGANISM: Artificial Sequence
<220> FEATURE:
<223> OTHER INFORMATION: uncross-linked peptide containing PHB2 derived
      peptide 11-21aa

<400> SEQUENCE: 114

Ala Arg Leu Pro Ala Gly Pro Arg Gly Met Gly Thr Ala Arg Arg Arg
1               5                   10                  15

Arg Arg Arg Arg Arg
            20

<210> SEQ ID NO 115
<211> LENGTH: 13
<212> TYPE: PRT
<213> ORGANISM: Artificial Sequence
<220> FEATURE:
<223> OTHER INFORMATION: cross-linked peptide containing PHB2 derived
      peptide 11-21aa
<220> FEATURE:
<221> NAME/KEY: MISC_FEATURE
<222> LOCATION: (1)..(13)
<223> OTHER INFORMATION: linked by using hexafluorobenzene
<220> FEATURE:
<221> NAME/KEY: MISC_FEATURE
<222> LOCATION: (10)..(10)
<223> OTHER INFORMATION: Xaa = Nle

<400> SEQUENCE: 115

Cys Arg Leu Pro Ala Gly Pro Arg Gly Xaa Gly Thr Cys
1               5                   10

<210> SEQ ID NO 116
<211> LENGTH: 13
<212> TYPE: PRT
<213> ORGANISM: Artificial Sequence
<220> FEATURE:
<223> OTHER INFORMATION: cross-linked peptide containing PHB2 derived
      peptide 11-21aa
<220> FEATURE:
```

-continued

```
<221> NAME/KEY: MISC_FEATURE
<222> LOCATION: (1)..(13)
<223> OTHER INFORMATION: linked by using decafluorobiphenyl
<220> FEATURE:
<221> NAME/KEY: MISC_FEATURE
<222> LOCATION: (10)..(10)
<223> OTHER INFORMATION: Xaa = Nle

<400> SEQUENCE: 116

Cys Arg Leu Pro Ala Gly Pro Arg Gly Xaa Gly Thr Cys
1               5                   10

<210> SEQ ID NO 117
<211> LENGTH: 13
<212> TYPE: PRT
<213> ORGANISM: Artificial Sequence
<220> FEATURE:
<223> OTHER INFORMATION: cross-linked peptide containing PHB2 derived
      peptide 11-21aa
<220> FEATURE:
<221> NAME/KEY: DISULFID
<222> LOCATION: (1)..(13)
<220> FEATURE:
<221> NAME/KEY: MISC_FEATURE
<222> LOCATION: (10)..(10)
<223> OTHER INFORMATION: Xaa = Nle

<400> SEQUENCE: 117

Cys Arg Leu Pro Ala Gly Pro Arg Gly Xaa Gly Thr Cys
1               5                   10

<210> SEQ ID NO 118
<211> LENGTH: 13
<212> TYPE: PRT
<213> ORGANISM: Artificial Sequence
<220> FEATURE:
<223> OTHER INFORMATION: uncross-linked peptide containing PHB2 derived
      peptide 11-21aa
<220> FEATURE:
<221> NAME/KEY: MISC_FEATURE
<222> LOCATION: (10)..(10)
<223> OTHER INFORMATION: Xaa = Nle

<400> SEQUENCE: 118

Ala Arg Leu Pro Ala Gly Pro Arg Gly Xaa Gly Thr Ala
1               5                   10

<210> SEQ ID NO 119
<211> LENGTH: 15
<212> TYPE: PRT
<213> ORGANISM: Artificial Sequence
<220> FEATURE:
<223> OTHER INFORMATION: cross-linked peptide containing PHB2 derived
      peptide 76-88aa
<220> FEATURE:
<221> NAME/KEY: MISC_FEATURE
<222> LOCATION: (1)..(15)
<223> OTHER INFORMATION: linked by using hexafluorobenzene

<400> SEQUENCE: 119

Cys Gln Tyr Pro Ile Ile Tyr Asp Ile Arg Ala Arg Pro Arg Cys
1               5                   10                  15

<210> SEQ ID NO 120
<211> LENGTH: 15
<212> TYPE: PRT
<213> ORGANISM: Artificial Sequence
<220> FEATURE:
<223> OTHER INFORMATION: cross-linked peptide containing PHB2 derived
      peptide 76-88aa
<220> FEATURE:
```

```
<221> NAME/KEY: MISC_FEATURE
<222> LOCATION: (1)..(15)
<223> OTHER INFORMATION: linked by using decafluorobiphenyl

<400> SEQUENCE: 120

Cys Gln Tyr Pro Ile Ile Tyr Asp Ile Arg Ala Arg Pro Arg Cys
1               5               10              15

<210> SEQ ID NO 121
<211> LENGTH: 15
<212> TYPE: PRT
<213> ORGANISM: Artificial Sequence
<220> FEATURE:
<223> OTHER INFORMATION: cross-linked peptide containing PHB2 derived
      peptide 76-88aa
<220> FEATURE:
<221> NAME/KEY: DISULFID
<222> LOCATION: (1)..(15)

<400> SEQUENCE: 121

Cys Gln Tyr Pro Ile Ile Tyr Asp Ile Arg Ala Arg Pro Arg Cys
1               5               10              15

<210> SEQ ID NO 122
<211> LENGTH: 15
<212> TYPE: PRT
<213> ORGANISM: Artificial Sequence
<220> FEATURE:
<223> OTHER INFORMATION: uncross-linked peptide containing PHB2 derived
      peptide 76-88aa

<400> SEQUENCE: 122

Ala Gln Tyr Pro Ile Ile Tyr Asp Ile Arg Ala Arg Pro Arg Ala
1               5               10              15

<210> SEQ ID NO 123
<211> LENGTH: 19
<212> TYPE: PRT
<213> ORGANISM: Artificial Sequence
<220> FEATURE:
<223> OTHER INFORMATION: cross-linked cyclic peptide containing PHB2
      derived peptide 11-21aa
<220> FEATURE:
<221> NAME/KEY: MISC_FEATURE
<222> LOCATION: (1)..(13)
<223> OTHER INFORMATION: linked by using hexafluorobenzene
<220> FEATURE:
<221> NAME/KEY: MISC_FEATURE
<222> LOCATION: (10)..(10)
<223> OTHER INFORMATION: Xaa = Nle
<220> FEATURE:
<221> NAME/KEY: MISC_FEATURE
<222> LOCATION: (15)..(15)
<223> OTHER INFORMATION: Xaa = Nal

<400> SEQUENCE: 123

Cys Arg Leu Pro Ala Gly Pro Arg Gly Xaa Gly Thr Cys Phe Xaa Arg
1               5               10              15

Arg Arg Arg

<210> SEQ ID NO 124
<211> LENGTH: 19
<212> TYPE: PRT
<213> ORGANISM: Artificial Sequence
<220> FEATURE:
<223> OTHER INFORMATION: cross-linked cyclic peptide containing PHB2
      derived peptide 11-21aa
<220> FEATURE:
<221> NAME/KEY: MISC_FEATURE
<222> LOCATION: (1)..(13)
```

<223> OTHER INFORMATION: linked by using decafluorobiphenyl
<220> FEATURE:
<221> NAME/KEY: MISC_FEATURE
<222> LOCATION: (10)..(10)
<223> OTHER INFORMATION: Xaa = Nle
<220> FEATURE:
<221> NAME/KEY: MISC_FEATURE
<222> LOCATION: (15)..(15)
<223> OTHER INFORMATION: Xaa = Nal

<400> SEQUENCE: 124

Cys Arg Leu Pro Ala Gly Pro Arg Gly Xaa Gly Thr Cys Phe Xaa Arg
1               5                   10                  15

Arg Arg Arg

<210> SEQ ID NO 125
<211> LENGTH: 19
<212> TYPE: PRT
<213> ORGANISM: Artificial Sequence
<220> FEATURE:
<223> OTHER INFORMATION: uncross-linked cyclic peptide containing PHB2
      derived peptide 11-21aa
<220> FEATURE:
<221> NAME/KEY: MISC_FEATURE
<222> LOCATION: (10)..(10)
<223> OTHER INFORMATION: Xaa = Nle
<220> FEATURE:
<221> NAME/KEY: MISC_FEATURE
<222> LOCATION: (15)..(15)
<223> OTHER INFORMATION: Xaa = Nal

<400> SEQUENCE: 125

Ala Arg Leu Pro Ala Gly Pro Arg Gly Xaa Gly Thr Ala Phe Xaa Arg
1               5                   10                  15

Arg Arg Arg

<210> SEQ ID NO 126
<211> LENGTH: 21
<212> TYPE: PRT
<213> ORGANISM: Artificial Sequence
<220> FEATURE:
<223> OTHER INFORMATION: cross-linked cyclic peptide containing PHB2
      derived peptide 76-88aa
<220> FEATURE:
<221> NAME/KEY: MISC_FEATURE
<222> LOCATION: (1)..(15)
<223> OTHER INFORMATION: linked by using hexafluorobenzene
<220> FEATURE:
<221> NAME/KEY: MISC_FEATURE
<222> LOCATION: (17)..(17)
<223> OTHER INFORMATION: Xaa = Nal

<400> SEQUENCE: 126

Cys Gln Tyr Pro Ile Ile Tyr Asp Ile Arg Ala Arg Pro Arg Cys Phe
1               5                   10                  15

Xaa Arg Arg Arg Arg
            20

<210> SEQ ID NO 127
<211> LENGTH: 21
<212> TYPE: PRT
<213> ORGANISM: Artificial Sequence
<220> FEATURE:
<223> OTHER INFORMATION: cross-linked cyclic peptide containing PHB2
      derived peptide 76-88aa
<220> FEATURE:
<221> NAME/KEY: MISC_FEATURE
<222> LOCATION: (1)..(15)
<223> OTHER INFORMATION: linked by using decafluorobiphenyl
<220> FEATURE:

```
<221> NAME/KEY: MISC_FEATURE
<222> LOCATION: (17)..(17)
<223> OTHER INFORMATION: Xaa = Nal

<400> SEQUENCE: 127

Cys Gln Tyr Pro Ile Ile Tyr Asp Ile Arg Ala Arg Pro Arg Cys Phe
1               5                   10                  15

Xaa Arg Arg Arg Arg
            20

<210> SEQ ID NO 128
<211> LENGTH: 21
<212> TYPE: PRT
<213> ORGANISM: Artificial Sequence
<220> FEATURE:
<223> OTHER INFORMATION: uncross-linked cyclic peptide containing PHB2
      derived peptide 76-88aa
<220> FEATURE:
<221> NAME/KEY: MISC_FEATURE
<222> LOCATION: (17)..(17)
<223> OTHER INFORMATION: Xaa = Nal

<400> SEQUENCE: 128

Ala Gln Tyr Pro Ile Ile Tyr Asp Ile Arg Ala Arg Pro Arg Ala Phe
1               5                   10                  15

Xaa Arg Arg Arg Arg
            20

<210> SEQ ID NO 129
<211> LENGTH: 20
<212> TYPE: PRT
<213> ORGANISM: Artificial Sequence
<220> FEATURE:
<223> OTHER INFORMATION: modified PHB2 peptide
<220> FEATURE:
<221> NAME/KEY: MISC_FEATURE
<222> LOCATION: (8)..(8)
<223> OTHER INFORMATION: D-Ala

<400> SEQUENCE: 129

Arg Leu Pro Ala Gly Pro Arg Ala Met Gly Thr Ala Arg Arg Arg Arg
1               5                   10                  15

Arg Arg Arg Arg
            20

<210> SEQ ID NO 130
<211> LENGTH: 20
<212> TYPE: PRT
<213> ORGANISM: Artificial Sequence
<220> FEATURE:
<223> OTHER INFORMATION: modified PHB2 peptide
<220> FEATURE:
<221> NAME/KEY: MISC_FEATURE
<222> LOCATION: (5)..(5)
<223> OTHER INFORMATION: D-Ala

<400> SEQUENCE: 130

Arg Leu Pro Ala Ala Pro Arg Gly Met Gly Thr Ala Arg Arg Arg Arg
1               5                   10                  15

Arg Arg Arg Arg
            20

<210> SEQ ID NO 131
<211> LENGTH: 20
<212> TYPE: PRT
<213> ORGANISM: Artificial Sequence
<220> FEATURE:
```

-continued

```
<223> OTHER INFORMATION: modified PHB2 peptide
<220> FEATURE:
<221> NAME/KEY: MISC_FEATURE
<222> LOCATION: (8)..(8)
<223> OTHER INFORMATION: D-Leu

<400> SEQUENCE: 131

Arg Leu Pro Ala Gly Pro Arg Leu Met Gly Thr Ala Arg Arg Arg Arg
1               5                   10                  15

Arg Arg Arg Arg
            20

<210> SEQ ID NO 132
<211> LENGTH: 20
<212> TYPE: PRT
<213> ORGANISM: Artificial Sequence
<220> FEATURE:
<223> OTHER INFORMATION: modified PHB2 peptide
<220> FEATURE:
<221> NAME/KEY: MISC_FEATURE
<222> LOCATION: (5)..(5)
<223> OTHER INFORMATION: D-Leu

<400> SEQUENCE: 132

Arg Leu Pro Ala Leu Pro Arg Gly Met Gly Thr Ala Arg Arg Arg Arg
1               5                   10                  15

Arg Arg Arg Arg
            20

<210> SEQ ID NO 133
<211> LENGTH: 20
<212> TYPE: PRT
<213> ORGANISM: Artificial Sequence
<220> FEATURE:
<223> OTHER INFORMATION: modified PHB2 peptide
<220> FEATURE:
<221> NAME/KEY: MISC_FEATURE
<222> LOCATION: (5)..(5)
<223> OTHER INFORMATION: D-Ala
<220> FEATURE:
<221> NAME/KEY: MISC_FEATURE
<222> LOCATION: (8)..(8)
<223> OTHER INFORMATION: D-Ala

<400> SEQUENCE: 133

Arg Leu Pro Ala Ala Pro Arg Ala Met Gly Thr Ala Arg Arg Arg Arg
1               5                   10                  15

Arg Arg Arg Arg
            20

<210> SEQ ID NO 134
<211> LENGTH: 20
<212> TYPE: PRT
<213> ORGANISM: Artificial Sequence
<220> FEATURE:
<223> OTHER INFORMATION: modified PHB2 peptide
<220> FEATURE:
<221> NAME/KEY: MISC_FEATURE
<222> LOCATION: (5)..(5)
<223> OTHER INFORMATION: D-Leu
<220> FEATURE:
<221> NAME/KEY: MISC_FEATURE
<222> LOCATION: (8)..(8)
<223> OTHER INFORMATION: D-Leu

<400> SEQUENCE: 134

Arg Leu Pro Ala Leu Pro Arg Leu Met Gly Thr Ala Arg Arg Arg Arg
1               5                   10                  15
```

-continued

```
Arg Arg Arg Arg
            20

<210> SEQ ID NO 135
<211> LENGTH: 20
<212> TYPE: PRT
<213> ORGANISM: Artificial Sequence
<220> FEATURE:
<223> OTHER INFORMATION: modified PHB2 peptide
<220> FEATURE:
<221> NAME/KEY: MISC_FEATURE
<222> LOCATION: (5)..(5)
<223> OTHER INFORMATION: D-Ala
<220> FEATURE:
<221> NAME/KEY: MISC_FEATURE
<222> LOCATION: (8)..(8)
<223> OTHER INFORMATION: D-Leu

<400> SEQUENCE: 135

Arg Leu Pro Ala Ala Pro Arg Leu Met Gly Thr Ala Arg Arg Arg Arg
1               5                  10                  15

Arg Arg Arg Arg
            20

<210> SEQ ID NO 136
<211> LENGTH: 20
<212> TYPE: PRT
<213> ORGANISM: Artificial Sequence
<220> FEATURE:
<223> OTHER INFORMATION: modified PHB2 peptide
<220> FEATURE:
<221> NAME/KEY: MISC_FEATURE
<222> LOCATION: (5)..(5)
<223> OTHER INFORMATION: D-Leu
<220> FEATURE:
<221> NAME/KEY: MISC_FEATURE
<222> LOCATION: (8)..(8)
<223> OTHER INFORMATION: D-Ala

<400> SEQUENCE: 136

Arg Leu Pro Ala Leu Pro Arg Ala Met Gly Thr Ala Arg Arg Arg Arg
1               5                  10                  15

Arg Arg Arg Arg
            20
```